US012760024B2

(12) United States Patent
Xu et al.

(10) Patent No.: US 12,760,024 B2
(45) Date of Patent: Oct. 13, 2026

(54) SUBSTITUTED BENZO[D][1,3]DIOXOLES AS BTK AND/OR JAK3 KINASE INHIBITORS

(71) Applicant: XI'AN XINTONG PHARMACEUTICAL RESEARCH CO., LTD., Xi'an (CN)

(72) Inventors: Yungen Xu, Xi'an (CN); Tingting Liang, Xi'an (CN); Qihua Zhu, Xi'an (CN); Junjie Wang, Xi'an (CN); Lifang Cen, Xi'an (CN); Wenjie Wang, Xi'an (CN); Jiaming Jin, Xi'an (CN)

(73) Assignee: XI'AN XINTONG PHARMACEUTICAL RESEARCH CO., LTD., Xi'an (CN)

(*) Notice: Subject to any disclaimer, the term of this patent is extended or adjusted under 35 U.S.C. 154(b) by 537 days.

(21) Appl. No.: 18/257,027

(22) PCT Filed: Mar. 24, 2022

(86) PCT No.: PCT/CN2022/082684

§ 371 (c)(1),
(2) Date: Jun. 12, 2023

(87) PCT Pub. No.: WO2022/206531

PCT Pub. Date: Oct. 6, 2022

(65) Prior Publication Data

US 2024/0059694 A1 Feb. 22, 2024

(30) Foreign Application Priority Data

Apr. 1, 2021 (CN) ......................... 202110357313.2

(51) Int. Cl.
*A61K 31/36* (2006.01)
*C07D 487/04* (2006.01)
*C07D 493/04* (2006.01)

(52) U.S. Cl.
CPC .................................. *C07D 487/04* (2013.01)

(58) Field of Classification Search
CPC .............................. A61K 31/36; C07D 493/04
USPC .......................................... 514/469; 549/434
See application file for complete search history.

(56) References Cited

FOREIGN PATENT DOCUMENTS

WO 2020231990 A1 11/2020

OTHER PUBLICATIONS

International Search Report (PCT/ISA/210) with English translation, and Written Opinion (PCT/ISA/237) mailed on Jun. 22, 2022, by the China national Intellectual Property Administration as the International Searching Authority for international Application No. PCT/CN2022/082684. (8 pages).

*Primary Examiner* — Douglas M Willis
(74) *Attorney, Agent, or Firm* — BUCHANAN INGERSOLL & ROONEY PC

(57) ABSTRACT

Disclosed herein is a 1,3-benzodioxol derivative as shown in general formula (I). Results of pharmacological experiments indicate that the compound of Formula (I) can exert excellent inhibition on both BTK and JAK3 kinases, and can be used to prepare medicines for treating rheumatoid arthritis caused by over-activation of BTK and/or JAK3 pathways. The disclosure further describes a preparation method for the 1,3-benzodioxol derivative.

(Formula I)

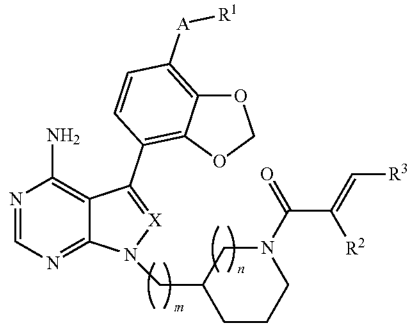

15 Claims, No Drawings

SUBSTITUTED BENZO[D][1,3]DIOXOLES AS BTK AND/OR JAK3 KINASE INHIBITORS

FIELD OF THE INVENTION

The invention is within the field of medicinal chemistry, and specifically relates to a type of Bruton's tyrosine kinase (BTK) and Janus kinase subtype 3 (JAK3) kinase inhibitors containing 1,3-benzodioxol structures, and their preparation methods; it also includes pharmaceutical compositions containing these compounds and their use in the preparation of therapeutic drugs used for the treatment of autoimmune diseases such as rheumatoid arthritis or B cell lymphoma, or the drugs used to treat B cell malignancies.

BACKGROUND OF THE INVENTION

Rheumatoid arthritis (RA) is a chronic, inflammatory synovitis-based autoimmune disease of unknown etiology, whose main pathological manifestations are inflammatory cell infiltration in synovial tissue, pannus formation, and progressive articular cartilage and bone deterioration, eventually leading to joint deformity or even loss of function.

Janus Kinase (JAK) includes non-receptor tyrosine kinases, including four subtypes, i.e. JAK1, JAK2, JAK3, and TYK2. A variety of JAK inhibitors are currently on the market, such as Tofacitinib, Ruxolitinib and Baricitinib. Tofacitinib was released in 2012 for the treatment of moderate to severe rheumatoid arthritis, and was approved for the treatment of psoriatic arthritis in 2017. However, tofacitinib has serious side effects including infection and anemia. This mainly occurs because tofacitinib is a pan-JAK inhibitor. While inhibiting JAK1 and JAK3 to produce therapeutic effects, tofacitinib also inhibits JAK2 activity and induces anemia as a side effect. Therefore, selective JAK1 or JAK3 inhibitors should be developed in the treatment of rheumatoid arthritis. Since JAK1 can form dimers with JAK3 and dimers/multimers with JAK2 or TYK2, it can cause side effects. Therefore, the side effects caused by the selective inhibition of JAK3 may be less intense than those caused by the inhibition of JAK1.

Bruton's tyrosine kinase (BTK) is a member of the TEC family and belongs to the group of non-receptor tyrosine kinases. It is mainly expressed in B cells, myeloid cells, mast cells, and platelets, but does not occur in T cells and NK cells. Bruton's tyrosine kinase plays a vital role in the B cell receptor signaling pathway. In addition, BTK is also involved in the conduction of many other signaling pathways. Abnormal activation of B cells can lead to B-cell lymphomas and autoimmune diseases. Three BTK inhibitors are currently on the market including Ibrutinib, Acalabrutinib and Zanubrutinib.

It has been reported that the combined use of BTK inhibitor LFM-A13 and JAK3 inhibitor JANEX-1 in the treatment of graft-versus-host reaction (GVHR) is much better than using LFM-A13, JANEX-1 or methotrexate alone. In addition, the JAK3 selective inhibitor PF-06651600 has shown good anti-RA effects in clinical practice. The reason is not only related to the inhibition of JAK3, but also closely related to the inhibition of TEC family kinases such as BTK. Therefore, the inventors believe that the simultaneous inhibition of BTK and JAK3 has a synergistic effect on the treatment of autoimmune diseases such as RA. However, those skilled in the art would prefer to combine existing BTK and JAK3 inhibitors; however, it is difficult to obtain compounds with excellent BTK and JAK3 inhibitory activities at the same time according to previous research. However, the inventors unexpectedly developed a series of compounds, which not only have inhibitory activity on BTK, but also have highly selective inhibitory activity on JAK3.

SUMMARY OF THE INVENTION

The invention provides a class of compounds containing a 1,3-benzodioxol structure, which can simultaneously inhibit BTK and JAK3. In addition, the invention also provides specific preparation methods of the compounds and their pharmaceutical application as BTK and JAK3 kinase inhibitors.

Specifically, the present invention provides a class of 1,3-benzodioxol derivatives represented by general formula (I) or their pharmaceutically acceptable salts thereof:

(I)

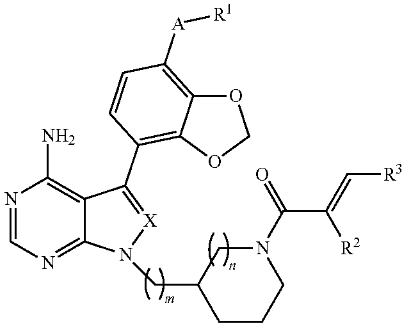

where X represents N or CH; A represents O, S, —NHCO—, —$NHCOCH_2$— or —$NHSO_2$—; m represents 0 or 1, and n represents 0 or 1;

$R^1$ represents:

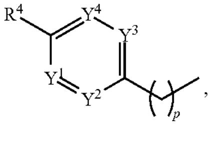,
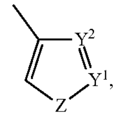,
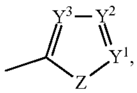,
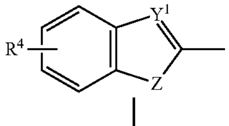,
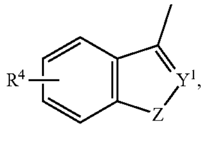,
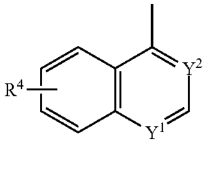
or
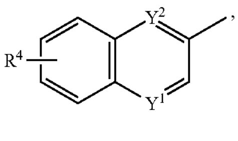, wherein p represents 0 or 1; $R^4$ represents H, F, Cl, Br, I, $C_1$-$C_6$ alkyl, $CF_3$, OH, $C_1$-$C_6$ alkoxy, $OCF_3$, CN, $NO_2$, $NH_2$, $C_1$-$C_6$ alkylamino, $N(CH_3)_2$, $N(C_2H_5)_2$, $NHCOCH_3$, $CONH_2$, $CONHCH_3$, $CONHCH_2CF_3$, $OCH_2CH_2OCH_3$, $C_6H_5$,

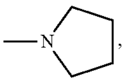, 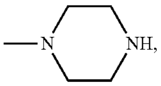, 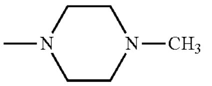 or

-continued

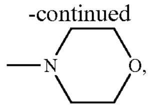

$R^4$ can be monosubstituted, disubstituted or trisubstituted; $Y^1$, $Y^2$, $Y^3$ or $Y^4$ represent N or C—$R^5$, $R^5$ represents H, F, Cl, Br, I, $CH_3$, $CF_3$, OH, $OCH_3$, $OCF_3$ or CN; Z represents O, S or N—$R^6$, $R^6$ represents H, $CH_3$ or $C_2H_5$ or cyclopropyl; $R^2$ represents H, Cl, Br or CN; $R^3$ represents H, substituted $C_1$-$C_6$ alkyl, substituted $C_2$-$C_6$ heterocycloalkyl, wherein the substituent is OH, $NH_2$, $OCH_3$, $NHCH_3$ or $NHCOCH_3$, and the heterocycloalkyl as stated contains the four-, five- or six-membered saturated heterocycloalkyl group with 1-3 O, N or S atoms.

Preferably in the general formula (I), A is —NHCO— or —$NHSO_2$—, more preferably A is —NHCO—; when m represents 1, n preferably represents 0; when m represents 0, n preferably represents 1; $R^2$, $R^3$ preferably represents H.

The compounds of the invention preferably have the following general formula (II):

(II)

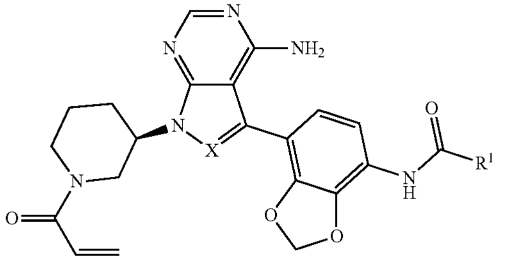

where: X and $R^1$ are as defined above.

Preferably in general formula (II), $R^1$ represents

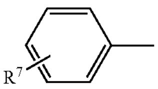,
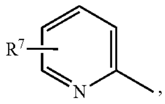,
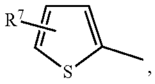,
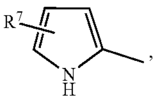,
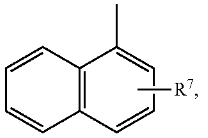,
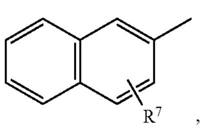,
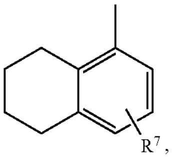,
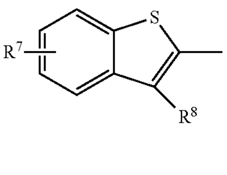 or 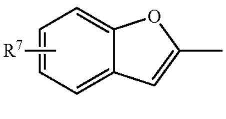, wherein $R^7$ represents H, F, Cl, Br, $CH_3$, t-Bu, $CH_3$, t-Bu, $CF_3$, CN, OH, $OCH_3$, $OCF_3$, $NH_2$, $N(CH_3)_2$, $N(C_2H_5)_2$, $NHCOCH_3$, $CONH_2$, $CONHCH_3$, $CONHCH_2CF_3$, $C_6H_5$,

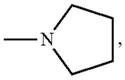, 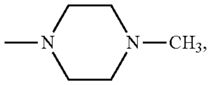, or, 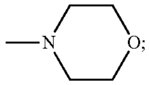;

$R^7$ can be mono-, di- or tri-substituted, and $R^8$ represents H, Cl or $CH_3$.

Further, $R^7$ preferably represents H, Cl, $CH_3$, t-Bu, $CF_3$, $OCH_3$, $N(CH_3)_2$, $N(C_2H_5)_2$ or $CONHCH_2CF_3$; $R^7$ can be mono-, di- or tri-substituted; $R^8$ preferably represents Cl.

More preferably, the 34 types of 1,3-benzodioxol derivatives of the invention are numbered sequentially as follows: I-1, I-2, I-3, . . . and I-34. For example, the 1,3-benzodioxol derivatives of the invention are numbered sequentially as follows: I-1, I-2, I-3, . . . and I-32.

Further preferably, the 1,3-benzodioxol derivatives of the invention are selected from the following compounds:

I-1

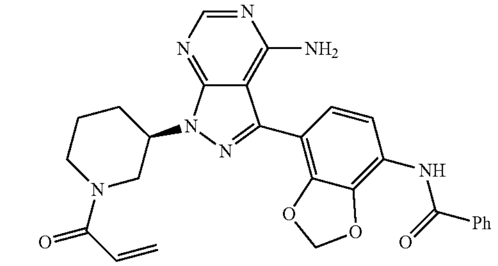

I-2

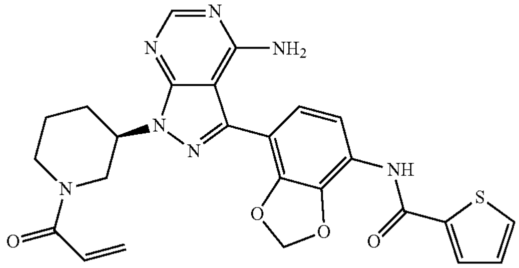

I-3

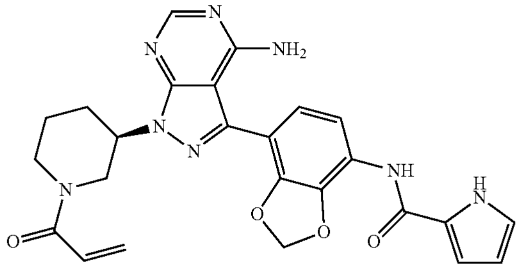

I-4

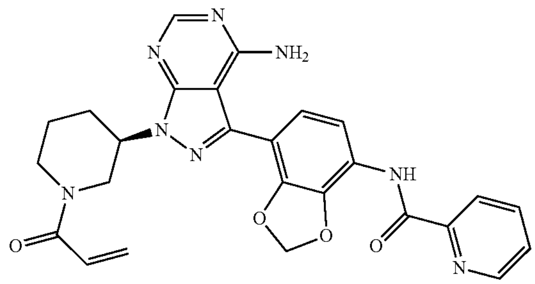

-continued
I-5
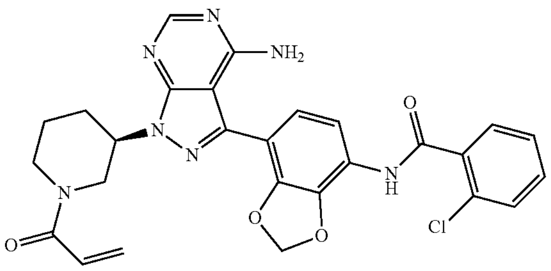
I-6
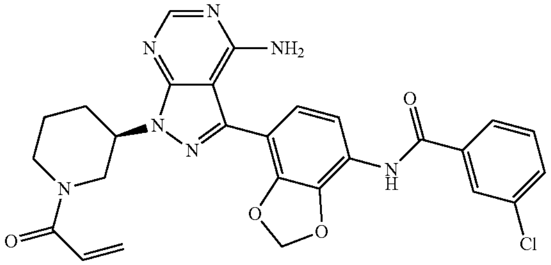
I-7
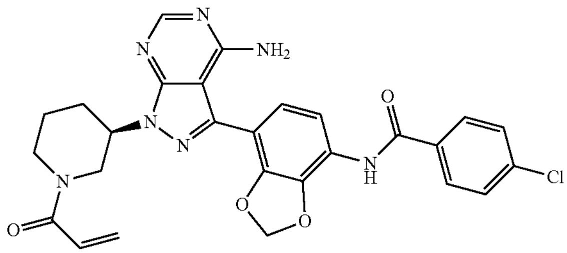
I-8
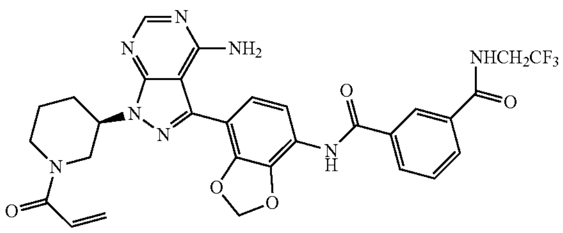
I-9
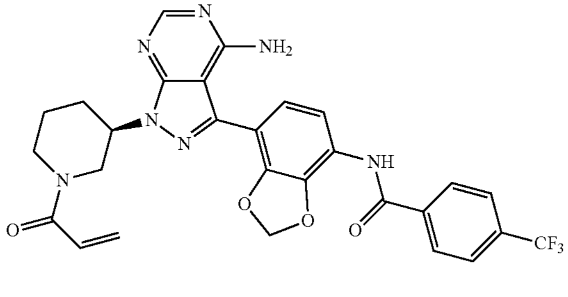
-continued
I-10
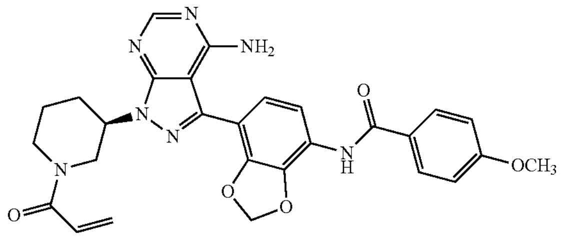
I-11
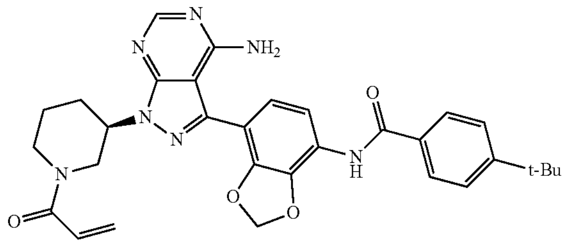
I-12
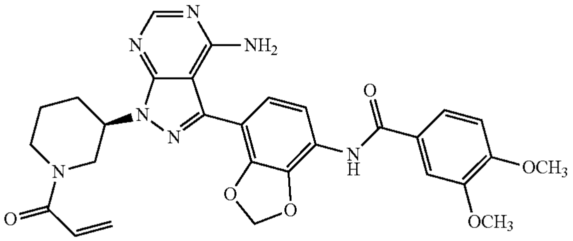
I-13
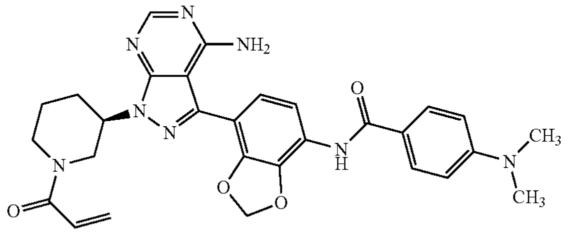
I-14
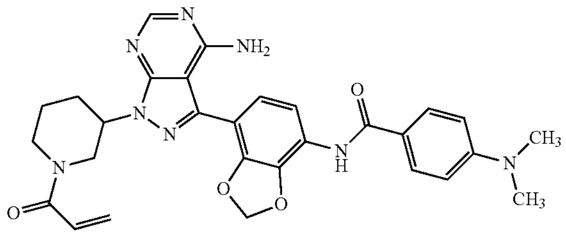
I-15
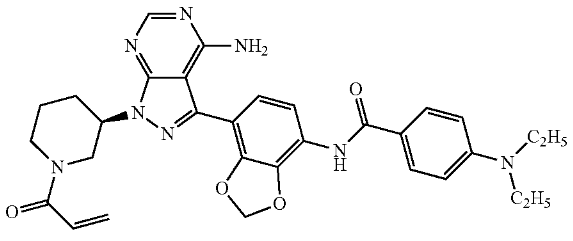

-continued
I-16
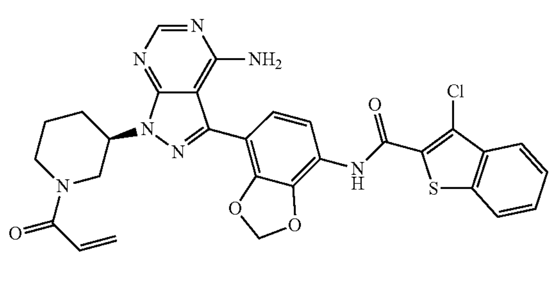
I-17
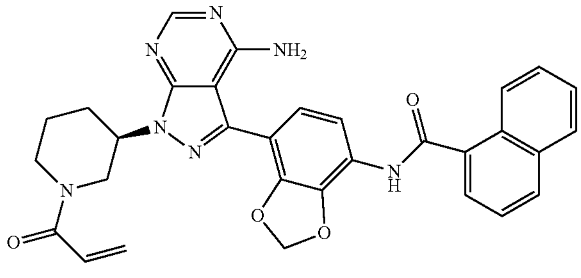
I-18
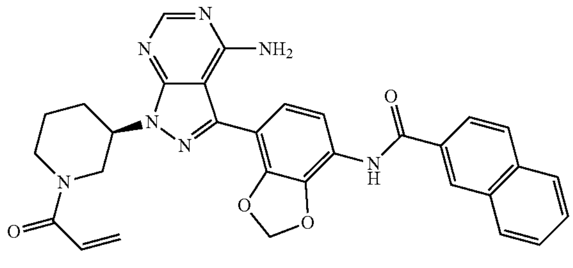
I-19
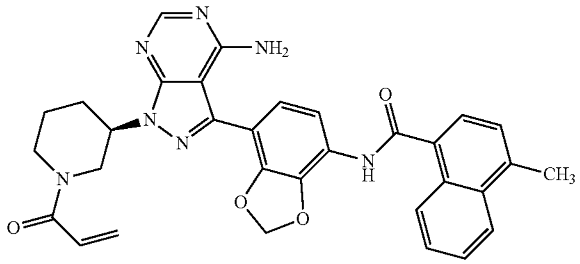
I-20
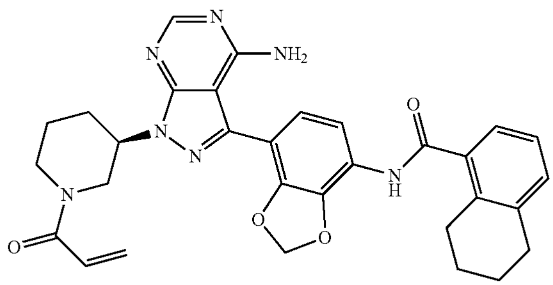
-continued
I-21
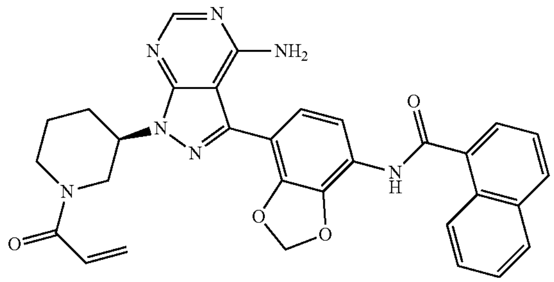
I-22
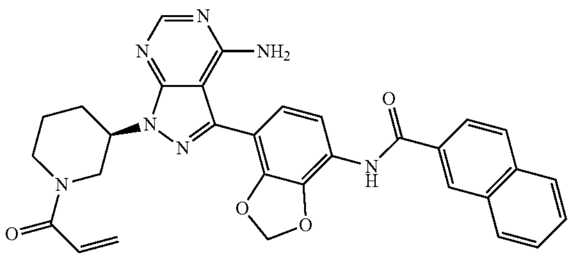
I-31
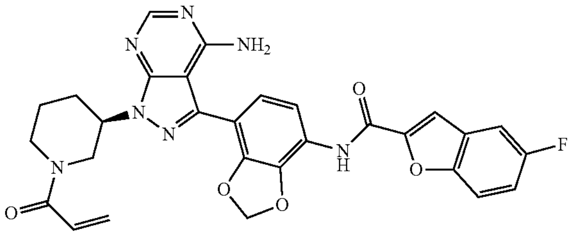
I-32
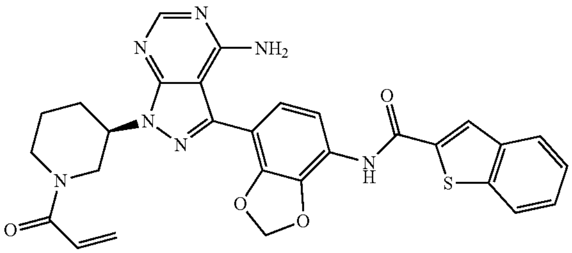
I-33
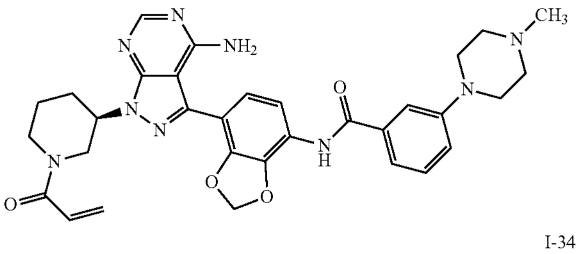
I-34
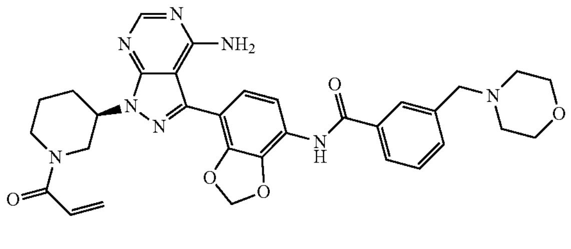

The pharmaceutically acceptable salt of the compound in the invention is the acid addition salt of the compound of general formula (I), wherein the acids used to form the salt are: Hydrogen chloride, hydrogen bromide, as well as the following acids: sulfuric, carbonic, oxalic, citric, succinic, tartaric, phosphoric, lactic, pyruvic, acetic, maleic, methanesulfonic, benzenesulfonic, p-toluenesulfonic, or ferulic acids.

The compound of general formula (I) of the invention can be prepared by the following methods:

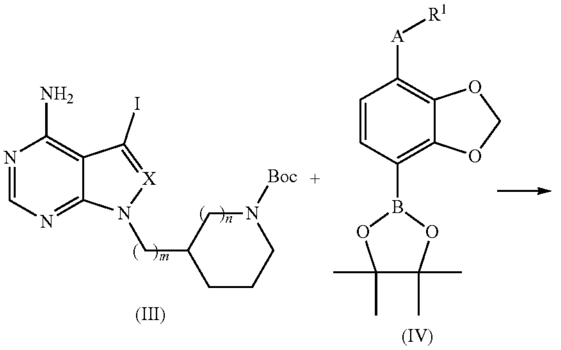

(III)

(IV)

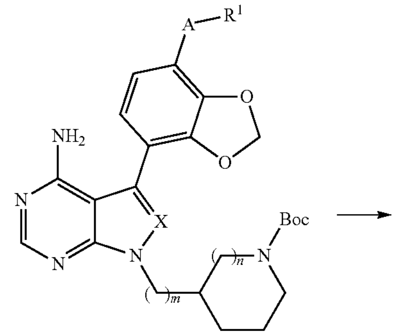

(V)

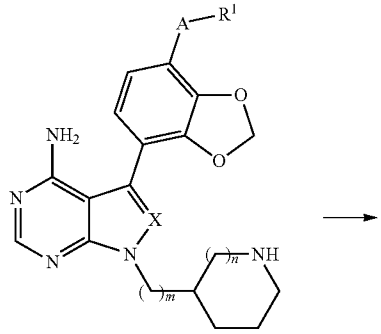

(VI)

-continued

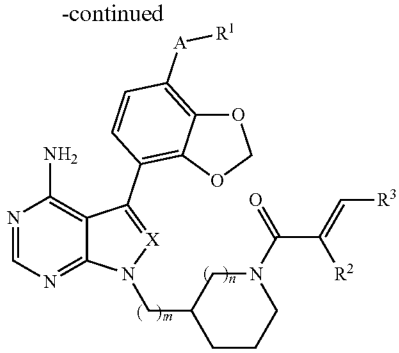

(I)

where the definitions of $R^1$, $R^2$, $R^3$, X, A, m and n are the same as before;

Compound (V) is prepared by a Suzuki coupling reaction between compounds (III) and (IV); the solvent used is selected from toluene, N, N-dimethylformamide (DMF), ethylene glycol dimethyl ether, 1,4-dioxane, tetrahydrofuran, methanol, ethanol, acetonitrile, acetone, water or a mixed solvent composed of any two of the above solvents, preferably including ethylene glycol dimethyl ether. The base used is selected from sodium ethylate, sodium acetate, potassium acetate, potassium phosphate, sodium hydroxide, potassium hydroxide, potassium carbonate, sodium carbonate or triethylamine, preferably sodium carbonate or potassium carbonate; the catalyst used is selected from tetrakis (triphenylphosphine) palladium (Pd $(PPh_3)_4$), [1,1'-bis (diphenylphosphino)ferrocene]palladium dichloride (Pd(dppf) $Cl_2$), bis(triphenylphosphino)palladium dichloride (Pd $(PPh_3)_2Cl_2$), palladium acetate (Pd $(OAc)_2$) or (1,1'-bis (diphenylphosphino)ferrocene)nickel dichloride ($NiCl_2$ (dppf)), preferably Pd(dppf)$Cl_2$. The reaction temperature is selected from room temperature to 120° C., and preferably 70-100° C.

Compound (VI) is prepared from compound (V) by removing the tert-butoxycarbonyl (Boc) protecting group, using a reagent selected from trifluoroacetic acid, concentrated hydrochloric acid, hydrogen chloride/ethyl acetate solution or hydrogen chloride/methanol solution, preferably trifluoroacetic acid or hydrogen chloride/ethyl acetate solution. The reaction solvent is selected from acetone, dichloromethane, ethyl acetate, 1,4-dioxane or acetonitrile, preferably ethyl acetate or dichloromethane.

Compound (I) is prepared by reacting compound (VI) with the corresponding acid chloride; the acid-binding agent used is selected from triethylamine, pyridine, N,N-diisopropylethylamine, 4-dimethylaminopyridine, potassium carbonate or sodium carbonate, preferably triethylamine. The solvent used is selected from dichloromethane, tetrahydrofuran, 1,4-dioxane, ethyl acetate, acetone, toluene or DMF, preferably dichloromethane.

Compound (I) can also be prepared by reacting compound (VI) with the corresponding acid in the presence of a condensing agent selected from N, N'-carbonyldiimidazole (CDI), 1-(3-dimethylaminopropyl)-3-ethylcarbodiimide hydrochloride (EDCI)/1-hydroxybenzotriazole (HOBt) or dicyclohexylcarbodiimide (DCC)/4-dimethylaminopyridine (DMAP), while EDCI/HOBt is preferred.

When A represents —NHCO—, m represents 0, n represents 1, $R^2$, $R^3$ represents H, and when the C atom at the 3-position of piperidine is in the R configuration, the compound of the general formula (II) in the invention can be prepared by the following method:

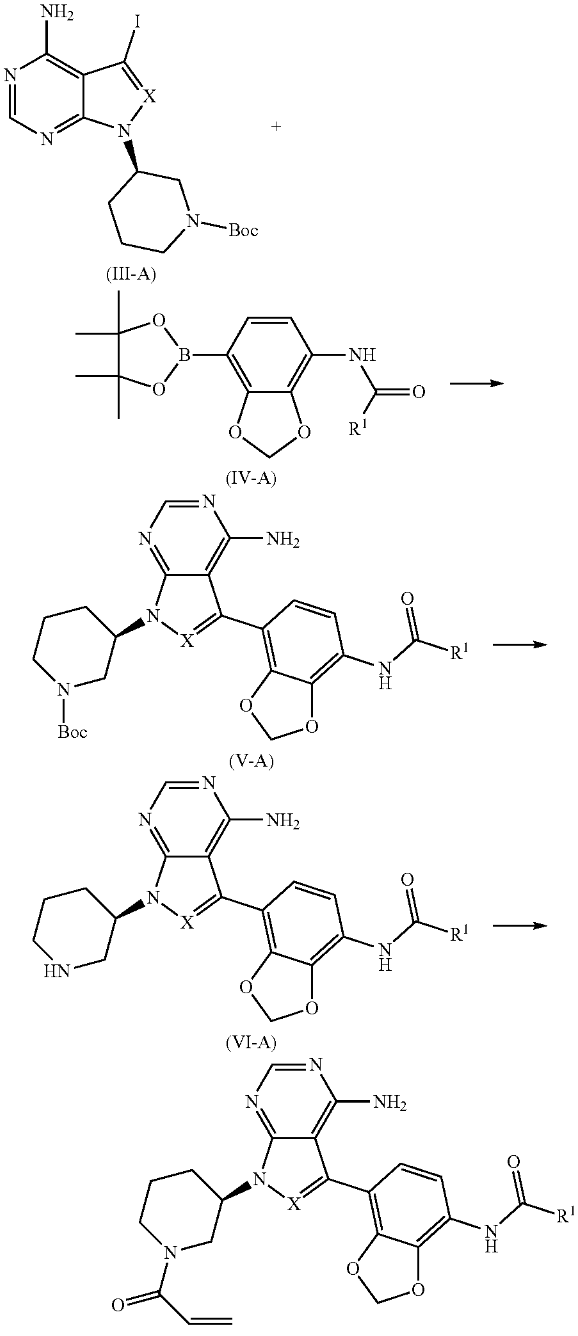

(III-A) (IV-A) (V-A) (VI-A) (II)

where the definitions of $R^1$ and X are the same as before.

Compound (V-A) is prepared by the Suzuki coupling reaction between compounds (III-A) and (IV-A). The solvent used is selected from toluene, DMF, ethylene glycol dimethyl ether, 1,4-dioxane, tetrahydrofuran, methanol, ethanol, acetonitrile, acetone, water or a mixed solvent of any two of the above solvents, preferably ethylene glycol dimethyl ether. The base used is selected from sodium ethylate, sodium acetate, potassium acetate, potassium phosphate, sodium hydroxide, hydrogen potassium oxide, potassium bicarbonate, potassium carbonate, sodium carbonate or triethylamine, preferably sodium carbonate or potassium carbonate. The catalyst used is selected from $Pd(PPh_3)_4$, $Pd(dppf)Cl_2$, $Pd(PPh_3)_2Cl_2$, $Pd(OAc)_2$ or $NiCl_2(dppf)$, preferably $Pd(dppf)Cl_2$. The reaction temperature is selected from 25-120° C., preferably 70-100° C. The reaction time is selected from 2-24 hours, preferably 12-18 hours.

Compound (VI-A) is prepared from compound (V-A) by removing the Boc protecting group using a reagent selected from trifluoroacetic acid, concentrated hydrochloric acid, hydrogen chloride/ethyl acetate solution or hydrogen chloride/methanol solution, preferably hydrogen chloride/ethyl acetate solution. The reaction solvent is selected from acetone, dichloromethane, ethyl acetate, 1,4-dioxane or acetonitrile, preferably ethyl acetate or dichloromethane.

Compound (II) is prepared by reacting compound (VI-A) with acryloyl chloride. The acid-binding agent used is selected from triethylamine, pyridine, N,N-diisopropylethylamine, 4-dimethylaminopyridine, potassium carbonate or sodium carbonate, preferably triethylamine. The solvent used is selected from dichloromethane, tetrahydrofuran, acetone, toluene or DMF, preferably dichloromethane.

Compound (II) can also be prepared by reacting compound (VI-A) with acrylic acid in the presence of a condensing agent selected from CDI, EDCI/HOBt or DCC/DMAP, preferably EDCI/HOBt.

Intermediate (III) can be prepared by the following method:

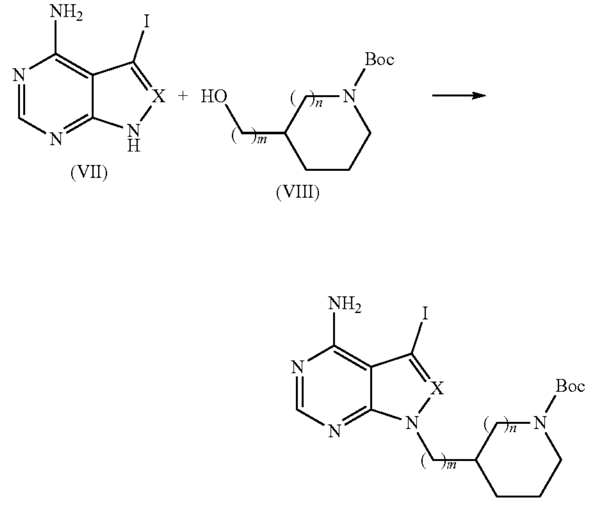

(VII) (VIII) (III)

where the definitions of X, m and n are the same as before.

Compound (III) is prepared by the Mitsunobu reaction of compounds (VII) and (VIII). The phosphine ligand used is selected from triphenylphosphine ($PPh_3$) or tri-n-butylphosphine ($n-Bu_3P$), preferably triphenylphosphine. The azo reagent used is selected from diethyl azodicarbonate (DEAD), diisopropyl azodicarbonate (DIAD) or N,N,N',N'-tetramethylazodicarbonamide (TMAD), preferably DIAD. The solvent used is selected from tetrahydrofuran, 1,4-dioxane, diethyl ether, dichloromethane, toluene, acetonitrile or DMF, preferably tetrahydrofuran.

Intermediate (IV) can be prepared by the following methods:

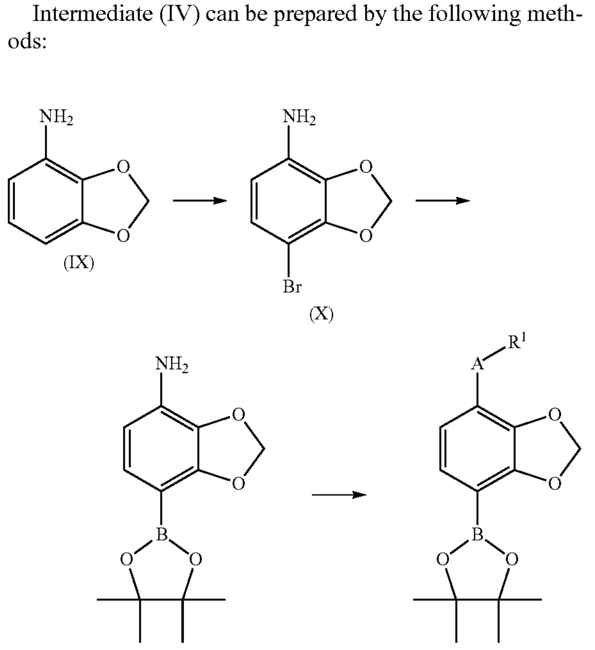

(IX) (X) (XI) (IV)

where A is selected from —NHCO—, —NHCOCH$_2$— or —NHSO$_2$—, and R$^1$ is as defined above.

Benzo[d][1,3]dioxo heterocyclopenten-4-amine (IX) is dissolved in DMF, and N-bromosuccinimide (NBS) is added for bromination to obtain 7-bromo benzo[d][1,3]dioxo heterocyclopenten-4-amine (X).

Compound (X) and biboronic acid pinacol ester are dissolved in 1,4-dioxane, and react in the presence of a catalyst, Pd(dppf)Cl$_2$, and potassium acetate to obtain 7-(4,4,5,5-tetra methyl-1,3,2-dioxaborolan-2-)benzo[d][1,3]dioxo heterocyclopenten-4-amine (XI).

The intermediate (IV) is prepared by reacting compound (XI) with the corresponding acid chloride. The acid-binding agent used is selected from triethylamine, pyridine, N,N-diisopropylethylamine, 4-dimethylaminopyridine, potassium carbonate or sodium carbonate, preferably N,N-diisopropylethylamine or triethylamine. The solvent used is selected from dichloromethane, tetrahydrofuran, 1,4-dioxane, ethyl acetate, acetone, toluene or DMF, preferably dichloromethane.

The invention also discloses a pharmaceutical composition, which contains the compound of general formula (I) or its pharmaceutically acceptable salt thereof and a pharmaceutically acceptable carrier. The compound can be made into common pharmaceutical preparations by adding pharmaceutically acceptable carriers, such as tablets, capsules, syrups, suspensions, and injections as well; spices, sweeteners, liquid or solid fillers or diluents can be added as medical excipients.

The pharmaceutical composition of the invention can be administered by methods known to those skilled in the art, such as oral, rectal, sublingual, pulmonary, transdermal, iontophoresis, vaginal and intranasal administration. The pharmaceutical composition of the invention is preferably administered parenterally, such as by subcutaneous, intramuscular or intravenous injection. The dose varies according to the form of the preparation, the expected duration of action, and the condition of the subject to be treated. The therapeutically effective dose required for actual treatment can be determined by a doctor according to the actual situation (such as the patient's condition, body weight, etc.). For normal adults, the dose of the pharmaceutical composition of the invention based on the compound of general formula (I) may be 1 ng to 10 g per kg body weight of an adult, preferably 10 μg to 100 mg per kg body weight.

The use of the compound of general formula (I) or its stereoisomers, hydrates, solvates, crystals or pharmaceutically acceptable salts in the preparation of BTK and/or JAK3 inhibitor drugs is also protected by the invention. Correspondingly, the invention also provides a treatment method, which comprises administering a therapeutically effective amount of the compound of general formula (I) of the invention or its stereoisomer, hydrated substances, solvates, crystals or its pharmaceutically acceptable salts.

Preferably, the invention provides the compound of general formula (I) or its stereoisomer, hydrate, solvate, crystal or its pharmaceutically acceptable salt in the preparation of BTK and JAK3 dual-target inhibitor drug.

Further, the BTK and JAK3 inhibitors therein are used for the treatment of autoimmune diseases and B-cell malignancies, preferably, the autoimmune diseases include rheumatoid arthritis, psoriasis and alopecia areata, and others, and the B-cell malignancies include B-cell lymphoma and so on.

Correspondingly, the invention also provides a method for treating an autoimmune disease or a B-cell malignancy, which comprises administering a therapeutically effective dose of the compound of general formula (I) or its stereoisomer, hydrate, solvate, crystal or its pharmaceutically acceptable salt in the invention to a subject suffering from an autoimmune disease or a B-cell malignancy.

The beneficial effect of the invention is to provide 1,3-benzodioxol derivatives represented by the general formula (I). The results of pharmacological trials show that the compound (I) of the invention can produce excellent inhibition effects on both BTK and JAK3 kinases, and can be used to prepare drugs for rheumatoid arthritis caused by over-activation of BTK and JAK3 pathways. The 1,3-benzodioxol derivatives of the invention have high selectivity for inhibiting the activity of JAK3, and basically no inhibitory activity on JAK1 and JAK2. The invention also provides a highly efficient preparation method of the 1,3-benzodioxol derivatives.

DETAILED DESCRIPTION OF THE INVENTION

The present application will be described in detail below in conjunction with specific implementations.

Example 1

Synthesis of ((R)—N-(7-(1-(1-acryloylpiperidin-3)-4-amino-1H-pyrazolo[3,4-d]pyrimidin-3-yl)benzo[d][1,3]dioxo heterocyclopenten-)benzamide (I-1)

Synthesis of (R)-3-(4-amino-3-iodo-1H-pyrazolo[3,4-d]pyrimidin-1)piperidine-1-tert-butyl formate (III-1)

4-Amino-3-iodo-1H-pyrazolo[3,4-d]pyrimidine (VII-1) (1.80 g, 6.90 mmol), (S)-1-tert-butoxycarbonyl-3-hydroxy piperidine (VIII-1) (2.78 g, 13.79 mmol), PPh$_3$ (3.61 g, 13.79 mmol), and anhydrous THF (100 mL) were added to a 250 mL three-necked flask under nitrogen protection. The mixture was stirred for 30 minutes under ice bath, and DIAD (2.40 g, 13.79 mmol) was added; the mixture was reacted at room temperature for 18 hours. Next, THF was distilled off under reduced pressure, the residue was dissolved in ethyl acetate (100 mL), and washed successively with saturated sodium carbonate (30 mL×3), water (30 mL×3), saturated sodium chloride (30 mL×3), and was dried by anhydrous $Na_2SO_4$. After suction filtration, the filtrate was evaporated to remove the solvent under reduced pressure to obtain a yellow oil, which was separated by column chromatography (eluent: Dichloromethane:Methanol=150-90:1), 2.06 g of white solid was obtained. The yield was 67.2%, m.p. at 178-180° C. $^1$H-NMR (300 MHz, $CDCl_3$) δ (ppm): 8.34 (s, 1H, ArH), 6.27 (s, 2H, $NH_2$), 4.85-4.66 (m, 1H, $CHC\underline{H_2}N$), 4.36-4.00 (m, 2H, $C\underline{H}CH_2N$), 3.47-3.21 (m, 1H, $CHCH_2CH_2C\underline{H_2}N$), 2.92-2.72 (m, 1H, $CHCH_2CH_2CH_2N$), 2.28-2.01 (m, 2H, $CHC\underline{H_2}CH_2CH_2N$), 1.97-1.79 (m, 1H, $CHC\underline{H_2}CH_2CH_2N$), 1.76-1.57 (m, 1H, $CHCH_2C\underline{H_2}CH_2N$), 1.45 (s, 9H, NBoc).

Synthesis of 7-bromobenzo[d][1,3]dioxo heterocyclopenten-4-amine (X)

Mix benzo[d][1,3]dioxo heterocyclopenten-4-amine (IX) (1.24 g, 9.04 mmol) and DMF (30 mL); then, stir the mixture to dissolve and cool to −30° C. Next, NBS (1.69 g, 9.50 mmol) was added in batches; after the addition was complete, the mixture was incubated and reacted for 1 hour. Water (60 mL) was added, the mixture was extracted with ethyl acetate (15 mL×3), the organic phase was washed successively with water (10 mL×3) and saturated sodium chloride solution (10 mL×3), and then dried over anhydrous sodium sulfate. After suction filtration, the filtrate was evaporated to dryness under reduced pressure, and the residue was subjected to column chromatography (eluent: Petroleum ether:Ethyl acetate=30-10:1) to obtain 1.01 g of white solid with a yield of 51.7%, m.p. at 99-100° C. $^1$H-NMR (300 MHz, $CDCl_3$) δ (ppm): 6.80 (d, J=8.67 Hz, 1H, ArH), 6.23 (d, J=8.67 Hz, 1H, ArH), 6.02 (s, 2H, $OCH_2O$), 3.58 (s, 2H, $NH_2$).

Synthesis of 7-(4,4,5,5-Tetramethyl-1,3,2-dioxaborolan-2-yl)benzo[d][1,3]dioxo heterocyclopenten-4-amine (XI)

Compound X (3.14 g, 14.54 mmol), bis(pinacolato)diboron (7.39 g, 29.07 mmol), $Pd(dppf)Cl_2$ (0.53 g, 0.73 mmol), potassium acetate (4.28 g, 43.62 mmol) and 1,4-dioxane (25 mL) were mixed under $N_2$ protection. Next, the temperature was raised to 95° C. for reaction for 12 hours. Suction filtration was completed using diatomaceous earth. The filtrate was distilled off the solvent under reduced pressure, and was then dissolved in ethyl acetate (20 mL), washed with water (10 mL×3) and saturated sodium chloride solution (10 mL×3) successively. Next, the filtrate was dried over anhydrous sodium sulfate; then, suction filtration was used and the filtrate was evaporated to dryness under reduced pressure. The residue was subjected to column chromatography (eluent: Petroleum ether:Dichloromethane=1:5-10) to obtain 2.70 g of white solid with a yield of 70.6%, mp. 84-86° C. $^1$H-NMR (300 MHz, $CDCl_3$) δ (ppm): 7.09 (d, J=8.16 Hz, 1H, ArH), 6.31 (d, J=8.19 Hz, 1H, ArH), 5.99 (s, 2H, $OCH_2O$), 3.71 (br, 2H, $NH_2$), 1.34 (s, 12H, $4CH_3$).

Synthesis of N-(7-(4,4,5,5-tetramethyl-1,3,2-dioxaborolan-2-yl)benzo[d][1,3]dioxo heterocyclopenten-4-)benzamide (IV-1)

Compound XI (0.56 g, 2.14 mmol) was dissolved in dichloromethane (10 mL); then, N,N-diisopropylethylamine (0.83 g, 6.42 mmol) was added, and benzoyl chloride (0.45 g, 3.21 mmol) in dichloromethane solution was added dropwise, after which the mixture was reacted at room temperature for 30 min. The reaction solution was washed successively with 1 mol/L hydrochloric acid (10 mL×3), saturated sodium bicarbonate solution (10 mL×3), water (10 mL×3) and saturated sodium chloride solution (10 mL×3), and was then dried over anhydrous $Na_2SO_4$. After suction filtration, the filtrate was evaporated to dryness under reduced pressure, and the residue was subjected to column chromatography (eluent: Petroleum ether:Dichloromethane=1:1-8) to obtain 409 mg of white solid with a yield of 52.1%, m.p. at 202-204° C. $^1$H-NMR (300 MHz, $CDCl_3$) δ (ppm): 7.89-7.88 (m, 4H, ArH), 7.57-7.47 (m, 3H, ArH, NH), 7.29 (d, J=8.73 Hz, 1H, ArH), 6.07 (s, 2H, $OCH_2O$), 1.36 (s, 12H, $4CH_3$).

Synthesis of (R)-3-(4-amino-3-(7-benzamidobenzo[d][1,3]dioxo heterocyclopenten-4)-1H-pyrazolo[3,4-d]pyrimidin-1-)piperidine-1-tert-butyl formate (V-1)

Add compound III-1 (1.50 g, 3.38 mmol) and IV-1 (1.49 g, 4.05 mmol) into a 100 mL single-neck flask. Next, add 2 mol/L sodium carbonate solution (3.38 mL), $Pd(dppf)Cl_2$ (0.12 g, 0.17 mmol) and ethylene glycol dimethyl ether (40 mL) under nitrogen protection, react the mixture at 85° C. for 17 hours. Cool to room temperature, suction filter through diatomaceous earth, concentrate the filtrate under reduced pressure, then dissolve it in ethyl acetate (40 mL), wash with water (10 mL×3), and then saturated sodium chloride (10 mL×3), and it was concentrated under reduced pressure to obtain 2.56 g crude. Column chromatography (eluent: Dichloromethane:Methanol=100-70:1), after separation 926 mg of light-yellow solid was obtained with a yield of 49.2%, m.p. at 112-114° C. $^1$H-NMR (300 MHz, $CDCl_3$+$D_2O$) δ (ppm): 8.36 (s, 1H, ArH), 8.05-7.98 (m, 1H, ArH), 7.92 (d, J=7.23 Hz, 2H, ArH), 7.64-7.49 (m, 3H, ArH), 7.15 (d, J=8.19 Hz, 1H, ArH), 6.13 (s, 2H, $OCH_2O$), 4.92-4.79 (m, 1H, $CHC\underline{H_2}NBoc$), 4.42-4.23 (m, 1H, $C\underline{H}CH_2NBoc$), 3.57-3.28 (m, 2H, $C\underline{H_2}NC\underline{H_2}$), 2.92-2.76 (m, 1H, $NC\underline{H_2}CH_2$), 2.32-2.16 (m, 2H, $NCH_2CHC\underline{H_2}$), 1.93-1.81 (m, 2H, $NCH_2C\underline{H_2}$), 1.45 (s, 9H, NBoc).

Synthesis of (R)—N-(7-(4-amino-1-(piperidin-3-)-1H-pyrazolo[3,4-d]pyrimidin-3-)benzo[d][1,3]dioxo heterocyclopenten-4-)benzamide (VI-1)

Compound V-1 (0.93 g, 1.66 mmol) was dissolved in ethyl acetate (6 mL); next, a saturated solution of hydrogen chloride in ethyl acetate (10 mL) was added and the mixture was stirred at room temperature for 4 hours during which a large amount of solids precipitated out. Add 20 mL of water, separate the layers, wash the aqueous layer twice with ethyl acetate, adjust the pH to 8-9 with 1 mol/L NaOH, a solid then precipitated, filter it with suction, and dry it to obtain 721 mg of a light-yellow solid with a yield of 94.8%. It was directly submitted to the next step without further purification.

Synthesis of (R)—N-(7-(1-(1-acryloylpiperidin-3-yl)-4-amino-1H-pyrazolo[3,4-d]pyrimidin-3-)benzo[d][1,3]dioxo heterocyclopenten-4-)benzamide (I-1)

Compound VI-1 (93 mg, 0.20 mmol) was dissolved in 5 mL of anhydrous dichloromethane. Next, triethylamine (31 mg, 0.30 mmol) was added, and the anhydrous dichloromethane solution of acryloyl chloride (22 mg, 0.24 mmol) was added dropwise under ice bath; the dropwise addition was completed, and the mixture was stirred at room temperature for 3.5 hours. Wash with water (10 mL×3) and saturated sodium chloride solution (10 mL×3), and it was concentrated under reduced pressure to obtain a crude product. Residue column chromatography (eluent: Dichloromethane:Methanol=100-35:1), and 77 mg of white solid was isolated with a yield of 74.0%, m.p. at 141-142.5° C. $^1$H-NMR (300 MHz, $CDCl_3$) δ (ppm): 8.39 (s, 1H, ArH), 8.35-8.25 (m, 1H, NH), 7.93 (d, J=7.26 Hz, 2H, ArH), 7.86-7.76 (m, 1H, ArH), 7.60-7.44 (m, 3H, ArH), 7.13-7.03 (m, 1H, ArH), 6.67-6.52 (m, 1H, $CH{=}CH_2$), 6.34-6.18 (m, 2H, $CH{=}CH_2$, $NH_2$), 6.09 (s, 2H, $OCH_2O$), 5.75-5.60 (m, 1H, $CH{=}CH_2$), 4.93-4.74 (m, 1.5H, $NCH_2CH$), 4.65-4.51 (m, 0.5H, $NCH_2CH$), 4.27-4.14 (m, 0.5H, $NCH_2CH$), 4.08-3.94 (m, 0.5H, $NCH_2CH$), 3.85-3.68 (m, 0.5H, $NCH_2CH_2$), 3.40-3.26 (m, 0.5H, $NCH_2CH_2$), 3.24-3.08 (m, 0.5H, $NCH_2CH_2$), 2.92-2.85 (m, 0.5H, $NCH_2CH_2$), 2.81 (s, 1H, $NH_2$), 2.46-2.30 (m, 1H, $NCH_2CHCH_2$), 2.29-2.18 (m, 1H, $NCH_2CHCH_2$), 2.06-1.91 (m, 1H, $NCH_2CH_2$), 1.79-1.61 (m, 1H, $NCH_2CH_2$). HRMS (ESI): m/z $[M+H]^+$. Calcd for $C_{27}H_{26}N_7O_4$: 512.2046; found: 512.2045.

Example 2

Synthesis of (R)—N-(7-(1-(1-acryloylpiperidin-3)-4-amino-1H-pyrazolo[3,4-d]pyrimidin-3-yl)benzo[d][1,3]dioxo heterocyclopenten-4-)thiophene-2-formamide (I-2)

Synthesis of N-(7-(4,4,5,5-tetramethyl-1,3,2-dioxaborolan-2-)benzo[d][1,3]dioxo heterocyclopenten-4-)thiophene-2-formamide (IV-2)

Thiophene-2-formic acid (0.73 g, 5.70 mmol) was dissolved in anhydrous dichloromethane (12 mL), 3 drops of DMF was added, and the anhydrous dichloromethane solution of oxalyl chloride (1.09 g, 8.55 mmol) was added dropwise under ice bath. After drop addition, stir at room temperature. TLC (petroleum ether:Ethyl acetate=3:1) was used for monitoring. After the reaction of the raw materials was complete, the solvent was removed under reduced pressure, and anhydrous dichloromethane (15 mL) was added to dissolve the residue for use.

Add compound XI (1.00 g, 3.80 mmol) and dichloromethane (20 mL) to a 50 mL eggplant-shaped flask, stir to dissolve, add N,N-diisopropylethylamine (1.47 g, 11.40 mmol), and under ice-bath the above-mentioned oxalyl chloride was added dropwise, and the mixture was reacted at room temperature for 6 hours. The organic phase was washed successively with 1 mol/L hydrochloric acid (10 mL×3), water (10 mL), saturated sodium bicarbonate solution (10 mL), saturated sodium chloride solution (10 mL×3), and was dried over anhydrous sodium sulfate. Suction filtration, and the filtrate was concentrated under reduced pressure to obtain a light-yellow solid. Petroleum ether:ethyl acetate was beaten at a ratio of 8:1 (1 g/6 mL) to obtain 1.25 g of white solid with a yield of 88.1%, which was directly used in the next step without further purification.

Synthesis of (R)-3-(4-amino-3-(7-(thiophene-2-carboxamido)benzo[d][1,3]dioxo heterocyclopenten-4)-1H-pyrazolo[3,4-d]pyrimidin-1-)piperidine-1-tert-butyl formate (V-2)

Using compound III-1 (0.90 g, 2.03 mmol) and IV-2 (0.91 g, 2.16 mmol) as raw materials, the operation process was the same as that of compound V-1 to obtain 583 mg of light-yellow solid with a yield of 51.1%, m.p. at 142-144° C. $^1$H-NMR (300 MHz, $CDCl_3$) δ (ppm): 8.35 (s, 1H, ArH), 7.94-7.87 (m, 2H, ArH, NH), 7.69 (d, J=3.66 Hz, 1H, ArH), 7.60 (d, J=5.01 Hz, 1H, ArH), 7.20-7.08 (m, 2H, ArH), 6.12 (s, 2H, $OCH_2O$), 5.93 (br, 2H, $NH_2$), 4.93-4.78 (m, 1H, $CHCH_2NBoc$), 4.46-4.07 (m, 2H, $CHCH_2NBoc$), 3.56-3.29 (m, 1H, $NCH_2CH_2$), 2.94-2.75 (m, 1H, $NCH_2CH_2$), 2.35-2.13 (m, 2H, $NCH_2CHCH_2$), 1.98-1.82 (m, 1H, $NCH_2CH_2$), 1.77-1.59 (m, 1H, $NCH_2CH_2$), 1.45 (s, 9H, NBoc).

Synthesis of (R)—N-(7-(4-amino-1-(piperidin-3)-1H-pyrazolo[3,4-d]pyrimidin-3-)benzo[d][1,3]dioxo heterocyclopenten-4)-thiophene-2-formamide (VI-2)

Using compound V-2 (400 mg, 0.71 mmol) as the starting material, the procedure was the same as that of compound VI-1 to obtain 329 mg of light-yellow solid, which was directly used in the next step without further purification.

Synthesis of (R)—N-(7-(1-(1-acryloylpiperidin-3)-4-amino-1H-pyrazolo[3,4-d]pyrimidin-3-yl)benzo[d][1,3]dioxo heterocyclopenten-4-)thiophene-2-formamide (I-2)

Using compound VI-2 (300 mg, 0.65 mmol) and acryloyl chloride (64 mg, 0.71 mmol) as raw materials, the procedure was the same as that of compound I-1 to obtain 131 mg of white solid with a yield of 39.1%, m.p. at 140-142° C. $^1$H-NMR (300 MHz, $CDCl_3$) δ (ppm): 8.37 (s, 1H, ArH), 8.02 (s, 1H, NH), 7.89 (d, J=7.98 Hz, 1H, ArH), 7.73 (d, J=3.27 Hz, 1H, ArH), 7.62 (d, J=4.74 Hz, 1H, ArH), 7.18 (d, J=3.60 Hz, 1H, ArH), 7.12 (d, J=8.70 Hz, 1H, ArH), 6.72-6.54 (m, 1H, $CH{=}CH_2$), 6.39-6.25 (m, 1H, $CH{=}CH_2$), 6.14 (s, 2H, $OCH_2O$), 5.96 (s, 1H, $NH_2$), 5.79-5.63 (m, 1H, $CH{=}CH_2$), 4.99-4.82 (m, 1.5H, $NCH_2CH$), 4.71-4.58 (m, 0.5H, $NCH_2CH$), 4.32-4.18 (m, 0.5H, $NCH_2CH$), 4.12-3.99 (m, 0.5H, $NCH_2CH$), 3.89-3.73 (m, 0.5H, $NCH_2CH_2$), 3.47-3.32 (m, 0.5H, $NCH_2CH_2$), 3.30-3.14 (m, 0.5H, $NCH_2CH_2$), 2.97-2.79 (m, 0.5H, $NCH_2CH_2$), 2.49-2.34 (m, 1H, $NCH_2CHCH_2$), 2.33-2.23 (m, 1H, $NCH_2CHCH_2$), 2.20 (s, 1H, $NH_2$), 2.07-1.96 (m, 1H, $NCH_2CH_2$), 1.83-1.67 (m, 1H, $NCH_2CH_2$); HRMS (ESI): m/z $[M+H]^+$. Calcd for $C_{25}H_{24}N_7O_4S$: 518.1610; found: 518.1611.

Example 3

Synthesis of (R)—N-(7-(1-(1-acryloylpiperidin-3-yl)-4-amino-1H-pyrazolo[3,4-d]pyrimidin-3-)benzo[d][1,3]dioxo heterocyclopenten-4)-1H-pyrrole-2-formamide (I-3)

Synthesis of N-(7-(4,4,5,5-tetramethyl-1,3,2-dioxaborolan-2-yl)benzo[d][1,3]dioxo heterocyclopenten-4)-1H-pyrrole-formamide (IV-3)

Using compound XI (1.00 g, 3.80 mmol) and pyrrole-2-carboxylic acid (0.63 g, 5.70 mmol) as raw materials, the operation process was the same as that of compound IV-2 to obtain 1.17 g of white solid with a yield of 86.4%, which was directly fed into next step without further purification.

Synthesis of (R)-3-(3-(7-(1H-pyrrole-2-formamide)benzo[d][1,3]dioxo heterocyclopenten-4)-4-amino-1H-pyrazolo[3,4-d]pyrimidin-1-)piperidine-1-tert-butyl formate (V-3)

Using compound III-1 (0.90 g, 2.03 mmol) and IV-3 (1.36 g, 3.85 mmol) as raw materials, the operation process was the same as that of compound V-1 to obtain 550 mg of light-yellow solid with a yield of 49.5%, m.p. at 138-140° C. $^1$H-NMR (400 MHz, $CDCl_3$) δ (ppm): 11.67 (s, 1H, NH), 8.42 (s, 1H, ArH), 7.77 (d, J=8.52 Hz, 1H, ArH), 7.70 (s, 1H, NH), 7.15-7.10 (m, 1H, ArH), 7.08 (d, J=8.60 Hz, 1H, ArH), 6.87-6.82 (m, 1H, ArH), 6.38-6.31 (m, 1H, ArH), 6.11 (s, 2H, $OCH_2O$), 5.30 (s, 1H, $NH_2$), 4.92-4.78 (m, 1H, $CHCH_2NBoc$), 4.50-4.24 (m, 1H, $CHCH_2NBoc$), 4.24-4.03 (m, 1H, $CHCH_2NBoc$), 3.58-3.29 (m, 1H, $NCH_2CH_2$), 2.91-2.75 (m, 1H, $NCH_2CH_2$), 2.36-2.16 (m, 3H, $NCH_2CHCH_2$, $NH_2$), 1.96-1.82 (m, 1H, $NCH_2CH_2$), 1.78-1.63 (m, 1H, $NCH_2CH_2$), 1.45 (s, 9H, NBoc).

Synthesis of (R)—N-(7-(4-amino-1-(piperidin-3)-1H-pyrazolo[3,4-d]pyrimidin-3-)benzo[d][1,3]dioxo heterocyclopenten-4)-1H-pyrrole-2-formamide (VI-3)

Using compound V-3 (450 mg, 0.82 mmol) as the starting material, the procedure was the same as that of compound VI-1 to obtain 383 mg of light-yellow solid, which was directly used in the next step without further purification.

Synthesis of (R)—N-(7-(1-(1-acryloylpiperidin-3-yl)-4-amino-1H-pyrazolo[3,4-d]pyrimidin-3-)benzo[d][1,3]dioxo heterocyclopenten-4)-1H-pyrrole-2-formamide (I-3)

Using compound VI-3 (360 mg, 0.81 mmol) and acryloyl chloride (77 mg, 0.85 mmol) as raw materials, the procedure was the same as that of compound I-1 to obtain 212 mg of white solid with a yield of 52.5%, m.p. at 156-158° C. $^1$H-NMR (300 MHz, $CDCl_3+D_2O$) δ (ppm): 8.40 (s, 1H, ArH), 7.80-7.60 (m, 1H, ArH), 7.18-6.99 (m, 2H, ArH), 6.94-6.81 (m, 1H, ArH), 6.70-6.52 (m, 1H, $CH{=}CH_2$), 6.43-6.22 (m, 2H, ArH, $CH{=}CH_2$), 6.09 (s, 2H, $OCH_2O$), 5.80-5.60 (m, 1H, $CH{=}CH_2$), 5.07-4.54 (m, 4H, $NCH_2CH$, $NH_2$), 4.31-4.15 (m, 0.5H, $NCH_2CH$), 4.10-3.93 (m, 0.5H, $NCH_2CH$), 3.87-3.65 (m, 0.5H, $NCH_2CH_2$), 3.46-3.30 (m, 0.5H, $NCH_2CH_2$), 3.26-3.11 (m, 0.5H, $NCH_2CH_2$), 2.95-2.76 (m, 0.5H, $NCH_2CH_2$), 2.48-2.14 (m, 2H, $NCH_2CHCH_2$), 2.05-1.89 (m, 1H, $NCH_2CH_2$), 1.83-1.60 (m, 1H, $NCH_2CH_2$); HRMS (ESI): m/z $[M+H]^+$. Calcd for $C_{25}H_{25}N_8O_4$: 501.1999; found: 501.2003.

Example 4

Synthesis of (R)—N-(7-(1-(1-acryloylpiperidin-3)-4-amino-1H-pyrazolo[3,4-d]pyrimidin-3-yl)benzo[d][1,3]dioxo heterocyclopenten-4)pyridine-2-formamide (I-4)

Synthesis of N-(7-(4,4,5,5-tetramethyl-1,3,2-dioxaborolan-2-yl)benzo[d][1,3]dioxo heterocyclopenten-4)-pyridine-2-formamide (IV-4)

Using compound XI (0.70 g, 2.66 mmol) and pyridine-2-formyl chloride hydrochloride (0.57 g, 3.19 mmol) as raw materials, the operation process was the same as that of compound IV-1 to obtain 612 mg of off-white solid with a yield of 62.5%, m.p. at 190-192° C. $^1$H-NMR (300 MHz, $CDCl_3$) ((ppm): 10.11 (s, 1H, NH), 8.70-8.66 (m, 1H, ArH), 8.29 (d, J=7.65 Hz, 1H, ArH), 8.00 (d, J=8.43 Hz, 1H, ArH), 7.93 (t, J=7.56 Hz, 1H, ArH), 7.54-7.44 (m, 1H, ArH), 7.30 (d, J=8.55 Hz, 1H, ArH), 6.11 (s, 2H, $OCH_2O$), 1.37 (s, 12H, $4CH_3$).

Synthesis of (R)-3-(4-amino-3-(7-(pyridine-2-formamidyl)benzo[d][1,3]dioxo heterocyclopenten-4)-1H-pyrazolo[3,4-d]pyrimidin-1-)piperidine-1-tert-butyl formate (V-4)

Using compound III-1 (0.80 g, 1.80 mmol) and compound IV-4 (0.80 g, 2.16 mmol) as raw materials, the operation process was the same as that of compound V-1 to obtain 476 mg of a light-yellow solid with a yield of 47.4%, m.p. at 118-120° C. $^1$H-NMR (300 MHz, $CDCl_3$) δ (ppm): 10.17 (s, 1H, NH), 8.70-8.66 (m, 1H, ArH), 8.39 (s, 1H, ArH), 8.33 (d, J=7.77 Hz, 1H, ArH), 8.17 (d, J=8.70 Hz, 1H, ArH), 7.96 (td, $J_1$=7.74 Hz, $J_2$=1.65 Hz, 1H, ArH), 7.58-7.51 (m, 1H, ArH), 7.18 (d, J=8.70 Hz, 1H, ArH), 6.18 (s, 2H, $OCH_2O$), 5.79 (s, 2H, $NH_2$), 4.94-4.81 (m, 1H, $CHCH_2NBoc$), 4.43-4.27 (m, 1H, $CHCH_2NBoc$), 4.23-4.10 (m, 1H, $CHCH_2NBoc$), 3.52-3.39 (m, 1H, $NCH_2CH_2$), 2.94-2.79 (m, 1H, $NCH_2CH_2$), 2.34-2.27 (m, 1H, $NCH_2CHCH_2$), 2.26-2.20 (m, 1H, $NCH_2CHCH_2$), 1.98-1.90 (m, 2H, $NCH_2CH_2$), 1.47 (s, 9H, NBoc).

Synthesis of (R)—N-(7-(4-amino-1-(piperidin-3)-1H-pyrazolo[3,4-d]pyrimidin-3-)benzo[d][1,3]dioxo heterocyclopenten-4-)pyridine-2-formamide (VI-4)

Compound V-4 (0.40 g, 0.72 mmol) was dissolved in anhydrous dichloromethane (5 mL), add trifluoroacetic acid (5 mL), and it was stirred at room temperature for 10 hours. Evaporate the solvent under reduced pressure, dissolve the residue in ethyl acetate, adjust the pH to 8-9 with 1 mol/L NaOH, separate the layers, extract the aqueous layer once with ethyl acetate, wash the organic layer with saturated sodium chloride (10 mL×3), then it was dried over anhydrous sodium sulfate.

After suction filtration, the filtrate was concentrated under reduced pressure to obtain 280 mg of a light-yellow product with a yield of 85.37%. It was directly submitted to the next step without further purification.

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)pyridine-2-formamide (I-4)

Compound VI-4 (230 mg, 0.50 mmol), acrylic acid (43 mg, 0.60 mmol), HOBt (102 mg, 0.75 mmol), EDCI (145 mg, 0.75 mmol) and TEA (102 mg, 1.00 mmol) were dissolved in 6 mL DMF, then stirred at room temperature for 12 h. Next, 30 mL of water was added, and it was extracted with ethyl acetate (10 mL×3), and the organic layer was sequentially washed with 1 mol/L hydrochloric acid (10 mL×3), saturated sodium carbonate (10 mL×3) and saturated sodium chloride (10 mL×3) and then was dried over anhydrous sodium sulfate. Suction filtration, and the filtrate was concentrated under reduced pressure to obtain a crude product. Column chromatography (eluent: Dichloromethane:Methanol=100-50:1) to obtain 201 mg of white solid with a yield of 78.2%, m.p. at 154-156° C. $^1$H-NMR (300 MHz, $CDCl_3$) δ (ppm): 10.11 (s, 1H, NHCO), 8.61 (s, 1H, ArH), 8.36-8.21 (m, 2H, ArH), 8.16-8.03 (m, 1H, ArH), 7.97-7.84 (m, 1H, ArH), 7.55-7.40 (m, 1H, ArH), 7.16-7.02 (m, 1H, ArH), 6.64-6.46 (m, 1H, $CH{=}CH_2$), 6.34-6.19 (m, 1H, $CH{=}CH_2$), 6.12 (s, 2H, $OCH_2O$), 5.78 (s, 1H, $NH_2$), 5.68-5.57 (m, 1H, $CH{=}CH_2$), 4.96-4.74 (m, 1.5H, $NCH_2CH$), 4.65-4.52 (m, 0.5H, $NCH_2CH$), 4.24-4.12 (m, 0.5H, $NCH_2CH$), 4.05-3.92 (m, 0.5H, $NCH_2CH$), 3.80-3.67 (m, 0.5H, $NCH_2CH_2$), 3.42-3.26 (m, 0.5H, $NCH_2CH_2$), 3.20-3.07 (m, 0.5H, $NCH_2CH_2$), 2.90-2.73 (m, 0.5H, $NCH_2CH_2$), 2.44-2.15 (m, 2H, $NCH_2CHCH_2$), 2.04-1.84 (m, 3H, $NCH_2CH_2$, $NH_2$); HRMS (ESI): m/z $[M+H]^+$. Calcd for $C_{26}H_{25}N_8O_4$: 513.1999; found: 513.1999.

Example 5

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-2-chlorobenzamide (I-5)

Synthesis of 2-Chloro-N-(7-(4,4,5,5-tetramethyl-1,3,2-dioxaborolan-2-)benzo[d][1, 3]dioxo heterocyclopenten-4-)benzamide (IV-5)

Using compound XI (0.80 g, 3.04 mmol) and o-chlorobenzoyl chloride (0.80 g, 4.56 mmol) as raw materials, the operation process was the same as that of compound IV-1 to obtain 800 mg of white solid with a yield of 65.5%, m.p. at 96-98° C. $^1H$-NMR (300 MHz, $CDCl_3$) δ (ppm): 8.16 (s, 1H, NHCO), 7.91 (d, J=8.37 Hz, 1H, ArH), 7.81 (d, J=6.57 Hz, 1H, ArH), 7.48-7.37 (m, 3H, ArH), 7.31 (d, J=8.22 Hz, 1H, ArH), 6.08 (s, 2H, $OCH_2O$), 1.39 (s, 12H, $4CH_3$).

Synthesis of (R)-3-(4-amino-3-(7-(2-chlorobenzamido)benzo[d][1,3]dioxo heterocyclopenten-4)-1H-tert-butyl-pyrazolo[3,4-d]pyrimidin-1-)piperidine-1-tert-butyl formate (V-5)

Using compound III-1 (0.65 g, 1.46 mmol) and IV-5 (0.71 g, 1.76 mmol) as raw materials, the operation process was the same as that of compound V-1 to obtain 651 mg of light-yellow solid with a yield of 75.2%, m.p. at 124-126° C. $^1H$-NMR (300 MHz, $CDCl_3$) δ (ppm): 8.36 (s, 1H, ArH), 8.16 (s, 1H, NH), 8.06 (d, J=8.58 Hz, 1H, ArH), 7.86 (d, J=6.24 Hz, 1H, ArH), 7.52-7.40 (m, 3H, ArH), 7.15 (d, J=8.70 Hz, 1H, ArH), 6.12 (s, 2H, $OCH_2O$), 5.75 (s, 2H, $NH_2$), 4.93-4.77 (m, 1H, $CHCH_2NBoc$), 4.44-4.23 (m, 1H, $CHCH_2NBoc$), 4.22-4.04 (m, 1H, $CHCH_2NBoc$), 3.54-3.35 (m, 1H, $NCH_2CH_2$), 2.91-2.76 (m, 1H, $NCH_2CH_2$), 2.32-2.18 (m, 2H, $NCH_2CHCH_2$), 1.78-1.61 (m, 2H, $NCH_2CH_2$), 1.45 (s, 9H, NBoc).

Synthesis of (R)—N-(7-(4-amino-1-(piperidin-3)-1H-pyrazolo[3,4-d]pyrimidin-3)benzo[d][1,3]dioxo heterocyclopenten-4)-2-chlorobenzamide (VI-5)

Using compound V-5 (600 mg, 1.01 mmol) as the starting material, the procedure was the same as that of compound VI-1 to obtain 524 mg of light-yellow solid, which was directly used in the next step without further purification.

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-2-chlorobenzamide (I-5)

Starting from compound VI-5 (450 mg, 0.91 mmol) and acryloyl chloride (87 mg, 0.96 mmol), the procedure was the same as that of compound I-1 to obtain 270 mg of a white solid with a yield of 54.0%, m.p. at 156.5-158° C. $^1H$-NMR (300 MHz, $CDCl_3$) δ (ppm): 8.39-8.27 (m, 2H, ArH, CONH), 8.03 (d, J=8.61 Hz, 1H, ArH), 7.83 (d, J=7.47 Hz, 1H, ArH), 7.52-7.36 (m, 3H, ArH), 7.13 (d, J=8.55 Hz, 1H, ArH), 6.68-6.52 (m, 1H, $CH{=}CH_2$), 6.34-6.22 (m, 1H, $CH{=}CH_2$), 6.12 (s, 2H, $OCH_2O$), 6.04 (s, 1H, $NH_2$), 5.76-5.61 (m, 1H, $CH{=}CH_2$), 4.95-4.79 (m, 1.5H, $NCH_2CH$), 4.70-4.56 (m, 0.5H, $NCH_2CH$), 4.28-4.16 (m, 0.5H, $NCH_2CH$), 4.09-3.96 (m, 0.5H, $NCH_2CH$), 3.84-3.70 (m, 0.5H, $NCH_2CH_2$), 3.44-3.29 (m, 0.5H, $NCH_2CH_2$), 3.25-3.11 (m, 0.5H, $NCH_2CH_2$), 2.92-2.77 (m, 0.5H, $NCH_2CH_2$), 2.52-2.19 (m, 3H, $NCH_2CHCH_2$, $NH_2$), 2.04-1.91 (m, 1H, $NCH_2CH_2$), 1.82-1.63 (m, 1H, $NCH_2CH_2$); HRMS (ESI): m/z $[M+H]^+$. Calcd for $C_{27}H_{25}ClN_7O_4$: 546.1657; found: 546.1656.

Example 6

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-3-chlorobenzamide (I-6)

Synthesis of 3-chloro-N-(7-(4,4,5,5-tetramethyl-1,3,2-dioxaborolan-2)benzo[d][1,3]dioxo heterocyclopenten-4-)benzamide (IV-6)

Using compound XI (0.80 g, 3.04 mmol) and m-chlorobenzoyl chloride (0.80 g, 4.56 mmol) as raw materials, the operation process was the same as that of compound IV-1. In this case, 987 mg of white solid was obtained, the yield was 80.8%, and m.p. was at 150-152° C. $^1H$-NMR (300 MHz, $CDCl_3$) δ (ppm): 7.88-7.86 (m, 1H, ArH), 7.84-7.80 (m, 2H, ArH, NH), 7.74 (d, J=7.68 Hz, 1H, ArH), 7.53 (d, J=8.04 Hz, 1H, ArH), 7.43 (t, J=7.80 Hz, 1H, ArH), 7.28 (d, J=8.31 Hz, 1H, ArH), 6.07 (s, 2H, $OCH_2O$), 1.36 (s, 12H, $4CH_3$).

Synthesis of (R)-3-(4-amino-3-(7-(3-chlorobenzamido)benzo[d][1,3]dioxo heterocyclopenten-4)-1H-tert-butyl-pyrazolo[3,4-d]pyrimidin-1-)piperidine-1-tert-butyl formate (V-6)

Using compound III-1 (0.80 g, 1.80 mmol) and IV-6 (0.87 g, 2.16 mmol) as raw materials, the operation process was the same as that of compound V-1 to obtain 1.02 g (as crude product) of a light-yellow solid with a yield of 95.6%, m.p. at 128-130° C. $^1H$-NMR (300 MHz, $CDCl_3$) δ (ppm): 8.35 (s, 1H, ArH), 8.03 (s, 1H, NH), 7.95-7.85 (m, 2H, ArH), 7.79 (d, J=7.29 Hz, 1H, ArH), 7.55 (d, J=7.98 Hz, 1H, ArH), 7.44 (t, J=7.71 Hz, 1H, ArH), 7.13 (d, J=8.58 Hz, 1H, ArH), 6.12 (s, 2H, $OCH_2O$), 5.89 (s, 2H, $NH_2$), 4.93-4.75 (m, 1H, $CHCH_2NBoc$), 4.47-4.22 (m, 1H, $CHCH_2NBoc$), 4.21-4.02 (m, 1H, $CHCH_2NBoc$), 3.56-3.29 (m, 1H, $NCH_2CH_2$), 2.93-2.75 (m, 1H, $NCH_2CH_2$), 2.36-2.19 (m, 2H, $NCH_2CHCH_2$), 1.97-1.79 (m, 1H, $NCH_2CH_2$), 1.77-1.60 (m, 1H, $NCH_2CH_2$), 1.45 (s, 9H, Boc).

Synthesis of (R)—N-(7-(4-amino-1-(piperidin-3)-1H-pyrazolo[3,4-d]pyrimidin-3-)benzo[d][1,3]dioxo heterocyclopenten-4)-3-chlorobenzamide (VI-6)

Using compound V-6 (1.00 g, 1.69 mmol) as the raw material, the operation process was the same as that of compound VI-1 to obtain 882 mg of light-yellow solid, which was directly used in the next step without further purification.

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-3-chlorobenzamide (I-6)

Using compound VI-6 (500 mg, 1.02 mmol) and acryloyl chloride (97 mg, 1.07 mmol) as raw materials, the procedure was the same as that of compound I-1 to obtain 372 mg of white solid with a yield of 67.0%, m.p. at 143-144.5° C. $^1$H-NMR (300 MHz, $CDCl_3$) δ (ppm): 8.34 (d, J=11.04 Hz, 1H, ArH), 8.21 (d, J=9.12 Hz, 1H, ArH), 7.92 (s, 1H, NH), 7.90-7.77 (m, 2H, ArH), 7.55 (d, J=7.77 Hz, 1H, ArH), 7.45 (t, J=7.65 Hz, 1H, ArH), 7.16-7.05 (m, 1H, ArH), 6.68-6.52 (m, 1H, $CH{=}CH_2$), 6.34-6.22 (m, 1H, $CH{=}CH_2$), 6.12 (s, 2H, $OCH_2O$), 6.02 (s, 1H, $NH_2$), 5.76-5.61 (m, 1H, $CH{=}CH_2$), 4.95-4.78 (m, 1.5H, $N\underline{CH_2CH}$), 4.68-4.55 (m, 0.5H, $NCH_2\underline{CH}$), 4.28-4.16 (m, 0.5H, $N\underline{CH_2}CH$), 4.10-3.97 (m, 0.5H, $NC\underline{H_2}CH$), 3.85-3.69 (m, 0.5H, $\underline{NCH_2}CH_2$), 3.45-3.29 (m, 0.5H, $\underline{NCH_2}CH_2$), 3.26-3.11 (m, 0.5H, $NC\underline{H_2}CH_2$), 2.93-2.79 (m, 0.5H, $NCH_2CH_2$), 2.49-2.18 (m, 3H, $NCH_2CHC\underline{H_2}$, $NH_2$), 2.07-1.91 (m, 1H, $NCH_2C\underline{H_2}$), 1.81-1.64 (m, 1H, $NCH_2\underline{CH_2}$); HRMS (ESI): m/z $[M+H]^+$. Calcd for $C_{27}H_{25}ClN_7O_4$: 546.1657; found: 546.1662.

Example 7

Synthesis of (R)—N-(7-(1-(1-acryloylpiperidin-3)-4-amino-1H-pyrazolo[3,4-d]pyrimidin-3-yl)benzo[d][1,3]dioxo heterocyclopenten-4)-4-chlorobenzamide (I-7)

Synthesis of 4-chloro-N-(7-(4,4,5,5-tetramethyl-1,3,2-dioxaborolan-2)benzo[d][1, 3]dioxo heterocyclopenten-4-)benzamide (IV-7)

Using compound XI (0.80 g, 3.04 mmol) and p-chlorobenzoyl chloride (0.80 g, 4.56 mmol) as raw materials, the operation process was the same as that of compound IV-1 to obtain 1.02 g of white solid with a yield of 83.6%, m.p. at 210-212° C. $^1$H-NMR (300 MHz, $CDCl_3$) δ (ppm): 7.99-7.76 (m, 4H, ArH), 7.60-7.45 (m, 2H, ArH, NH), 7.32-7.26 (m, 1H, ArH), 6.07 (s, 2H, $OCH_2O$), 1.36 (s, 12H, $4CH_3$).

Synthesis of (R)-3-(4-amino-3-(7-(4-chlorobenzamido)benzo[d][1,3]dioxo heterocyclopenten-4)-1H-tert-butyl-pyrazolo[3,4-d]pyrimidin-1-)piperidine-1-tert-butyl formate (V-7)

Using compound III-1 (0.80 g, 1.80 mmol) and IV-7 (0.87 g, 2.16 mmol) as raw materials, the operation process was the same as that of compound V-1 to obtain 1.14 g of light-yellow solid, m.p. at 120-122° C. $^1$H-NMR (300 MHz, $CDCl_3$) δ (ppm): 8.35 (s, 1H, ArH), 7.99 (s, 1H, NH), 7.96-7.81 (m, 3H, ArH), 7.48 (d, J=7.83 Hz, 2H, ArH), 7.13 (d, J=8.43 Hz, 1H, ArH), 6.12 (s, 2H, $OCH_2O$), 5.87 (s, 2H, $NH_2$), 4.92-4.77 (m, 1H, $CHC\underline{H_2}NBoc$), 4.46-4.23 (m, 1H, $\underline{CH}CH_2NBoc$), 4.20-4.02 (m, 1H, $CHC\underline{H_2}NBoc$), 3.52-3.28 (m, 1H, $NC\underline{H_2}CH_2$), 2.93-2.74 (m, 1H, $NC\underline{H_2}CH_2$), 2.37-2.18 (m, 2H, $NCH_2CHC\underline{H_2}$), 1.98-1.80 (m, 1H, $NCH_2C\underline{H_2}$), 1.79-1.59 (m, 1H, $NCH_2C\underline{H_2}$), 1.45 (s, 9H, NBoc).

Synthesis of (R)—N-(7-(4-amino-1-(piperidin-3)-1H-pyrazolo[3,4-d]pyrimidin-3-)benzo[d][1,3]dioxo heterocyclopenten-4)-4-chlorobenzamide (VI-7)

Using compound V-7 (1.00 g, 1.69 mmol) as the starting material, the operation process was the same as that of compound VI-1 to obtain 777 mg of light-yellow solid, which was directly used in the next step without further purification.

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-4-chlorobenzamide (I-7)

Using compound VI-7 (500 mg, 1.02 mmol) and acryloyl chloride (97 mg, 1.07 mmol) as raw materials, the procedure was the same as that of compound I-1 to obtain 240 mg of white solid with a yield of 43.2%, m.p. at 159.5-161° C. $^1$H-NMR (400 MHz, $CDCl_3$) δ (ppm): 8.32 (d, J=11.08 Hz, 1H, ArH), 8.13 (s, 1H, CONH), 7.98-7.90 (m, 1H, ArH), 7.87 (d, J=6.92 Hz, 2H, ArH), 7.52 (d, J=7.12 Hz, 2H, ArH), 7.10 (d, J=6.04 Hz, 1H, ArH), 6.67-6.53 (m, 1H, $CH{=}CH_2$), 6.35-6.23 (m, 1H, $CH{=}CH_2$), 6.11 (br, 3H, $OCH_2O$, NH), 5.76-5.61 (m, 1H, $CH{=}CH_2$), 4.95-4.82 (m, 1.5H, $N\underline{CH_2CH}$), 4.67-4.56 (m, 0.5H, $NCH_2\underline{CH}$), 4.28-4.15 (m, 0.5H, $N\underline{CH_2}CH$), 4.08-3.97 (m, 0.5H, $NC\underline{H_2}CH$), 3.85-3.72 (m, 0.5H, $\underline{NCH_2}CH_2$), 3.42-3.29 (m, 0.5H, $NC\underline{H_2}CH_2$), 3.25-3.13 (m, 0.5H, $NC\underline{H_2}CH_2$), 2.93-2.79 (m, 0.5H, $NC\underline{H_2}CH_2$), 2.65 (s, 1H, $NH_2$), 2.47-2.32 (m, 1H, $NCH_2CHC\underline{H_2}$), 2.31-2.18 (m, 1H, $NCH_2CHC\underline{H_2}$), 2.04-1.92 (m, 1H, $NCH_2C\underline{H_2}$), 1.80-1.64 (m, 1H, $NCH_2\underline{CH_2}$); HRMS (ESI): m/z $[M+H]^+$. Calcd for $C_{27}H_{25}ClN_7O_4$: 546.1657; found: 546.1655.

Example 8

Synthesis of (R)—$N^1$-(7-(1-(1-acryloylpiperidin-3-yl)-4-amino-1H-pyrazolo[3,4-d]pyrimidin-3-)benzo[d][1,3]dioxo heterocyclopenten-4)-$N^3$-(2,2,2-trifluoroethyl)isophthalamide (I-8)

Synthesis of 3-((7-(4,4,5,5-tetramethyl-1,3,2-dioxaborolan-2-yl)benzo[d][1,3]dioxo heterocyclopenten-4)-carbamoyl)methyl benzoate (IV-8)

Using compound XI (1.00 g, 3.80 mmol) and monomethyl isophthalate (1.03 g, 5.72 mmol) as raw materials, the operation process was the same as that of compound IV-2 to obtain 1.45 g of white solid with a yield of 89.7%, and it was directly used in next step without further purification. $^1$H-NMR (300 MHz, $CDCl_3$) δ (ppm): 8.51 (s, 1H, NH), 8.22 (d, J=7.77 Hz, 1H, ArH), 8.12 (d, J=7.89 Hz, 1H, ArH), 7.91 (s, 1H, ArH), 7.84 (d, J=8.43 Hz, 1H, ArH), 7.59 (t, J=7.71 Hz, 1H, ArH), 7.29 (d, J=8.49 Hz, 1H, ArH), 6.08 (s, 2H, $OCH_2O$), 3.96 (s, 3H, $CH_3$), 1.37 (s, 12H, $4CH_3$).

Synthesis of (R)-3-(4-amino-3-(7-(3-methoxycarbonylbenzamide)benzo[d][1,3]dioxo heterocyclopenten-4)-1H-pyrazolo[3,4-d]pyrimidin-1-)piperidine-1-tert-butyl formate (V-8)

Using compound III-1 (0.80 g, 1.80 mmol) and IV-8 (1.15 g, 2.70 mmol) as raw materials, the operation process was the same as that of compound V-1 to obtain 1.52 g of gray solid, which was directly used in the next step without purification.

Synthesis of (R)-3-((7-(4-amino-1-(1-tert-butoxycarbonyl)piperidin-3)-1H-pyrazolo[3,4-d]pyrimidine-3-benzo[d][1,3]dioxo heterocyclopenten-4-)carbamoyl)benzoic acid (V-8-1)

Mix compound V-8 (1.40 g, 2.27 mmol), lithium hydroxide monohydrate (0.14 g, 3.41 mmol) and methanol/water (12 mL/4 mL), and stir the mixture overnight at room temperature. Distill methanol off under reduced pressure, add water and ethyl acetate, remove the organic layer, adjust the pH of the aqueous layer to 3-4 with 2 mol/L hydrochloric acid, filter with suction, and dry it to obtain 1.13 g of white solid with a yield of 82.6%, m.p. at 168-170° C.

Synthesis of (R)-3-(4-amino-3-(7-(3-((2,2,2-trifluoroethyl) carbamoyl)benzamide)benzo[d][1,3]dioxo heterocyclopenten-4)-1H-pyrazolo[3,4-d]pyrimidin-1)piperidine-1-tert-butyl formate (V-8-2)

Dissolve V-8-1 (900 mg, 1.50 mmol), HOBt (243 mg, 1.80 mmol), EDCI (344 mg, 1.80 mmol) in 5 mL DMF, add triethylamine (227 mg, 2.24 mmol) and trifluoroethylamine (156 mg, 1.57 mmol); the mixture was stirred overnight at room temperature. Add 25 mL of water, extract with ethyl acetate, wash the organic layer with water (10 mL×3), then wash with saturated sodium chloride (10 mL×3), and dry over anhydrous sodium sulfate. Suction filtration, the filtrate was evaporated to dryness under reduced pressure, and the residue was purified by column chromatography (eluent: Dichloromethane:Methanol=100-40:1) to obtain 667 mg of white solid with a yield of 65.3%, m.p. at 143-145° C. $^1$H-NMR (300 MHz, $CDCl_3$) δ (ppm): 8.40 (s, 1H, ArH), 8.32 (s, 1H, NH), 8.27 (s, 1H, ArH), 8.04 (q, J=7.92 Hz, 2H, ArH), 7.76 (d, J=7.92 Hz, 1H, ArH), 7.56 (t, J=7.71 Hz, 1H, ArH), 7.22 (s, 1H, NH), 7.09 (d, J=8.79 Hz, 1H, ArH), 6.06 (s, 2H, $OCH_2O$), 5.87 (s, 2H, $NH_2$), 4.88-4.74 (m, 1H, $CHC\underline{H}_2NBoc$), 4.37-4.25 (m, 1H, $C\underline{H}CH_2NBoc$), 4.21-4.05 (m, 3H, $CHC\underline{H}_2NBoc$, $C\underline{H}_2CF_3$), 3.49-3.30 (m, 1H, $NC\underline{H}_2CH_2$), 2.90-2.74 (m, 1H, $NC\underline{H}_2CH_2$), 2.29-2.14 (m, 2H, $NCH_2CHC\underline{H}_2$), 1.94-1.81 (m, 1H, $NCH_2C\underline{H}_2$), 1.76-1.60 (m, 1H, $NCH_2C\underline{H}_2$), 1.43 (s, 9H, $3CH_3$).

Synthesis of (R)—$N^1$-(7-(4-amino-1-(piperidin-3)-1H-pyrazolo[3,4-d]pyrimidin-3-)benzo[d][1,3]dioxo heterocyclopenten-4)-$N^3$-(2,2,2-trifluoroethyl)isophthalamide (VI-8)

Using compound V-8-2 (550 mg, 0.81 mmol) as the raw material, the operation process was the same as that of compound VI-1 to obtain 430 mg of a light-yellow solid with a yield of 91.62%, which was directly used in the next step without further purification.

Synthesis of (R)—$N^1$-(7-(1-(1-acryloylpiperidin-3)-4-amino-1H-pyrazolo[3,4-d]pyrimidin-3-)benzo[d][1,3]dioxo heterocyclopenten-4)-$N^3$-(2,2,2-trifluoroethyl)isophthalamide (I-8)

Starting from compound VI-8 (400 mg, 0.69 mmol) and acryloyl chloride (65 mg, 0.72 mmol), the procedure was the same as that of compound I-1 to obtain 231 mg of white solid with a yield of 52.8%, m.p. at 174-176° C. $^1$H-NMR (300 MHz, DMSO-$d_6$) δ (ppm): 10.43 (s, 1H, NH), 9.30 (s, 1H, NH), 8.50 (s, 1H, ArH), 8.33-8.00 (m, 2H, ArH), 7.66 (s, 1H, ArH), 7.35-6.97 (m, 2H, ArH), 6.95-6.55 (m, 2H, ArH, $CH{=}CH_2$), 6.37-5.92 (m, 3H, $CH{=}CH_2$, $OCH_2O$), 5.83-5.49 (m, 1H, $CH{=}CH_2$), 4.86-4.46 (m, 1.5H, $NC\underline{H}_2C\underline{H}$), 4.37-3.91 (m, 3H, $NC\underline{H}_2C\underline{H}$, $NHC\underline{H}_2CF_3$), 3.79-3.58 (m, 0.5H, $NC\underline{H}_2CH$), 3.07-2.84 (m, 1H, $NC\underline{H}_2C\underline{H}_2$), 2.36-2.03 (m, 2H, $NC\underline{H}_2CH_2$, $NCH_2CHC\underline{H}_2$), 2.02-1.80 (m, 1H, $NCH_2CHC\underline{H}_2$), 1.72-1.46 (m, 1H, $NCH_2C\underline{H}_2$), 1.36-1.10 (m, 1H, $NCH_2C\underline{H}_2$); HRMS (ESI): m/z $[M+H]^+$. Calcd for $C_{30}H_{28}F_3N_8O_5$: 637.2135; found: 637.2134.

Example 9

Synthesis of (R)—N-(7-(1-(1-acryloylpiperidin-3)-4-amino-1H-pyrazolo[3,4-d]pyrimidin-3)benzo[d][1,3]dioxo heterocyclopenten-4)-4-trifluoromethylbenzamide (1-9)

Synthesis of N-(7-(4,4,5,5-tetramethyl-1,3,2-dioxaborolan-2-)benzo[d][1,3]dioxo heterocyclopenten-4)-4-trifluoromethylbenzamide (IV-9)

Using compound XI (0.50 g, 1.90 mmol) and 4-trifluoromethylbenzoyl chloride (0.60 g, 2.85 mmol) as raw materials, the operation process was the same as that of compound IV-1 to obtain 654 mg of white solid with a yield of 79.1%, m.p. at 240-242° C. $^1$H-NMR (300 MHz, $CDCl_3$) δ (ppm): 7.99 (d, J=8.16 Hz, 2H, ArH), 7.88-7.81 (m, 2H, ArH, NH), 7.76 (d, J=8.19 Hz, 2H, ArH), 7.29 (d, J=8.52 Hz, 1H, ArH), 6.08 (s, 2H, $OCH_2O$), 1.37 (s, 12H, $4CH_3$).

Synthesis of (R)-3-(4-amino-3-(7-(4-trifluoromethylbenzamido) benzo[d][1,3]dioxo heterocyclopenten-4)-1H-pyrazolo[3,4-d]pyrimidin-1-)piperidine-1-tert-butyl formate (V-9)

Using compound III-1 (0.50 g, 1.13 mmol) and IV-9 (0.59 g, 1.35 mmol) as raw materials, the operation process was the same as that of compound V-1 to obtain 0.62 g of a light-yellow solid with a yield of 88.1%, m.p. at 140-142° C. $^1$H-NMR (300 MHz, $CDCl_3$) δ (ppm): 8.38 (s, 1H, ArH), 8.05 (d, J=8.13 Hz, 2H, ArH), 8.01-7.95 (m, 2H, ArH, NH), 7.81 (d, J=8.28 Hz, 2H, ArH), 7.18 (d, J=8.73 Hz, 1H, ArH), 6.16 (s, 2H, $OCH_2O$), 5.74 (s, 2H, $NH_2$), 4.934.81 (m, 1H, $CHC\underline{H}_2NBoc$), 4.42-4.27 (m, 1H, $C\underline{H}CH_2NBoc$), 4.21-4.10 (m, 1H, $CHC\underline{H}_2NBoc$), 3.54-3.39 (m, 1H, $NC\underline{H}_2CH_2$), 2.95-2.79 (m, 1H, $NC\underline{H}_2CH_2$), 2.35-2.19 (m, 2H, $NCH_2CHC\underline{H}_2$), 1.96-1.87 (m, 1H, $NCH_2C\underline{H}_2$), 1.78-1.68 (m, 1H, $NC\underline{H}_2C\underline{H}_2$), 1.47 (s, 9H, NBoc).

Synthesis of (R)—N-(7-(4-amino-1-(piperidin-3)-1H-pyrazolo[3,4-d]pyrimidin-3-)benzo[d][1,3]dioxo heterocyclopenten-4)-4-trifluoromethylbenzamide (VI-9)

Using compound V-9 (550 mg, 0.88 mmol) as the starting material, the operation process was the same as that of compound VI-1 to obtain 420 mg of light-yellow solid with a yield of 90.91%.

Synthesis of (R)—N-(7-(1-(1-acryloylpiperidin-3)-4-amino-1H-pyrazolo[3,4-d]pyrimidin-3)benzo[d][1,3]dioxo heterocyclopenten-4)-4-trifluoromethylbenzamide (I-9)

Using compound VI-9 (500 mg, 0.95 mmol) and acryloyl chloride (103 mg, 1.14 mmol) as raw materials, the procedure was the same as that of compound I-1 to obtain 289 mg of white solid with a yield of 52.4%, m.p. at 148.5-150° C. $^1$H-NMR (300 MHz, $CDCl_3$) δ (ppm): 8.43-8.23 (m, 2H, ArH, NH), 8.05 (d, J=7.62 Hz, 2H, ArH), 7.92-7.81 (m, 1H, ArH), 7.76 (d, J=7.44 Hz, 2H, ArH), 7.20-7.04 (m, 1H, ArH), 6.70-6.48 (m, 1H, $CH{=}CH_2$), 6.35-6.19 (m, 1H, $CH{=}CH_2$), 6.11 (s, 2H, $OCH_2O$), 5.96 (s, 1H, $NH_2$), 5.75-5.59 (m, 1H, $CH{=}CH_2$), 4.98-4.75 (m, 1.5H, $NC\underline{H}_2C\underline{H}$), 4.67-4.48 (m, 0.5H, $NCH_2C\underline{H}$), 4.30-4.13 (m, 0.5H, $NC\underline{H}_2CH$), 4.09-3.92 (m, 0.5H, $NC\underline{H}_2CH$), 3.88-3.67 (m, 0.5H, $NC\underline{H}_2CH_2$), 3.45-3.28 (m, 0.5H, $NC\underline{H}_2CH_2$), 3.26-3.09 (m, 0.5H, $NCH_2CH_2$), 2.96-2.80 (m, 0.5H, $NCH_2CH_2$), 2.50-2.31 (m, 1H, $NCH_2CHCH_2$), 2.29-2.18 (m, 2H, $NCH_2CHCH_2$, $NH_2$), 2.07-1.89 (m, 1H, $NCH_2CH_2$), 1.81-1.60 (m, 1H, $NCH_2CH_2$); $^{13}$C-NMR (75 MHz, DMSO-$d_6$) δ (ppm): 164.55, 163.98, 158.03, 155.89, 155.66, 153.71, 145.90, 140.95, 138.29, 137.78, 128.73, 128.32, 127.29, 125.69, 125.40, 122.11, 120.95, 118.82, 111.82, 101.72, 98.64, 52.91 (0.5C), 52.19 (0.5C), 49.19 (0.5C), 48.70 (0.5C), 45.65 (0.5C), 45.10 (0.5C), 30.38 (0.5C), 29.57 (0.5C), 26.78 (0.5C), 24.81 (0.5C); HRMS (ESI): m/z $[M+H]^+$. Calcd for $C_{28}H_{25}F_3N_7O_4$: 580.1920; found: 580.1918.

Example 10

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-4-methoxybenzamide (I-10)

Synthesis of N-(7-(4,4,5,5-tetramethyl-1,3,2-dioxaborolan-2-yl)benzo[d][1,3]dioxo heterocyclopenten-4)-4-methoxybenzamide (IV-10)

Using compound XI (1.50 g, 5.70 mmol) and 4-methoxybenzoyl chloride (1.46 g, 8.55 mmol) as raw materials, the operation process was the same as that of compound IV-1 to obtain 1.92 g of white solid with a yield of 84.1%, m.p. at 176-178° C. $^1$H-NMR (300 MHz, $CDCl_3$) δ (ppm): 7.93-7.81 (m, 3H, ArH), 7.78 (br, 1H, NH), 7.28 (d, J=8.31 Hz, 1H, ArH), 6.97 (d, J=8.58 Hz, 2H, ArH), 6.06 (s, 2H, $OCH_2O$), 3.87 (s, 3H, $OCH_3$), 1.36 (s, 12H, $4CH_3$).

Synthesis of (R)-3-(4-amino-3-(7-(4-methoxybenzamido)benzo [d][1,3]dioxo heterocyclopenten-4)-1H-pyrazolo[3,4-d]pyrimidin-1-yl)piperidine-1-tert-butyl formate (V-10)

Using compound III-1 (1.20 g, 2.70 mmol) and IV-10 (1.29 g, 3.24 mmol) as raw materials, the operation process was the same as that of compound V-1 to obtain 1.49 g of a light-yellow solid with a yield of 93.7%, m.p. at 104-106° C. $^1$H-NMR (300 MHz, $CDCl_3$) δ (ppm): 8.38 (s, 1H, ArH), 8.01 (d, J=8.70 Hz, 1H, ArH), 7.90 (d, J=8.85 Hz, 2H, ArH), 7.87 (br, 1H, NH), 7.15 (d, J=8.70 Hz, 1H, ArH), 7.02 (d, J=8.82 Hz, 2H, ArH), 6.14 (s, 2H, $OCH_2O$), 5.75 (s, 2H, $NH_2$), 4.94-4.80 (m, 1H, $CHCH_2NBoc$), 4.44-4.25 (m, 1H, $CHCH_2NBoc$), 4.23-4.06 (m, 1H, $CHCH_2NBoc$), 3.91 (s, 3H, $OCH_3$), 3.56-3.36 (m, 1H, $NCH_2CH_2$), 2.93-2.78 (m, 1H, $NCH_2CH_2$), 2.34-2.17 (m, 2H, $NCH_2CHCH_2$), 1.98-1.83 (m, 2H, $NCH_2CH_2$), 1.47 (s, 9H, NBoc).

Synthesis of (R)—N-(7-(4-amino-1-(piperidin-3)-1H-pyrazolo[3,4-d]pyrimidin-3-)benzo[d][1,3]dioxo heterocyclopenten-4)-4-methoxybenzamide (VI-10)

Using compound V-10 (1.27 g, 2.17 mmol) as the starting material, the operation process was the same as that of compound VI-1 to obtain 1.04 g of a light-yellow solid with a yield of 98.01%.

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-4-methoxybenzamide (I-10)

Using compound VI-10 (100 mg, 0.21 mmol) and acryloyl chloride (19 mg, 0.22 mmol) as raw materials, the procedure was the same as compound I-1 to obtain 89 mg of white solid with a yield of 80.1%, m.p. at 216-218° C. $^1$H-NMR (300 MHz, $CDCl_3$) δ (ppm): 8.35 (s, 1H, ArH), 8.02-7.93 (m, 2H, ArH, NH), 7.90 (d, J=7.68 Hz, 2H, ArH), 7.12 (d, J=8.16 Hz, 1H, ArH), 7.00 (d, J=7.74 Hz, 2H, ArH), 6.71-6.51 (m, 1H, $CH{=}CH_2$), 6.38-6.22 (m, 1H, $CH{=}CH_2$), 6.12 (s, 2H, $OCH_2O$), 5.90 (s, 1H, $NH_2$), 5.77-5.61 (m, 1H, $CH{=}CH_2$), 4.96-4.80 (m, 1.5H, $NCH_2CH$), 4.71-4.53 (m, 0.5H, $NCH_2CH$), 4.29-4.16 (m, 0.5H, $NCH_2CH$), 4.08-3.98 (m, 0.5H, $NCH_2CH$), 3.90 (s, 3H, $OCH_3$), 3.82-3.69 (m, 0.5H, $NCH_2CH_2$), 3.51-3.32 (m, 0.5H, $NCH_2CH_2$), 3.29-3.10 (m, 0.5H, $NCH_2CH_2$), 2.97-2.75 (m, 0.5H, $NCH_2CH_2$), 2.51-2.35 (m, 1H, $NCH_2CHCH_2$), 2.35-2.14 (m, 2H, $NCH_2CHCH_2$, $NH_2$), 2.09-1.89 (m, 1H, $NCH_2CH_2$), 1.83-1.64 (m, 1H, $NCH_2CH_2$); HRMS (ESI): m/z $[M+H]^+$. Calcd for $C_{28}H_{28}N_7O_5$: 542.2152; found: 542.2156.

Example 11

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-4-tert-butylbenzamide (I-11)

Synthesis of 4-tert-butyl-N-(7-(4,4,5,5-tetramethyl-1,3,2-dioxaborolan-2-)benzo[d][1,3]dioxo heterocyclopenten-4-)benzamide (IV-11)

Using compound XI (1.00 g, 3.80 mmol) and 4-tert-butylbenzoic acid (1.02 g, 5.70 mmol) as raw materials, the operation process was the same as that of compound IV-2 to obtain 982 mg of white solid with a yield of 61.0%, m.p. at 170-172° C. $^1$H-NMR (300 MHz, $CDCl_3$) δ (ppm): 7.91 (d, J=8.52 Hz, 1H, ArH), 7.86 (s, 1H, NHCO), 7.82 (d, J=8.46 Hz, 2H, ArH), 7.51 (d, J=8.46 Hz, 2H, ArH), 7.28 (d, J=8.52 Hz, 1H, ArH), 6.07 (s, 2H, $OCH_2O$), 1.36 (s, 12H, $4CH_3$), 1.35 (s, 9H, $C(CH_3)_3$).

Synthesis of (R)-3-(4-amino-3-(7-(4-tert-butylbenzamido)benzo [d][1,3]dioxo heterocyclopenten-4)-1H-pyrazolo[3,4-d]pyrimidin-1-)piperidine-1-tert-butyl formate (V-11)

Using compound III-1 (0.75 g, 1.69 mmol) and IV-11 (0.86 g, 2.03 mmol) as raw materials, the operation process was the same as that of compound V-1 to obtain 969 mg of light-yellow solid with a yield of 93.5%, m.p. at 140-142° C. $^1$H-NMR (300 MHz, $CDCl_3$) δ (ppm): 8.39 (s, 1H, ArH), 8.07-7.99 (m, 2H, ArH, NH), 7.89 (d, J=8.34 Hz, 2H, ArH), 7.56 (d, J=8.31 Hz, 2H, ArH), 7.16 (d, J=8.67 Hz, 1H, ArH), 6.16 (s, 2H, $OCH_2O$), 5.93 (s, 1H, $NH_2$), 4.96-4.82 (m, 1H, $CHCH_2NBoc$), 4.49-4.10 (m, 2H, $CHCH_2NBoc$), 3.62-3.32 (m, 1H, $NCH_2CH_2$), 2.97-2.79 (m, 1H, $NCH_2CH_2$), 2.27-2.14 (m, 3H, $NCH_2CHCH_2$, $NH_2$), 1.99-1.87 (m, 1H, $NCH_2CH_2$), 1.80-1.68 (m, 1H, $NCH_2CH_2$), 1.48 (s, 9H, $3CH_3$), 1.40 (s, 9H, $3CH_3$).

Synthesis of (R)—N-(7-(4-amino-1-(piperidin-3-yl)-1H-pyrazolo[3,4-d]pyrimidin-3-)benzo[d][1,3]dioxo heterocyclopenten-4)-4-tert-butylbenzamide (VI-11)

Using compound V-11 (900 mg, 1.47 mmol) as the starting material, the operation process was the same as that of compound VI-1 to obtain 697 mg of a light-yellow solid with a yield of 92.5%, which was directly used in the next step without further purification.

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-4-tert-butylbenzamide (I-11)

Using compound VI-11 (600 mg, 1.17 mmol) and acryloyl chloride (111 mg, 1.23 mmol) as raw materials, the procedure was the same as compound I-1 to obtain 242 mg of white solid with a yield of 36.5%, m.p. at 136-138° C. $^1$H-NMR (400 MHz, $CDCl_3$) δ (ppm): 8.32 (d, J=11.08 Hz, 1H, ArH), 8.12 (s, 1H, NH), 7.98-7.89 (m, 1H, ArH), 7.86 (d, J=6.92 Hz, 2H, ArH), 7.52 (d, J=7.12 Hz, 2H, ArH), 7.10 (d, J=6.04 Hz, 1H, ArH), 6.68-6.51 (m, 1H, $CH{=}CH_2$), 6.36-6.21 (m, 1H, $CH{=}CH_2$), 6.17-6.01 (m, 3H, $NH_2$, $OCH_2O$), 5.76-5.60 (m, 1H, $CH{=}CH_2$), 4.95-4.78 (m, 1.5H, $NCH_2CH$), 4.67-4.50 (m, 0.5H, $NCH_2CH$), 4.29-4.14 (m, 0.5H, $NCH_2CH$), 4.09-3.95 (m, 0.5H, $NCH_2CH$), 3.84-3.69 (m, 0.5H, $NCH_2CH_2$), 3.41-3.27 (m, 0.5H, $NCH_2CH_2$), 3.24-3.10 (m, 0.5H, $NCH_2CH_2$), 2.92-2.78 (m, 0.5H, $NCH_2CH_2$), 2.65 (s, 1H, $NH_2$), 2.48-2.31 (m, 1H, $NCH_2CHCH_2$), 2.30-2.16 (m, 1H, $NCH_2CHCH_2$), 2.04-1.89 (m, 1H, $NCH_2CH_2$), 1.79-1.61 (m, 1H, $NCH_2CH_2$), 1.35 (s, 9H, $3CH_3$); HRMS (ESI): m/z $[M+H]^+$. Calcd for $C_{31}H_{34}N_7O_4$: 568.2672; found: 568.2674.

Example 12

Synthesis of (R)—N-(7-(1-(1-acryloylpiperidin-3)-4-amino-1H-pyrazolo[3,4-d]pyrimidin-3-yl)benzo[d][1,3]dioxo heterocyclopenten-4)-3,4-dimethoxybenzamide (I-12)

Synthesis of 3,4-dimethoxy-N-(7-(4,4,5,5-tetramethyl-1,3,2-dioxaborolan-2-)benzo[d][1,3]dioxo heterocyclopenten-4-)benzamide (IV-12)

Using compound XI (1.00 g, 3.80 mmol) and 3,4-dimethoxybenzoyl chloride (1.14 g, 5.70 mmol) as raw materials, the operation process was the same as that of compound IV-1 to obtain 926 mg of white solid with a yield of 57.2%, m.p. at 166-168° C. $^1$H-NMR (300 MHz, $CDCl_3$) ((ppm): 7.90-7.82 (m, 2H, ArH, NHCO), 7.51 (s, 1H, ArH), 7.41 (d, J=8.31 Hz, 1H, ArH), 7.28 (d, J=8.04 Hz, 1H, ArH), 6.91 (d, J=8.34 Hz, 1H, ArH), 6.07 (s, 2H, $OCH_2O$), 3.95 (s, 3H, $OCH_3$), 3.95 (s, 3H, $OCH_3$), 1.36 (s, 12H, $4CH_3$).

Synthesis of (R)-3-(4-amino-3-(7-(3,4-dimethoxybenzamido) benzo[d][1,3]dioxo heterocyclopenten-4)-1H-pyrazolo[3,4-d]pyrimidin-1-)piperidine-1-tert-butyl formate (V-12)

Using compound III-1 (0.70 g, 1.58 mmol) and IV-12 (0.81 g, 1.89 mmol) as raw materials, the operation process was the same as that of compound V-1 to obtain 731 mg of light-yellow solid with a yield of 75.1%, m.p. at 120-122° C. $^1$H-NMR (300 MHz, $CDCl_3$) δ (ppm): 8.37 (s, 1H, ArH), 8.00 (d, J=8.94 Hz, 1H, ArH), 7.88 (s, 1H, ArH), 7.54 (s, 1H, NH), 7.44 (d, J=8.37 Hz, 1H, ArH), 7.15 (d, J=8.91 Hz, 1H, ArH), 6.94 (d, J=8.01 Hz, 1H, ArH), 6.13 (s, 2H, $OCH_2O$), 5.78 (s, 2H, $NH_2$), 4.92-4.78 (m, 1H, $CHCH_2NBoc$), 4.38-4.24 (m, 1H, $CHCH_2NBoc$), 4.20-4.08 (m, 1H, $CHCH_2NBoc$), 3.98 (s, 3H, $OCH_3$), 3.97 (s, 3H, $OCH_3$), 3.52-3.37 (m, 1H, $NCH_2CH_2$), 2.91-2.77 (m, 1H, $NCH_2CH_2$), 2.33-2.24 (m, 1H, $NCH_2CHCH_2$), 2.23-2.14 (m, 1H, $NCH_2CHCH_2$), 1.96-1.84 (m, 1H, $NCH_2CH_2$), 1.77-1.65 (m, 1H, $NCH_2CH_2$), 1.45 (s, 9H, NBoc).

Synthesis of (R)—N-(7-(4-amino-1-(piperidin-3)-1H-pyrazolo[3,4-d]pyrimidin-3-yl)benzo[d][1,3]dioxo heterocyclopenten-4)-3,4-dimethoxybenzamide (VI-12)

Using compound V-12 (700 mg, 1.13 mmol) as the raw material, the operation process was the same as that of compound VI-1 to obtain 587 mg of light-yellow solid, which was directly used in the next step without further purification.

Synthesis of (R)—N-(7-(1-(1-acryloylpiperidin-3)-4-amino-1H-pyrazolo[3,4-d]pyrimidin-3-yl)benzo[d][1,3]dioxo heterocyclopenten-4)-3,4-dimethoxybenzamide (I-12)

Using compound VI-12 (537 mg, 1.04 mmol) and acryloyl chloride (99 mg, 1.09 mmol) as raw materials, the procedure was the same as that of compound I-1 to obtain 309 mg of white solid with a yield of 52.1%, m.p. at 164-165° C. $^1$H-NMR (400 MHz, $CDCl_3$) δ (ppm): 8.41-8.25 (m, 1H, ArH), 8.05 (s, 1H, NH), 7.94-7.87 (m, 1H, ArH), 7.56-7.51 (m, 1H, ArH), 7.49-7.44 (m, 1H, ArH), 7.11 (d, J=8.64 Hz, 1H, ArH), 6.93 (d, J=8.40 Hz, 1H, ArH), 6.68-6.52 (m, 1H, $CH{=}CH_2$), 6.36-6.23 (m, 1H, $CH{=}CH_2$), 6.12 (s, 2H, $OCH_2O$), 5.95 (br, 1H, $NH_2$), 5.78-5.60 (m, 1H, $CH{=}CH_2$), 4.94-4.83 (m, 1.5H, $NCH_2CH$), 4.66-4.55 (m, 0.5H, $NCH_2CH$), 4.26-4.17 (m, 0.5H, $NCH_2CH$), 4.09-4.00 (m, 0.5H, $NCH_2CH$), 3.96 (s, 3H, $OCH_3$), 3.96 (s, 3H, $OCH_3$), 3.83-3.73 (m, 0.5H, $NCH_2CH_2$), 3.41-3.31 (m, 0.5H, $NCH_2CH_2$), 3.24-3.13 (m, 0.5H, $NCH_2CH_2$), 2.94-2.81 (m, 0.5H, $NCH_2CH_2$), 2.45-2.34 (m, 1H, $NCH_2CHCH_2$), 2.29-2.23 (m, 2H, $NCH_2CHCH_2$, $NH_2$), 2.02-1.94 (m, 1H, $NCH_2CH_2$), 1.79-1.64 (m, 1H, $NCH_2CH_2$); HRMS (ESI): m/z $[M+H]^+$. Calcd for $C_{29}H_{30}N_7O_6$: 572.2258; found: 572.2252.

Example 13

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-4-(dimethylamino)benzamide (I-13)

Synthesis of 4-(dimethylamino)-N-(7-(4,4,5,5-tetramethyl-1,3,2-dioxaborolan-2-)benzo[d][1,3]dioxo heterocyclopenten-4-)benzamide (IV-13)

Using compound XI (1.00 g, 3.80 mmol) and 4-dimethylamino benzoyl chloride (1.05 g, 5.70 mmol) as raw materials, the operation process was the same as that of compound IV-1 to obtain 950 mg of white solid with a yield of 60.9%. It was directly used for next step without further purification.

Synthesis of (R)-3-(4-amino-3-(7-(4-(dimethylamino)benzamido) benzo[d][1,3]dioxo heterocyclopenten-4)-1H-pyrazolo[3,4-d]pyrimidin-1-yl)piperidine-1-tert-butyl formate (V-13)

Using compound III-1 (0.60 g, 1.35 mmol) and IV-13 (0.67 g, 1.62 mmol) as raw materials, the operation process was the same as that of compound V-1 to obtain 678 mg of light-yellow solid with a yield of 83.5%, m.p. at 138-140° C.

$^1$H-NMR (300 MHz, $CDCl_3$) δ (ppm): 8.36 (s, 1H, ArH), 8.04 (d, J=9.03 Hz, 1H, ArH), 7.89-7.76 (m, 3H, ArH, NH), 7.12 (d, J=7.98 Hz, 1H, ArH), 6.73 (d, J=8.61 Hz, 2H, ArH), 6.12 (s, 2H, $OCH_2O$), 5.75 (s, 2H, $NH_2$), 4.90-4.79 (m, 1H, $CHCH_2NBoc$), 4.40-4.26 (m, 1H, $CHCH_2NBoc$), 4.22-4.06 (m, 1H, $CHCH_2NBoc$), 3.54-3.35 (m, 1H, $NCH_2CH_2$), 3.07 (s, 6H, $N(CH_3)_2$), 2.90-2.74 (m, 1H, $NCH_2CH_2$), 2.34-2.15 (m, 2H, $NCH_2CHCH_2$), 1.99-1.82 (m, 2H, $NCH_2CH_2$), 1.45 (s, 9H, NBoc).

Synthesis of (R)—N-(7-(4-amino-1-(piperidin-3-)-1H-pyrazolo[3,4-d]pyrimidin-3-)benzo[d][1,3]dioxo heterocyclopenten-4)-4-(dimethylamino)benzamide (VI-13)

Using compound V-13 (850 mg, 1.42 mmol) as the raw material, the operation process was the same as that of compound VI-1 to obtain 588 mg of a light-yellow solid with a yield of 83.0%, which was directly used in the next step without further purification.

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-4-(dimethylamino) benzamide (I-13)

Using compound VI-13 (540 mg, 1.08 mmol) and acryloyl chloride (103 mg, 1.13 mmol) as raw materials, the operation process was the same as that of the target compound I-1 to obtain 342 mg of white solid with a yield of 57.2%, m.p. at 160-162° C. $^1$H-NMR (300 MHz, $CDCl_3$) δ (ppm): 8.33 (s, 1H, ArH), 8.04-7.88 (m, 2H, ArH, NH), 7.81 (d, J=6.66 Hz, 2H, ArH), 7.09 (d, J=8.07 Hz, 1H, ArH), 6.71 (d, J=6.96 Hz, 2H, ArH), 6.65-6.52 (m, 1H, $CH{=}CH_2$), 6.36-6.21 (m, 1H, $CH{=}CH_2$), 6.17-5.99 (m, 3H, $NH_2$, $OCH_2O$), 5.76-5.59 (m, 1H, $CH{=}CH_2$), 4.96-4.79 (m, 1.5H, $NCH_2CH$), 4.69-4.57 (m, 0.5H, $NCH_2CH$), 4.28-4.15 (m, 0.5H, $NCH_2CH$), 4.08-3.96 (m, 0.5H, $NCH_2CH$), 3.85-3.70 (m, 0.5H, $NCH_2CH_2$), 3.43-3.28 (m, 0.5H, $NCH_2CH_2$), 3.24-3.14 (m, 0.5H, $NCH_2CH_2$), 3.06 (s, 6H, $2CH_3$), 2.89-2.72 (m, 1.5H, $NCH_2CH_2$, $NH_2$), 2.47-2.31 (m, 1H, $NCH_2CHCH_2$), 2.30-2.16 (m, 1H, $NCH_2CHCH_2$), 2.04-1.89 (m, 1H, $NCH_2CH_2$), 1.80-1.61 (m, 1H, $NCH_2CH_2$); HRMS (ESI): m/z $[M+H]^+$. Calcd for $C_{29}H_{31}N_8O_4$: 555.2468; found: 555.2466.

Example 14

Synthesis of N-(7-(1-(1-acryloylpiperidin-3)-4-amino-1H-pyrazolo[3,4-d]pyrimidin-3-)benzo[d][1,3]dioxo heterocyclopenten-4)-4-(dimethylamino) benzamide (I-14)

Synthesis of tert-butyl 3-(4-amino-3-iodo-1H-pyrazolo[3,4-d]pyrimidin-1-)piperidine-1-tert-butyl formate (III-2)

Using compound VII-1 (3.00 g, 11.49 mmol) and 1-tert-butoxycarbonyl-3-hydroxypiperidine (VIII-2) (4.63 g, 22.99 mmol) as raw materials, the operation process was the same as that of compound 111-1 to obtain 3.91 g white solid with a yield of 76.5%, m.p. at 176-178° C. $^1$H-NMR (300 MHz, $CDCl_3$) δ (ppm): 8.31 (s, 1H, ArH), 6.17 (s, 2H, $NH_2$), 4.82-4.68 (m, 1H, $CHCH_2N$), 4.22-4.05 (m, 1H, $CHCH_2N$), 3.79-3.67 (m, 1H, $CHCH_2N$), 3.22-3.02 (m, 1H, $CHCH_2CH_2CH_2N$), 2.91-2.74 (m, 1H, $CHCH_2CH_2CH_2N$), 2.19-2.08 (m, 2H, $CHCH_2CH_2CH_2N$), 1.95-1.81 (m, 2H, $CHCH_2CH_2CH_2N$), 1.45 (s, 9H, NBoc).

Synthesis of 3-(4-amino-3-(7-(4-(dimethylamino) benzamido) benzo[d][1,3]dioxo heterocyclopenten-4)-1H-tert-butyl-pyrazolo[3,4-d]pyrimidin-1-)piperidine-1-tert-butyl formate (V-14)

Using compound III-2 (0.95 g, 2.14 mmol) and IV-13 (1.05 g, 2.57 mmol) as raw materials, the operation process was the same as that of compound V-1 to obtain 890 mg of light-yellow solid with a yield of 69.5%, m.p. at 140-142° C. $^1$H-NMR (300 MHz, $CDCl_3$) δ (ppm): 8.38 (s, 1H, ArH), 8.04 (d, J=8.73 Hz, 1H, ArH), 7.89 (s, 1H, NHCO), 7.85 (d, J=8.88 Hz, 2H, ArH), 7.15 (d, J=8.70 Hz, 1H, ArH), 6.75 (d, J=8.94 Hz, 2H, ArH), 6.15 (s, 2H, $OCH_2O$), 5.94 (s, 2H, $NH_2$), 4.94-4.81 (m, 1H, $NCH_2CH$), 4.33-4.12 (m, 2H, $NCH_2CH$), 3.59-3.37 (m, 1H, $NCH_2CH_2$), 3.10 (s, 6H, $N(CH_3)_2$), 2.93-2.81 (m, 1H, $NCH_2CH_2$), 2.27-2.19 (m, 2H, $NCH_2CHCH_2$), 1.98-1.87 (m, 1H, $NCH_2CH_2$), 1.78-1.66 (m, 1H, $NCH_2CH_2$), 1.48 (s, 9H, NBoc).

Synthesis of N-(7-(4-amino-1-(piperidin-3)-1H-pyrazolo[3,4-d]pyrimidin-3-)benzo[d][1,3]dioxo heterocyclopenten-4)-4-(dimethylamino)benzamide (VI-14)

Using compound V-14 (850 mg, 1.42 mmol) as the raw material, the operation process was the same as that of compound VI-1 to obtain 436 mg of light-yellow solid with a yield of 61.6%, which was directly used in the next step without further purification.

Synthesis of N-(7-(1-(1-acryloylpiperidin-3)-4-amino-1H-pyrazolo[3,4-d]pyrimidin-3-)benzo[d][1,3]dioxo heterocyclopenten-4)-4-(dimethylamino) benzamide (I-14)

Using compound VI-14 (420 mg, 0.84 mmol) and acryloyl chloride (80 mg, 0.88 mmol) as raw materials, the operation process was the same as that of compound I-1 to obtain 213 mg of white solid with a yield of 45.7%, m.p. at 160-162° C. $^1$H-NMR (300 MHz, $CDCl_3$) δ (ppm): 8.33 (s, 1H, ArH), 8.03 (d, J=8.97 Hz, 1H, ArH), 7.86-7.76 (m, 3H, ArH, NH), 7.11 (d, J=8.82 Hz, 1H, ArH), 6.71 (d, J=7.32 Hz, 2H, ArH), 6.67-6.52 (m, 1H, $CH{=}CH_2$), 6.36-6.22 (m, 1H, $CH{=}CH_2$), 6.11 (s, 2H, $OCH_2O$), 5.97 (br, 1H, $NH_2$), 5.77-5.63 (m, 1H, $CH{=}CH_2$), 4.97-4.80 (m, 1.5H, $NCH_2CH$), 4.72-4.58 (m, 0.5H, $NCH_2CH$), 4.30-4.17 (m, 0.5H, $NCH_2CH$), 4.11-3.99 (m, 0.5H, $NCH_2CH$), 3.85-3.65 (m, 0.5H, $NCH_2CH_2$), 3.48-3.34 (m, 0.5H, $NCH_2CH_2$), 3.26-3.13 (m, 0.5H, $NCH_2CH_2$), 3.06 (s, 6H, $N(CH_3)_2$), 2.93-2.70 (m, 1.5H, $NCH_2CH_2$, $NH_2$), 2.46-2.32 (m, 1H, $NCH_2CHCH_2$), 2.31-2.19 (m, 1H, $NCH_2CHCH_2$), 2.06-1.92 (m, 1H, $NCH_2CH_2$), 1.83-1.65 (m, 1H, $NCH_2CH_2$); HRMS (ESI): m/z $[M+H]^+$. Calcd for $C_{29}H_{31}N_8O_4$: 555.2468; found: 555.2470.

Example 15

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-4-(diethylamino) benzamide (I-15)

Synthesis of 4-(diethylamino)-N-(7-(4,4,5,5-tetramethyl-1,3,2-dioxaborolane-2-)benzo[d][1,3]dioxo heterocyclopenten-4-)benzamide (IV-15)

Using compound XI (1.00 g, 3.80 mmol) and 4-diethylaminobenzoic acid (1.10 g, 5.70 mmol) as raw materials, the operation process was the same as that of compound IV-2 to obtain 2.04 g of brown oil product, which was directly fed into next step without further purification.

Synthesis of (R)-3-(4-amino-3-(7-(4-(diethylamino) benzamido) benzo[d][1,3]dioxo heterocyclopenten-4)-1H-pyrazolo[3,4-d]pyrimidin-1-yl)piperidine-1-tert-butyl formate (V-15)

Using compounds III-1 (0.80 g, 1.80 mmol) and IV-15 (0.95 g, 2.16 mmol) as raw materials, the operation process was the same as that of compound V-1 to obtain 657 mg of a light-yellow solid with a yield of 58.0%, m.p. at 116-118° C. $^1$H-NMR (300 MHz, $CDCl_3$) δ (ppm): 8.35 (s, 1H, ArH), 8.06 (d, J=8.25 Hz, 1H, ArH), 7.83-7.76 (m, 3H, ArH, NH), 7.12 (d, J=8.52 Hz, 1H, ArH), 6.69 (d, J=8.43 Hz, 2H, ArH), 6.12 (s, 2H, $OCH_2O$), 6.03 (s, 2H, $NH_2$), 4.89-4.78 (m, 1H, $CHC\underline{H}_2NBoc$), 4.37-4.26 (m, 1H, $CHC\underline{H}_2NBoc$), 4.17-4.10 (m, 1H, $CHC\underline{H}_2NBoc$), 3.47-3.39 (m, 5H, $NC\underline{H}_2CH_2$, $N(C\underline{H}_2CH_3)_2$), 2.87-2.80 (m, 1H, $NC\underline{H}_2CH_2$), 2.25-2.15 (m, 2H, $NCH_2CHC\underline{H}_2$), 1.91-1.84 (m, 1H, $NCH_2C\underline{H}_2$), 1.72-1.66 (m, 1H, $NCH_2C\underline{H}_2$), 1.45 (s, 9H, NBoc), 1.24-1.19 (m, 6H, $N(CH_2C\underline{H}_3)_2$).

Synthesis of (R)—N-(7-(4-amino-1-(piperidin-3)-1H-pyrazolo[3,4-d]pyrimidin-3-)benzo[d][1,3]dioxo heterocyclopenten-4)-4-(diethylamino)benzamide (VI-15)

Using compound V-15 (657 mg, 1.05 mmol) as the raw material, the operation process was the same as that of compound VI-1 to obtain 328 mg of a light-yellow solid with a yield of 59.4%, which was directly used in the next step without further purification.

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-4-(diethylamino) benzamide (I-15)

Using compound VI-15 (300 mg, 0.57 mmol) and acryloyl chloride (54 mg, 0.60 mmol) as raw materials, the procedure was the same as that of compound I-1 to obtain 209 mg of a white solid with a yield of 63.2%, m.p. at 158-160° C. $^1$H-NMR (300 MHz, $CDCl_3$) δ (ppm): 8.34 (s, 1H, ArH), 8.06-7.95 (m, 1H, ArH), 7.92-7.85 (m, 1H, ArH), 7.85-7.73 (m, 2H, ArH, NH), 7.18-7.03 (m, 1H, ArH), 6.77-6.51 (m, 3H, ArH, $CH{=}CH_2$), 6.39-6.22 (m, 1H, $CH{=}CH_2$), 6.11 (s, 2H, $OCH_2O$), 6.00 (s, 1H, $NH_2$), 5.79-5.61 (m, 1H, $CH{=}CH_2$), 4.98-4.79 (m, 1.5H, $NC\underline{H}_2C\underline{H}$), 4.72-4.55 (m, 0.5H, $NCH_2C\underline{H}$), 4.31-4.16 (m, 0.5H, $NC\underline{H}_2CH$), 4.12-3.96 (m, 0.5H, $NC\underline{H}_2CH$), 3.87-3.71 (m, 0.5H, $NC\underline{H}_2CH_2$), 3.53-3.30 (m, 4H, $N(C\underline{H}_2CH_3)_2$), 3.28-3.12 (m, 0.5H, $NC\underline{H}_2CH_2$), 2.94-2.77 (m, 0.5H, $NC\underline{H}_2CH_2$), 2.46-2.20 (m, 3.5H, $NC\underline{H}_2CH_2$, $NCH_2CHC\underline{H}_2$, $NH_2$), 2.08-1.91 (m, 1H, $NCH_2C\underline{H}_2$), 1.84-1.63 (m, 1H, $NCH_2C\underline{H}_2$), 1.31-1.15 (m, 6H, $N(CH_2CH_3)_2$); HRMS (ESI): m/z $[M+H]^+$. Calcd for $C_{31}H_{35}N_8O_4$: 583.2781; found: 583.2777.

Example 16

Synthesis of (R)—N-(7-(1-(1-acryloylpiperidin-3)-4-amino-1H-pyrazolo[3,4-d]pyrimidin-3-yl)benzo[d][1,3]dioxo heterocyclopenten-4-)-3-chlorobenzo[b]thiophene-2-formamide (I-16)

Synthesis of 3-chloro-N-(7-(4,4,5,5-tetramethyl-1,3,2-dioxaborolane-2)benzo[d][1,3]dioxo heterocyclopenten-4-)benzo[b]thiophene-2-carboxamide (IV-16)

Using compound XI (800 g, 3.04 mmol) and 3-Chlorobenzo[b]thiophene-2-carboxylic acid (1.00 g, 4.70 mmol) as raw materials, the operation process was the same as that of compound IV-2 to obtain 1.02 g of a yellow solid with a yield of 73.4%, which was directly fed into next step without further purification.

Synthesis of (R)-3-(4-amino-3-(7-(3-Chlorobenzo[b]thiophene-2-formamide)benzo[d][1,3]dioxo heterocyclopenten-4)-1H-tert-butyl-pyrazolo[3,4-d]pyrimidin-1-)piperidine-1-tert-butyl formate (V-16)

Using compounds III-1 (0.80 g, 1.80 mmol) and IV-16 (0.99 g, 2.16 mmol) as raw materials, the operation process was the same as that of compound V-1 to obtain 998 mg of a light-yellow solid with a yield of 85.3%, m.p. at 218-220° C. $^1$H-NMR (300 MHz, $CDCl_3$) δ (ppm): 9.13 (s, 1H, NH), 8.36 (s, 1H, ArH), 8.08 (d, J=8.85 Hz, 1H, ArH), 7.97-7.85 (m, 2H, ArH), 7.58-7.50 (m, 2H, ArH), 7.16 (d, J=8.73 Hz, 1H, ArH), 6.19 (s, 2H, $OCH_2O$), 5.94 (s, 2H, $NH_2$), 4.94-4.76 (m, 1H, $CHC\underline{H}_2NBoc$), 4.42-4.24 (m, 1H, $C\underline{H}CH_2NBoc$), 4.22-4.07 (m, 1H, $CHC\underline{H}_2NBoc$), 3.56-3.31 (m, 1H, $NC\underline{H}_2CH_2$), 2.93-2.74 (m, 1H, $NC\underline{H}_2CH_2$), 2.51-2.35 (m, 1H, $NCH_2CHC\underline{H}_2$), 2.24-2.12 (m, 1H, $NCH_2CHC\underline{H}_2$), 1.96-1.80 (m, 1H, $NCH_2C\underline{H}_2$), 1.78-1.64 (m, 1H, $NC\underline{H}_2CH_2$), 1.45 (s, 9H, $3CH_3$).

Synthesis of (R)—N-(7-(4-amino-1-(piperidin-3)-1H-pyrazolo[3,4-d]pyrimidin-3-)benzo[d][1,3]dioxo heterocyclopenten-4)-3-chlorobenzo[b]thiophene-2-formamide (VI-16)

Using compound V-16 (1.77 g, 1.47 mmol) as the starting material, the operation process was the same as that of compound VI-1 to obtain 797 mg of a light-yellow solid, which was directly used in the next step without further purification.

Synthesis of (R)—N-(7-(1-(1-acryloylpiperidin-3)-4-amino-1H-pyrazolo[3,4-d]pyrimidin-3-yl)benzo[d][1,3]dioxo heterocyclopenten-4-)-3-chlorobenzo[b]thiophene-2-formamide (I-16)

Using compound VI-16 (500 mg, 0.91 mmol) and acryloyl chloride (87 mg, 0.96 mmol) as raw materials, the procedure was the same as that of compound I-1 to obtain 312 mg of a white solid with a yield of 56.8%, m.p. at 172-174° C. $^1$H-NMR (400 MHz, $CDCl_3$) δ (ppm): 9.13 (s, 1H, NH), 8.36 (s, 1H, ArH), 8.08 (d, J=8.64 Hz, 1H, ArH), 7.97-7.91 (m, 1H, ArH), 7.91-7.85 (m, 1H, ArH), 7.59-7.48 (m, 2H, ArH), 7.15 (d, J=8.68 Hz, 1H, ArH), 6.67-6.54 (m, 1H, $CH{=}CH_2$), 6.36-6.24 (m, 1H, $CH{=}CH_2$), 6.19 (s, 2H, $OCH_2O$), 5.89 (s, 1H, $NH_2$), 5.77-5.61 (m, 1H, $CH{=}CH_2$), 4.96-4.80 (m, 1.5H, $NC\underline{H}_2C\underline{H}$), 4.69-4.59 (m, 0.5H, $NCH_2C\underline{H}$), 4.28-4.16 (m, 0.5H, $NC\underline{H}_2CH$), 4.09-3.97 (m, 0.5H, $NC\underline{H}_2CH$), 3.86-3.73 (m, 0.5H, $NC\underline{H}_2CH_2$), 3.47-3.34

(m, 0.5H, $NC\underline{H}_2CH_2$), 3.26-3.15 (m, 0.5H, $NC\underline{H}_2CH_2$), 2.93-2.80 (m, 0.5H, $NC\underline{H}_2CH_2$), 2.50-2.34 (m, 1H, $NCH_2CHC\underline{H}_2$), 2.31-2.22 (m, 2H, $NCH_2CHC\underline{H}_2$, $NH_2$), 2.06-1.93 (m, 1H, $NCH_2C\underline{H}_2$), 1.81-1.66 (m, 1H, $NCH_2C\underline{H}_2$); $^{13}$C-NMR (101 MHz, $CDCl_3$) δ (ppm): 165.71, 158.68, 157.87, 155.78, 155.56, 154.14, 145.15, 138.71, 138.35, 137.56, 136.90, 132.84, 127.96, 127.70, 125.71, 123.42, 123.27, 122.93, 122.22, 119.39, 115.63, 111.52, 102.26, 99.65, 53.75 (0.5C), 52.65 (0.5C), 49.97 (0.5C), 46.02 (0.5C), 45.87 (0.5C), 42.12 (0.5C), 30.31 (0.5C), 30.05 (0.5C), 25.25 (0.5C), 23.99 (0.5C); HRMS (ESI): m/z $[M+H]^+$. Calcd for $C_{29}H_{25}ClN_7O_4S$: 602.1377; found: 602.1378.

Example 17

Synthesis of (R)—N-(7-(1-(1-acryloylpiperidin-3-yl)-4-amino-1H-pyrazolo[3,4-d]pyrimidin-3-)benzo[d][1,3]dioxo heterocyclopenten-4-)-1-naphthalenecarboxamide (I-17)

Synthesis of N-(7-(4,4,5,5-tetramethyl-1,3,2-dioxaborolane-2-yl)benzo[d][1,3]dioxo heterocyclopenten-4-)-1-naphthalenecarboxamide (IV-17)

Using compound XI (1.00 g, 3.80 mmol) and 1-naphthoyl chloride (1.09 g, 5.70 mmol) as raw materials, the operation process was the same as that of compound IV-1 to obtain 1.47 g of red-brown solid with a yield of 93.0%, m.p. at 174-176° C. $^1$H-NMR (300 MHz, $CDCl_3$) δ (ppm): 8.39 (d, J=7.65 Hz, 1H, ArH), 7.95 (d, J=7.92 Hz, 2H, ArH), 7.88 (d, J=6.99 Hz, 1H, ArH), 7.78 (s, 1H, NHCO), 7.74 (d, J=6.87 Hz, 1H, ArH), 7.60-7.52 (m, 2H, ArH), 7.52-7.42 (m, 1H, ArH), 7.31 (d, J=8.31 Hz, 1H, ArH), 6.01 (s, 2H, $OCH_2O$), 1.37 (s, 12H, $4CH_3$).

Synthesis of (R)-3-(3-(7-(1-naphthalenecarboxamido)benzo[d][1,3]dioxo heterocyclopenten-4)-4-amino-1H-pyrazolo[3,4-d]pyrimidin-1-)piperidine-1-tert-butyl formate (V-17)

Using compounds III-1 (0.80 g, 1.80 mmol) and IV-17 (0.90 g, 2.16 mmol) as raw materials, the operation process was the same as that of compound V-1 to obtain 751 mg of a light-yellow solid with a yield of 68.6%, m.p. at 144-146° C. $^1$H-NMR (300 MHz, $CDCl_3$) ((ppm): 8.45-8.40 (m, 1H, ArH), 8.36 (s, 1H, ArH), 8.14-8.07 (m, 1H, ArH), 8.00 (d, J=8.22 Hz, 1H, ArH), 7.95-7.90 (m, 1H, ArH), 7.87 (s, 1H, NH), 7.83-7.77 (m, 1H, ArH), 7.62-7.56 (m, 2H, ArH), 7.56-7.52 (m, 1H, ArH), 7.18 (d, J=8.67 Hz, 1H, ArH), 6.10 (s, 2H, $OCH_2O$), 5.91 (s, 2H, $NH_2$), 4.92-4.78 (m, 1H, $CHC\underline{H}_2NBoc$), 4.39-4.23 (m, 1H, $C\underline{H}CH_2NBoc$), 4.21-4.07 (m, 1H, $CHC\underline{H}_2NBoc$), 3.56-3.32 (m, 1H, $NC\underline{H}_2CH_2$), 2.92-2.75 (m, 1H, $NC\underline{H}_2CH_2$), 2.23-2.14 (m, 2H, $NCH_2CHC\underline{H}_2$), 1.97-1.82 (m, 1H, $NC\underline{H}_2CH_2$), 1.77-1.63 (m, 1H, $NCH_2C\underline{H}_2$), 1.45 (s, 9H, NBoc).

Synthesis of (R)—N-(7-(4-amino-1-(piperidin-3)-1H-pyrazolo[3,4-d]pyrimidin-3-)benzo[d][1,3]dioxo heterocyclopenten-4-)-1-naphthalenecarboxamide (VI-17)

Using compound V-17 (700 mg, 1.15 mmol) as the raw material, the operation process was the same as that of compound VI-1 to obtain 498 mg of a light-yellow solid with a yield of 85.2%, which was directly used in the next step without further purification.

Synthesis of (R)—N-(7-(1-(1-acryloylpiperidin-3-yl)-4-amino-1H-pyrazolo[3,4-d]pyrimidin-3-)benzo[d][1,3]dioxo heterocyclopenten-4-)-1-naphthalenecarboxamide (I-17)

Using compound VI-17 (441 mg, 0.87 mmol) and acryloyl chloride (83 mg, 0.91 mmol) as raw materials, the procedure was the same as that of compound I-1 to obtain 214 mg of a white solid with a yield of 43.8%, m.p. at 172.0-174° C. $^1$H-NMR (300 MHz, $CDCl_3$) δ (ppm): 8.42 (d, J=7.98 Hz, 1H, ArH), 8.35 (s, 1H, ArH), 8.09 (d, J=7.38 Hz, 1H, ArH), 8.00 (d, J=8.16 Hz, 1H, ArH), 7.96-7.87 (m, 2H, ArH, NH), 7.80 (d, J=6.72 Hz, 1H, ArH), 7.68-7.47 (m, 3H, ArH), 7.17 (d, J=8.55 Hz, 1H, ArH), 6.68-6.51 (m, 1H, $CH{=}CH_2$), 6.34-6.21 (m, 1H, $CH{=}CH_2$), 6.10 (s, 2H, $OCH_2O$), 5.88 (s, 1H, $NH_2$), 5.75-5.61 (m, 1H, $CH{=}CH_2$), 4.98-4.80 (m, 1.5H, $NC\underline{H}_2C\underline{H}$), 4.67-4.54 (m, 0.5H, $NCH_2C\underline{H}$), 4.28-4.14 (m, 0.5H, $NC\underline{H}_2CH$), 4.07-3.94 (m, 0.5H, $N\underline{CH}_2CH$), 3.84-3.68 (m, 0.5H, $NC\underline{H}_2CH_2$), 3.42-3.29 (m, 0.5H, $NC\underline{H}_2CH_2$), 3.24-3.09 (m, 0.5H, $NC\underline{H}_2CH_2$), 2.94-2.78 (m, 0.5H, $NC\underline{H}_2CH_2$), 2.47-2.33 (m, 1H, $NCH_2CHC\underline{H}_2$), 2.30-2.19 (m, 1H, $NCH_2CHC\underline{H}_2$), 2.06 (s, 1H, $NH_2$), 2.02-1.92 (m, 1H, $NCH_2C\underline{H}_2$), 1.82-1.64 (m, 1H, $NCH_2C\underline{H}_2$); HRMS (ESI): m/z $[M+H]^+$. Calcd for $C_{31}H_{28}N_7O_4$: 562.2203; found: 562.2199.

Example 18

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-2-naphthalenecarboxamide (I-18)

Synthesis of N-(7-(4,4,5,5-tetramethyl-1,3,2-dioxaborolane-2-yl)benzo[d][1,3]dioxo heterocyclopenten-4-)-2-naphthalenecarboxamide (IV-18)

Using compound XI (1.00 g, 3.80 mmol) and 2-naphthoyl chloride (1.09 g, 5.70 mmol) as raw materials, the operation process was the same as that of compound IV-1 to obtain 1.51 g of a white solid with a yield of 95.2%, m.p. at 152-154° C. $^1$H-NMR (300 MHz, $CDCl_3$) δ (ppm): 8.40 (s, 1H, NH), 8.02-7.88 (m, 6H, ArH), 7.64-7.55 (m, 2H, ArH), 7.31 (d, J=8.58 Hz, 1H, ArH), 6.11 (s, 2H, $OCH_2O$), 1.37 (s, 12H, $4CH_3$).

Synthesis of (R)-3-(3-(7-(2-naphthalenecarboxamido)benzo[d][1,3]dioxo heterocyclopenten-4)-4-amino-1H-pyrazolo[3,4-d]pyrimidin-1-)piperidine-1-tert-butyl formate (V-18)

Using compounds III-1 (0.75 g, 1.69 mmol) and IV-18 (0.85 g, 2.03 mmol) as raw materials, the operation process was the same as that of compound V-1 to obtain 757 mg of a light-yellow solid with a yield of 73.8%, m.p. at 118-120° C. $^1$H-NMR (300 MHz, $CDCl_3$) δ (ppm): 8.44 (s, 1H, ArH), 8.37 (s, 1H, ArH), 8.12-8.04 (m, 2H, ArH, NH), 8.02-7.89 (m, 4H, ArH), 7.67-7.55 (m, 2H, ArH), 7.17 (d, J=8.76 Hz, 1H, ArH), 6.16 (s, 2H, $OCH_2O$), 5.76 (s, 2H, $NH_2$), 4.94-4.78 (m, 1H, $CHC\underline{H}_2NBoc$), 4.42-4.24 (m, 1H, $C\underline{H}CH_2NBoc$), 4.21-4.04 (m, 1H, $CHC\underline{H}_2NBoc$), 3.57-3.37 (m, 1H, $NC\underline{H}_2CH_2$), 2.92-2.75 (m, 1H, $NC\underline{H}_2CH_2$), 2.34-

2.14 (m, 2H, $NCH_2CHCH_2$), 1.95-1.82 (m, 1H, $NCH_2CH_2$), 1.77-1.62 (m, 1H, $NCH_2CH_2$), 1.45 (s, 9H, NBoc).

Synthesis of (R)—N-(7-(4-amino-1-(piperidin-3)-1H-pyrazolo[3,4-d]pyrimidin-3)benzo[d][1,3]dioxo heterocyclopenten-4)-2-naphthalenecarboxamide (VI-18)

Using compound V-18 (700 mg, 1.15 mmol) as the starting material, the operation process was the same as that of compound VI-1 to obtain 448 mg of a light-yellow solid with a yield of 76.6%.

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-2-naphthalenecarboxamide (I-18)

Using compound VI-18 (420 mg, 0.83 mmol) and acryloyl chloride (79 mg, 0.87 mmol) as raw materials, the procedure was the same as that of compound I-1 to obtain 247 mg of a white solid with a yield of 53.1%, m.p. at 172.5-174° C. $^1$H-NMR (300 MHz, $CDCl_3$) δ (ppm): 8.44 (s, 1H, ArH), 8.39-8.30 (m, 1H, ArH), 8.30-8.22 (m, 1H, ArH), 8.05-7.86 (m, 4H, ArH), 7.68-7.53 (m, 2H, ArH), 7.14 (d, J=8.25 Hz, 1H, ArH), 6.68-6.51 (m, 1H, $CH{=}CH_2$), 6.37-6.22 (m, 1H, $CH{=}CH_2$), 6.14 (s, 2H, $OCH_2O$), 5.97 (br, 1H, $NH_2$), 5.77-5.61 (m, 1H, $CH{=}CH_2$), 4.97-4.77 (m, 1.5H, $NCH_2CH$), 4.68-4.55 (m, 0.5H, $NCH_2CH$), 4.27-4.15 (m, 0.5H, $NCH_2CH$), 4.09-3.95 (m, 0.5H, $NCH_2CH$), 3.86-3.69 (m, 0.5H, $NCH_2CH_2$), 3.44-3.29 (m, 0.5H, $NCH_2CH_2$), 3.26-3.09 (m, 0.5H, $NCH_2CH_2$), 2.93-2.76 (m, 0.5H, $NCH_2CH_2$), 2.49-2.31 (m, 1H, $NCH_2CHCH_2$), 2.30-2.11 (m, 2H, $NCH_2CHCH_2$, $NH_2$), 2.03-1.91 (m, 1H, $NCH_2CH_2$), 1.79-1.62 (m, 1H, $NCH_2CH_2$); RMS (ESI): m/z $[M+H]^+$. Calcd for $C_{31}H_{28}N_7O_4$: 562.2203; found: 562.2205.

Example 19

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-4-methyl-1-naphthalenecarboxamide (1-19)

Synthesis of 4-methyl-N-(7-(4,4,5,5-tetramethyl-1,3,2-dioxaborolane-2-yl)benzo[d][1,3]dioxo heterocyclopenten-4-)-1-naphthalenecarboxamide (IV-19)

Using compound XI (1.00 g, 3.80 mmol) and 4-methyl-1-naphthalenecarboxylic acid (1.06 g, 5.70 mmol) as raw materials, the operation process was the same as that of compound IV-2 to obtain 1.52 g of a light-yellow solid with a yield of 92.7%, m.p. at 142-144° C. $^1$H-NMR (300 MHz, $CDCl_3$) δ (ppm): 8.48-8.39 (m, 1H, ArH), 8.09-8.01 (m, 1H, ArH), 8.00-7.92 (m, 1H, ArH), 7.71 (s, 1H, NHCO), 7.65 (d, J=6.87 Hz, 1H, ArH), 7.61-7.53 (m, 2H, ArH), 7.38-7.27 (m, 2H, ArH), 6.02 (s, 2H, $OCH_2O$), 2.74 (s, 3H, $CH_3$), 1.37 (s, 12H, $4CH_3$).

Synthesis of (R)-3-(4-amino-3-(7-(4-methyl-1-naphthalenecarboxamido)benzo [d][1,3]dioxo heterocyclopenten-4)-1H-pyrazolo[3,4-d]pyrimidin-1-yl) piperidine-1-tert-butyl formate (V-19)

Using compounds III-1 (0.73 g, 1.65 mmol) and IV-19 (1.07 g, 2.48 mmol) as raw materials, the operation process was the same as that of compound V-1 to obtain 719 mg of a light-yellow solid with a yield of 70.0%, m.p. at 140-142° C. $^1$H-NMR (300 MHz, $CDCl_3$) δ (ppm): 8.48-8.38 (m, 1H, ArH), 8.29 (s, 1H, ArH), 8.22 (s, 1H, NH), 8.07-7.98 (m, 1H, ArH), 7.97-7.88 (m, 1H, ArH), 7.64 (d, J=7.11 Hz, 1H, ArH), 7.60-7.49 (m, 2H, ArH), 7.28 (d, J=7.35 Hz, 1H, ArH), 7.10 (d, J=8.49 Hz, 1H, ArH), 6.24 (br, 2H, $NH_2$), 6.03 (s, 2H, $OCH_2O$), 4.86-4.73 (m, 1H, $CHCH_2NBoc$), 4.41-4.22 (m, 1H, $CHCH_2NBoc$), 4.17-3.99 (m, 1H, $CHCH_2NBoc$), 3.52-3.24 (m, 1H, $NCH_2CH_2$), 2.82-2.61 (m, 4H, $NCH_2CH_2$, $CH_3$), 2.31-2.07 (m, 2H, $NCH_2CHCH_2$), 1.92-1.76 (m, 1H, $NCH_2CH_2$), 1.74-1.57 (m, 1H, $NCH_2CH_2$), 1.44 (s, 9H, NBoc).

Synthesis of (R)—N-(7-(4-amino-1-(piperidin-3)-1H-pyrazolo[3,4-d]pyrimidin-3-)benzo[d][1,3]dioxo heterocyclopenten-4)-4-methyl-1-naphthalenecarboxamido (VI-19)

Using compound V-19 (700 mg, 1.13 mmol) as the raw material, the operation process was the same as that of compound VI-1 to obtain 548 mg of a light-yellow solid with a yield of 93.4%, which was directly used in the next step without further purification.

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-4-methyl-1-naphthalenecarboxamide (1-19)

Using compound VI-19 (500 mg, 0.96 mmol) and acryloyl chloride (91 mg, 1.01 mmol) as raw materials, the procedure was the same as that of compound I-1 to obtain 289 mg of a white solid with a yield of 53.3%, m.p. at 178-179° C. $^1$H-NMR (300 MHz, $CDCl_3$) δ (ppm): 8.44 (s, 1H, ArH), 8.31 (d, J=7.62 Hz, 1H, ArH), 8.21-7.92 (m, 3H, ArH, NH), 7.68 (d, J=6.48 Hz, 1H, ArH), 7.64-7.49 (m, 2H, ArH), 7.33 (d, J=6.09 Hz, 1H, ArH), 7.13 (d, J=7.17 Hz, 1H, ArH), 6.66-6.48 (m, 1H, $CH{=}CH_2$), 6.31-6.20 (m, 1H, $CH{=}CH_2$), 6.17-5.98 (m, 3H, $OCH_2O$, $NH_2$), 5.75-5.57 (m, 1H, $CH{=}CH_2$), 4.95-4.76 (m, 1.5H, $NCH_2CH$), 4.67-4.50 (m, 0.5H, $NCH_2CH$), 4.29-4.09 (m, 0.5H, $NCH_2CH$), 4.08-3.89 (m, 0.5H, $NCH_2CH$), 3.83-3.64 (m, 0.5H, $NCH_2CH_2$), 3.42-3.26 (m, 0.5H, $NCH_2CH_2$), 3.22-3.08 (m, 0.5H, $NCH_2CH_2$), 2.90-2.79 (m, 0.5H, $NCH_2CH_2$), 2.73 (s, 3H, $CH_3$), 2.56-2.17 (m, 3H, $NCH_2CHCH_2$, $NH_2$), 2.03-1.87 (m, 1H, $NCH_2CH_2$), 1.78-1.58 (m, 1H, $NCH_2CH_2$); HRMS (ESI): m/z $[M+H]^+$. Calcd for $C_{32}H_{30}N_7O_4$: 576.2359; found: 576.2357.

Example 20

Synthesis of (R)—N-(7-(1-(1-acryloylpiperidin-3-yl)-4-amino-1H-pyrazolo[3,4-d]pyrimidin-3-)benzo[d][1,3]dioxo heterocyclopenten-4-)-5,6,7,8-tetrahydronaphthalene-1-carboxamide (I-20)

Synthesis of N-(7-(4,4,5,5-tetramethyl-1,3,2-dioxaborolane-2-yl)benzo[d][1,3]dioxo heterocyclopenten-4)-5,6,7,8-tetrahydronaphthalene-1-carboxamide (IV-20)

Using compound XI (1.00 g, 3.80 mmol) and 5,6,7,8-tetrahydronaphthalene-1-carboxamid (1.00 g, 5.70 mmol) as raw materials, the operation process was the same as that of compound IV-2 to obtain 1.51 g of a white solid with a yield of 94.4%, m.p. at 168-170° C. $^1$H-NMR (300 MHz, $CDCl_3$)

δ (ppm): 7.92 (d, J=8.37 Hz, 1H, ArH), 7.47 (s, 1H, NHCO), 7.33-7.27 (m, 2H, ArH), 7.21-7.14 (m, 2H, ArH), 6.04 (s, 2H, $OCH_2O$), 3.02-2.77 (m, 4H, $C\underline{H}_2CH_2CH_2C\underline{H}_2$), 1.88-1.73 (m, 4H, $CH_2C\underline{H}_2C\underline{H}_2CH_2$), 1.36 (s, 12H, $4CH_3$).

Synthesis of (R)-3-(4-amino-3-(7-(5,6,7,8-tetrahydronaphthalene-1-carboxamide)benzo[d][1,3]dioxo heterocyclopenten-4)-1H-pyrazolo[3,4-d]pyrimidin-1-)piperidine-1-tert-butyl formate (V-20)

Using compound III-1 (0.75 g, 1.69 mmol) and IV-20 (0.85 g, 2.03 mmol) as raw materials, the operation process was the same as that of compound V-1 to obtain 784 mg of a light-yellow solid with a yield of 75.9%, m.p. at 150-152° C. $^1$H-NMR (300 MHz, $CDCl_3$) δ (ppm): 8.36 (s, 1H, ArH), 8.05 (d, J=8.76 Hz, 1H, ArH), 7.56 (s, 1H, NH), 7.37-7.30 (m, 1H, ArH), 7.25-7.10 (m, 3H, ArH), 6.10 (s, 2H, $OCH_2O$), 5.80 (s, 2H, $NH_2$), 4.91-4.78 (m, 1H, $CHC\underline{H}_2NBoc$), 4.41-4.22 (m, 1H, $C\underline{H}CH_2NBoc$), 4.21-4.06 (m, 1H, $CHC\underline{H}_2NBoc$), 3.53-3.33 (m, 1H, $NC\underline{H}_2CH_2$), 3.05-2.91 (m, 2H, $CH_2C$), 2.90-2.76 (m, 3H, $CH_2C$, $NC\underline{H}_2CH_2$), 2.33-2.15 (m, 2H, $NCH_2CHC\underline{H}_2$), 1.96-1.86 (m, 1H, $NCH_2C\underline{H}_2$), 1.86-1.76 (m, 4H, $CCH_2C\underline{H}_2C\underline{H}_2CH_2C$), 1.74-1.63 (m, 1H, $NCH_2C\underline{H}_2$), 1.45 (s, 9H, NBoc).

Synthesis of (R)—N-(7-(4-amino-1-(piperidin-3)-1H-pyrazolo[3,4-d]pyrimidin-3-)benzo[d][1,3]dioxo heterocyclopenten-4)-5,6,7,8-tetrahydronaphthalene-1-carboxamide (VI-20)

Using compound V-20 (700 mg, 1.14 mmol) as the starting material, the operation process was the same as that of compound VI-1 to obtain 472 mg of a light-yellow solid with a yield of 80.62%.

Synthesis of (R)—N-(7-(1-(1-acryloylpiperidin-3-yl)-4-amino-1H-pyrazolo[3,4-d]pyrimidin-3-)benzo [d][1,3]dioxo heterocyclopenten-4-)-5,6,7,8-tetrahydronaphthalene-1-carboxamide (I-20)

Using compound VI-20 (420 mg, 0.82 mmol) and acryloyl chloride (78 mg, 0.86 mmol) as raw materials, the procedure was the same as that of compound I-1 to obtain 316 mg of a white solid with a yield of 68.1%, m.p. at 158-160° C. $^1$H-NMR (400 MHz, $CDCl_3$) ((ppm): 8.33 (s, 1H, ArH), 8.11-7.92 (m, 1H, ArH), 7.63 (s, 1H, NH), 7.38-7.29 (m, 1H, ArH), 7.24-7.15 (m, 2H, ArH), 7.12 (d, J=8.40 Hz, 1H, ArH), 6.67-6.50 (m, 1H, $CH{=}CH_2$), 6.34-6.20 (m, 1H, $CH{=}CH_2$), 6.09 (s, 2H, $OCH_2O$), 5.88 (br, 1H, $NH_2$), 5.75-5.58 (m, 1H, $CH{=}CH_2$), 4.97-4.75 (m, 1.5H, $NC\underline{H}_2C\underline{H}$), 4.69-4.52 (m, 0.5H, $NCH_2C\underline{H}$), 4.27-4.13 (m, 0.5H, $NC\underline{H}_2CH$), 4.10-3.94 (m, 0.5H, $NC\underline{H}_2CH$), 3.86-3.67 (m, 0.5H, $NC\underline{H}_2CH_2$), 3.45-3.29 (m, 0.5H, $NC\underline{H}_2CH_2$), 3.26-3.11 (m, 0.5H, $NC\underline{H}_2CH_2$), 3.03-2.90 (m, 2H, $C\underline{H}_2CH_2CH_2C\underline{H}_2$), 2.89-2.75 (m, 2.5H, $NC\underline{H}_2CH_2$, $C\underline{H}_2CH_2CH_2C\underline{H}_2$), 2.46-2.31 (m, 1H, $NCH_2CHC\underline{H}_2$), 2.30-2.20 (m, 1H, $NCH_2CHC\underline{H}_2$), 2.10 (br, 1H, $NH_2$), 2.03-1.91 (m, 1H, $NCH_2C\underline{H}_2$), 1.86-1.65 (m, 5H, $CH_2C\underline{H}_2C\underline{H}_2CH_2$, $NCH_2C\underline{H}_2$); HRMS (ESI): m/z $[M+H]^+$. Calcd for $C_{31}H_{32}N_7O_4$: 566.2516; found: 566.2512.

Example 21

Synthesis of (R)—N-(7-(7-(1-acryloylpiperidin-3-yl)-4-amino-7H-pyrrolo[2,3-d]pyrimidin-5-yl)benzo [d][1,3]dioxo heterocyclopenten-4-)-1-naphthalenecarboxamide (I-21)

Synthesis of (R)-3-(4-amino-5-iodo-7H-pyrrolo[2,3-d]pyrimidin-7-yl)piperidine-1-tert-butyl formate (III-3)

5-iodo-7H-pyrrolo[2,3-d]pyrimidine-4-amine (VII-2) (1.00 g, 3.85 mmol), (S)-1-tert-butoxycarbonyl-3-hydroxy piperidine (VIII-1) (1.55 g, 7.69 mmol), $PPh_3$ (2.02 g, 7.69 mmol), anhydrous THF (100 mL) were added to a 250 mL three-necked flask under nitrogen protection, the mixture was stirred for 30 minutes under an ice bath; then, DIAD (1.56 g, 7.69 mmol) was added. Next, the mixture was reacted at room temperature for 18 hours. The THF was distilled off, the residue was dissolved in ethyl acetate (100 mL), and washed successively with saturated sodium carbonate (30 mL×3), water (30 mL×3) and saturated sodium chloride (30 mL×3), and was dried by anhydrous $Na_2SO_4$. After suction filtration, the filtrate was evaporated to remove the solvent under reduced pressure to obtain a residue, which was separated by column chromatography (eluent: DCM: MeOH=150-60:1), 1.71 g of a white solid was obtained with a yield of 70.6%, m.p. at 126-128° C. $^1$H-NMR (300 MHz, $CDCl_3$) δ (ppm): 8.30 (s, 1H, ArH), 7.16 (s, 1H, ArH), 5.92 (s, 2H, $NH_2$), 4.82-4.66 (m, 1H, $NC\underline{H}_2CH$), 4.30-4.11 (m, 1H, $NCH_2C\underline{H}$), 4.07-3.94 (m, 1H, $NC\underline{H}_2CH$), 3.35-3.19 (m, 1H, $NC\underline{H}_2CH_2$), 3.10-2.93 (m, 1H, $NC\underline{H}_2CH_2$), 2.24-2.12 (m, 1H, $CHC\underline{H}_2CH_2$), 2.09-1.97 (m, 1H, $CHC\underline{H}_2CH_2$), 1.91-1.79 (m, 1H, $CHCH_2C\underline{H}_2$), 1.78-1.68 (m, 1H, $CHCH_2C\underline{H}_2$), 1.49 (s, 9H, $C(CH_3)_3$).

Synthesis of (R)-3-(5-(7-(1-naphthylamide)benzo[d][1,3]dioxol-4-yl)-4-amino-7H-pyrrolo[2,3-d]pyrimidin-7-yl) piperidine-1-carboxylate tert-butyl ester (V-21)

Using compounds III-3 (0.48 g, 1.08 mmol) and IV-17 (0.54 g, 1.30 mmol) as raw materials, the operation process was the same as that of compound V-1 to obtain 353 mg of a light-yellow solid with a yield of 53.7%, m.p. at 124-126° C.

Synthesis of (R)—N-(7-(4-amino-7-(piperidin-3)-7H-pyrrolo[2,3-d]pyrimidin-5-)benzo[d][1,3]dioxo heterocyclopenten-4)-1-naphthylformamide (VI-21)

Using compound V-21 (580 mg, 0.96 mmol) as the starting material, the operation process was the same as that of compound VI-1 to obtain 340 mg of a light-yellow solid with a yield of 70.2%, which was directly used in the next step without further purification.

Synthesis of (R)—N-(7-(7-(1-acryloylpiperidin-3-yl)-4-amino-7H-pyrrolo[2,3-d]pyrimidin-5-yl)benzo [d][1,3]dioxo heterocyclopenten-4-)-1-naphthalenecarboxamide (I-21)

Using compound VI-21 (337 mg, 0.67 mmol) and acryloyl chloride (65 mg, 0.70 mmol) as raw materials, the procedure was the same as that of compound I-1 to obtain 189 mg of a white solid with a yield of 50.7%, m.p. at 166-167.5° C. $^1$H-NMR (300 MHz, $CDCl_3$) δ (ppm): 8.43

(d, J=7.41 Hz, 1H, ArH), 8.31 (s, 1H, ArH), 8.06-7.96 (m, 2H, ArH), 7.94-7.84 (m, 2H, ArH), 7.79 (d, J=6.51 Hz, 1H, ArH), 7.65-7.46 (m, 3H, ArH, NH), 7.16 (s, 1H, ArH), 7.01 (d, J=8.49 Hz, 1H, ArH), 6.70-6.54 (m, 1H, $CH{=}CH_2$), 6.37-6.25 (m, 1H, $CH{=}CH_2$), 6.05 (s, 2H, $OCH_2O$), 5.78-5.65 (m, 1H, $CH{=}CH_2$), 5.40 (s, 1H, $NH_2$), 4.89-4.53 (m, 2H, $NCH_2CH$), 4.39-4.23 (m, 0.5H, $NCH_2CH$), 4.09-3.89 (m, 0.5H, $NCH_2CH$), 3.44-3.14 (m, 1.5H, $NCH_2CH_2$), 2.96-2.77 (m, 0.5H, $NCH_2CH_2$), 2.34-2.24 (m, 1H, $NCH_2CHCH_2$), 2.22-2.09 (m, 2H, $NCH_2CHCH_2$, $NH_2$), 2.02-1.88 (m, 1H, $NCH_2CH_2$), 1.82-1.65 (m, 1H, $NCH_2CH_2$); HRMS (ESI): m/z $[M+H]^+$. Calcd for $C_{32}H_{29}N_6O_4$: 561.2250; found: 561.2253.

Example 22

Synthesis of (R)—N-(7-(7-(1-acryloylpiperidin-3-yl)-4-amino-7H-pyrrolo[2,3-d]pyrimidin-5-yl)benzo[d][1,3]dioxo heterocyclopenten-4-)-2-naphthalenecarboxamide (I-22)

Synthesis of (R)-3-(5-(7-(1-naphthylamide)benzo[d][1,3]dioxol-4-yl)-4-amino-7H-pyrrolo[2,3-d]pyrimidin-7-yl) piperidine-1-carboxylate tert-butyl ester (V-22)

Using compounds III-3 (1.00 g, 2.26 mmol) and IV-18 (1.13 g, 2.71 mmol) as raw materials, the operation process was the same as that of compound V-1 to obtain 988 mg of a light-yellow solid with a yield of 72.2%, m.p. at 124-126° C. $^1$H-NMR (300 MHz, $CDCl_3$) δ (ppm): 8.43 (s, 1H, ArH), 8.33 (s, 1H, ArH), 8.09 (s, 1H, NH), 8.03-7.86 (m, 5H, ArH), 7.66-7.55 (m, 2H, ArH), 7.19 (s, 1H, ArH), 7.00 (d, J=8.91 Hz, 1H, ArH), 6.10 (s, 2H, $OCH_2O$), 5.36 (s, 2H, $NH_2$), 4.84-4.67 (m, 1H, $CHCH_2N$), 4.33-4.19 (m, 1H, $CHCH_2N$), 4.11-3.96 (m, 1H, $CHCH_2N$), 3.31-3.16 (m, 1H, $NCH_2CH_2$), 3.02-2.85 (m, 1H, $NCH_2CH_2$), 2.33-2.15 (m, 2H, $CHCH_2CH_2$), 2.08-1.99 (m, 1H, $CHCH_2CH_2$), 1.87-1.78 (m, 1H, $CHCH_2CH_2$), 1.46 (s, 9H, $C(CH_3)_3$).

Synthesis of (R)—N-(7-(4-Amino-7-(piperidin-3-yl)-7H-pyrrolo[2,3-d]pyrimidin-5-yl)benzo[d][1,3]Dioxol-4-yl)-2-naphthylcarboxamide (VI-22)

Using compound V-22 (988 mg, 1.63 mmol) as the starting material, the procedure was the same as that of compound VI-1 to obtain 825 mg of a light-yellow solid, which was directly used in the next step without further purification.

Synthesis of (R)—N-(7-(7-(1-acryloylpiperidin-3-yl)-4-amino-7H-pyrrolo[2,3-d]pyrimidin-5-yl)benzo[d][1,3]dioxo heterocyclopenten-4-)-2-naphthalenecarboxamide (I-22)

Using compound VI-22 (825 mg, 1.63 mmol) and acryloyl chloride (155 mg, 1.71 mmol) as raw materials, the procedure was the same as that of compound I-1 to obtain 356 mg of a white solid with a yield of 38.9%, m.p. at 149.5-151° C. $^1$H-NMR (400 MHz, $CDCl_3$) δ (ppm): 8.44 (s, 1H, ArH), 8.32 (s, 1H, ArH), 8.23 (s, 1H, NH), 8.01-7.88 (m, 5H, ArH), 7.68-7.53 (m, 2H, ArH), 7.23-7.12 (m, 1H, ArH), 6.99 (s, 1H, ArH), 6.70-6.57 (m, 1H, $CH{=}CH_2$), 6.38-6.27 (m, 1H, $CH{=}CH_2$), 6.10 (s, 2H, $OCH_2O$), 5.78-5.66 (m, 1H, $CH{=}CH_2$), 5.47 (s, 1H, $NH_2$), 4.91-4.67 (m, 1.5H, $NCH_2CH$), 4.67-4.55 (m, 0.5H, $NCH_2CH$), 4.39-4.27 (m, 0.5H, $NCH_2CH$), 4.08-3.94 (m, 0.5H, $NCH_2CH$), 3.45-3.33 (m, 0.5H, $NCH_2CH_2$), 3.31-3.15 (m, 1H, $NCH_2CH_2$), 2.92-2.79 (m, 0.5H, $NCH_2CH_2$), 2.42-2.26 (m, 2H, $NCH_2CHCH_2$, $NH_2$), 2.23-2.09 (m, 1H, $NCH_2CHCH_2$), 2.02-1.88 (m, 1H, $NCH_2CH_2$), 1.83-1.66 (m, 1H, $NCH_2CH_2$); HRMS (ESI): m/z $[M+H]^+$. Calcd for $C_{32}H_{29}N_6O_4$: 561.2250; found: 561.2254.

Example 23

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-2-phenylacetamide (I-23)

Synthesis of 2-phenyl-N-(7-(4,4,5,5-tetramethyl-1,3,2-dioxaborolane-2-yl)benzo[d][1,3]dioxo heterocyclopenten-4-)acetamide (IV-23)

Dissolve compound XI (500 mg, 1.90 mmol), phenylacetic acid (388 mg, 2.85 mmol) and 1H-benzotriazol-1-oxytripyrrolidinylphosphonium hexafluorophosphate (PyBOP) (1.48 g, 2.84 mmol) in DMF (6 mL), added DIEA (491 mg, 3.80 mmol), and then reacted at room temperature for 10 hours. The post-processing method was the same as that of compound IV-2 to obtain 215 mg of a white solid with a yield of 29.7%, m.p. at 152-154° C. $^1$H-NMR (300 MHz, $CDCl_3$) δ (ppm): 7.72 (d, J=8.10 Hz, 1H, ArH), 7.45-7.29 (m, 5H, ArH), 7.20 (d, J=8.46 Hz, 1H, ArH), 7.14 (s, 1H, CONH), 5.96 (s, 2H, $OCH_2O$), 3.76 (s, 2H, $COCH_2Ph$), 1.34 (s, 12H, $4CH_3$).

Synthesis of (R)-3-(4-amino-3-(7-(2-phenylacetamide)benzo[d][1,3]dioxo heterocyclopenten-4)-1H-tert-butyl-pyrazolo[3,4-d]pyrimidin-1-)piperidine-1-tert-butyl formate (V-23)

Using compounds III-1 (0.20 g, 0.45 mmol) and IV-23 (0.21 g, 0.54 mmol) as the raw materials, the operation process was the same as that of compound V-1 to obtain 125 mg of a light-yellow solid with a yield of 48.5%, m.p. at 130-132° C. $^1$H-NMR (300 MHz, $CDCl_3+D_2O$) δ (ppm): 8.33 (s, 1H, ArH), 7.83 (d, J=8.67 Hz, 1H, ArH), 7.46-7.30 (m, 5H, ArH), 7.05 (d, J=8.70 Hz, 1H, ArH), 6.00 (s, 2H, $OCH_2O$), 4.90-4.75 (m, 1H, $CHCH_2NBoc$), 4.38-4.21 (m, 1H, $CHCH_2NBoc$), 4.18-4.03 (m, 1H, $CHCH_2NBoc$), 3.78 (s, 2H, $COCH_2Ph$), 3.49-3.29 (m, 1H, $NCH_2CH_2$), 2.89-2.74 (m, 1H, $NCH_2CH_2$), 2.31-2.10 (m, 2H, $NCH_2CHCH_2$), 1.91-1.77 (m, 1H, $NCH_2CH_2$), 1.74-1.57 (m, 1H, $NCH_2CH_2$), 1.43 (s, 9H, NBoc).

Synthesis of (R)—N-(7-(4-amino-1-(piperidin-3)-1H-pyrazolo[3,4-d]pyrimidin-3)benzo[d][1,3]dioxo heterocyclopenten-4)-2-phenylacetamide (VI-23)

Using compound V-23 (0.21 g, 0.37 mmol) as the starting material, the operation process was the same as that of compound VI-1 to obtain 136 mg ofa light-yellow solid with a yield of 78.51%.

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-2-phenylacetamide (I-23)

Using compound VI-23 (136 mg, 0.29 mmol) and acryloyl chloride (31 mg, 0.34 mmol) as raw materials, the procedure was the same as compound I-1 to obtain 61 mg of a white solid with a yield of 40.4%, m.p. at 118-119.5° C. $^1$H-NMR (300 MHz, CDCl3) δ (ppm): 8.36 (s, 1H, ArH), 7.87 (d, J=7.20 Hz, 1H, ArH), 7.51-7.33 (m, 5H, ArH, NH), 7.23 (s, 1H, NH), 7.08 (d, J=8.46 Hz, 1H, ArH), 6.70-6.52 (m, 1H, $CH{=}CH_2$), 6.37-6.23 (m, 1H, $CH{=}CH_2$), 6.03 (s, 2H, $OCH_2O$), 5.78-5.60 (m, 3H, $CH{=}CH_2$, $NH_2$), 4.94-4.82 (m, 1H, $NCH_2CH$), 4.70-4.56 (m, 0.5H, $NCH_2CH$), 4.29-4.13 (m, 0.5H, $NCH_2CH$), 4.10-3.96 (m, 0.5H, $NCH_2CH$), 3.88-3.73 (m, 2.5H, $NCH_2CH$, $COCH_2Ph$), 3.46-3.30 (m, 0.5H, $NCH_2CH_2$), 2.96-2.81 (m, 0.5H, $NCH_2CH_2$), 2.50-2.35 (m, 1H, $NCH_2CH_2$), 2.32-2.25 (m, 1H, $NCH_2CHCH_2$), 2.08-1.94 (m, 1H, $NCH_2CHCH_2$), 1.93-1.87 (m, 1H, $NCH_2CH_2$), 1.76-1.66 (m, 1H, $NCH_2CH_2$); HRMS (ESI): m/z $[M+H]^+$. Calcd for $C_{28}H_{28}N_7O_4$: 526.2203; found: 526.2199.

Example 24

Synthesis of (R)—N-(7-(1-(1-acryloylpiperidin-3-yl)-4-amino-1H-pyrazolo[3,4-d]pyrimidin-3-)benzo[d][1,3]dioxo heterocyclopenten-4-)-[1,1'-Biphenyl]-4-carboxamide (I-24)

Synthesis of N-(7-(4,4,5,5-tetramethyl-1,3,2-dioxaborolan-2-yl)benzo[d][1,3]dioxo heterocyclopenten-4-)-[1,1'-Biphenyl]-4-carboxamide (IV-24)

Using compound XI (1.00 g, 3.80 mmol) and 4-phenylbenzoic acid (1.13 g, 5.70 mmol) as raw materials, the operation process was the same as that of compound IV-2 to obtain 1.48 g of a white solid with a yield of 88.1%, m.p. at 120-122° C. $^1$H-NMR (300 MHz, $CDCl_3$) δ (ppm): 8.00-7.88 (m, 4H, ArH), 7.72 (d, J=8.01 Hz, 2H, ArH), 7.63 (d, J=6.96 Hz, 2H, ArH), 7.52-7.45 (m, 2H, ArH, NH), 7.43-7.40 (m, 1H, ArH), 7.30 (d, J=8.64 Hz, 1H, ArH), 6.09 (s, 2H, $OCH_2O$), 1.37 (s, 12H, $4CH_3$).

Synthesis of (R)-3-(3-(7-([1,1'-Biphenyl]-4-ylcarboxamido)benzo[d][1,3]dioxo heterocyclopenten-4)-4-amino-1H-pyrazolo[3,4-d]pyrimidin-1-)piperidine-1-tert-butyl formate (V-24)

Using compounds III-1 (0.80 g, 1.80 mmol) and IV-24 (0.96 g, 2.16 mmol) as raw materials, the operation process was the same as that of compound V-1 to obtain 821 mg of a light-yellow solid with a yield of 71.9%, m.p. at 151-152° C. $^1$H-NMR (300 MHz, $CDCl_3+D_2O$) δ (ppm): 8.36 (s, 1H, ArH), 8.09-7.95 (m, 3H, ArH), 7.79-7.72 (m, 2H, ArH), 7.69-7.61 (m, 2H, ArH), 7.54-7.38 (m, 3H, ArH), 7.16 (d, J=8.16 Hz, 1H, ArH), 6.15 (s, 2H, $OCH_2O$), 4.96-4.76 (m, 1H, $CHCH_2NBoc$), 4.40-4.23 (m, 1H, $CHCH_2NBoc$), 4.19-4.08 (m, 1H, $CHCH_2NBoc$), 3.59-3.25 (m, 1H, $NCH_2CH_2$), 2.96-2.74 (m, 1H, $NCH_2CH_2$), 2.38-2.15 (m, 2H, $NCH_2CHCH_2$), 1.94-1.86 (m, 1H, $NCH_2CH_2$), 1.79-1.62 (m, 1H, $NCH_2CH_2$), 1.45 (s, 9H, NBoc).

Synthesis of (R)—N-(7-(4-amino-1-(piperidin-3)-1H-pyrazolo[3,4-d]pyrimidin-3-)benzo[d][1,3]dioxo heterocyclopenten-4-)[1,1'-Biphenyl]-4-carboxamide (VI-24)

Using compound V-24 (750 mg, 1.18 mmol) as the raw material, the operation process was the same as that of compound VI-1 to obtain 468 mg of a light-yellow solid with a yield of 74.1%, which was directly used in the next step without further purification.

Synthesis of (R)—N-(7-(1-(1-acryloylpiperidin-3-yl)-4-amino-1H-pyrazolo[3,4-d]pyrimidin-3-)benzo[d][1,3]dioxo heterocyclopenten-4-)-[1,1'-Biphenyl]-4-carboxamide (I-24)

Using compound VI-24 (416 mg, 0.78 mmol) and acryloyl chloride (74 mg, 0.82 mmol) as raw materials, the procedure was the same as that of compound I-1 to obtain 212 mg of a white solid with a yield of 46.3%, m.p. at 216-218° C. $^1$H-NMR (300 MHz, $CDCl_3$) δ (ppm): 8.37 (s, 1H, ArH), 8.14-7.94 (m, 4H, ArH, NH), 7.74 (d, J=7.65 Hz, 2H, ArH), 7.65 (d, J=7.65 Hz, 2H, ArH), 7.56-7.37 (m, 3H, ArH), 7.15 (d, J=8.67 Hz, 1H, ArH), 6.69-6.51 (m, 1H, $CH{=}CH_2$), 6.35-6.25 (m, 1H, $CH{=}CH_2$), 6.15 (s, 2H, $OCH_2O$), 5.77 (s, 1H, $NH_2$), 5.73-5.63 (m, 1H, $CH{=}CH_2$), 4.98-4.82 (m, 1.5H, $NCH_2CH$), 4.70-4.58 (m, 0.5H, $NCH_2CH$), 4.27-4.16 (m, 0.5H, $NCH_2CH$), 4.11-3.99 (m, 0.5H, $NCH_2CH$), 3.85-3.73 (m, 0.5H, $NCH_2CH_2$), 3.47-3.35 (m, 0.5H, $NCH_2CH_2$), 3.26-3.14 (m, 0.5H, $NCH_2CH_2$), 2.94-2.80 (m, 0.5H, $NCH_2CH_2$), 2.49-2.34 (m, 1H, $NCH_2CHCH_2$), 2.31-2.21 (m, 1H, $NCH_2CHCH_2$), 2.07-1.94 (m, 1H, $NCH_2CH_2$), 1.88 (s, 1H, $NH_2$), 1.78-1.65 (m, 1H, $NCH_2CH_2$); HRMS (ESI): m/z $[M+H]^+$. Calcd for $C_{33}H_{30}N_7O_4$: 588.2359; found: 588.2359.

Example 25

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-4-methoxybenzenesulfonamide (I-25)

Synthesis of 4-methoxy-N-(7-(4,4,5,5-tetramethyl-1,3,2-dioxaborolan-2-)benzo[d][1,3]dioxo heterocyclopenten-4-)benzene sulfonamide (IV-25)

Compound XI (1.00 g, 3.80 mmol), pyridine (1.50 g, 19.00 mmol) and dichloromethane (20 mL) were mixed, and 4-methoxybenzenesulfonyl chloride (0.94 g, 4.56 mmol) in dichloromethane solution was added dropwise. Next, the mixture was reacted at room temperature for 8.5 hours. The post-processing method was the same as that of compound IV-1 to obtain 985 mg of a light-yellow solid with a yield of 59.7%, m.p. at 186-188° C. $^1$H-NMR (300 MHz, $CDCl_3$) ((ppm): 7.74 (d, J=8.67 Hz, 2H, ArH), 7.15 (d, J=8.37 Hz, 1H, ArH), 7.02 (d, J=8.28 Hz, 1H, ArH), 6.88 (d, J=8.55 Hz, 2H, ArH), 6.56 (s, 1H, NH), 5.88 (s, 2H, $OCH_2O$), 3.83 (s, 3H, $OCH_3$), 1.33 (s, 12H, $4CH_3$).

Synthesis of (R)-3-(4-amino-3-(7-(4-methoxybenzenesulfonamide)benzo [d][1,3]dioxo heterocyclopenten-4)-1H-pyrazolo[3,4-d]pyrimidin-1-yl)piperidine-1-tert-butyl formate (V-25)

Using compounds III-1 (1.00 g, 1.04 mmol) and IV-25 (0.54 g, 1.24 mmol) as raw materials, the operation process was the same as that of compound V-1 to obtain 592 mg of a light-yellow solid with a yield of 91.5%, m.p. at 182-184° C. $^1$H-NMR (300 MHz, $CDCl_3$) δ (ppm): 8.34 (s, 1H, ArH), 7.80 (d, J=8.85 Hz, 2H, ArH), 7.26 (s, 1H, NH), 7.19 (d, J=8.70 Hz, 1H, ArH), 7.03 (d, J=8.70 Hz, 1H, ArH), 6.94 (d, J=8.88 Hz, 2H, ArH), 5.95 (s, 2H, $OCH_2O$), 5.69 (s, 2H, $NH_2$), 4.89-4.77 (m, 1H, $CHCH_2NBoc$), 4.37-4.23 (m, 1H, $CHCH_2NBoc$), 4.19-4.08 (m, 1H, $CHCH_2NBoc$), 3.86 (s, 3H, OMe), 3.47-3.33 (m, 1H, $NCH_2CH_2$), 2.89-2.77 (m, 1H, $NC\underline{H_2}CH_2$), 2.27-2.11 (m, 2H, $NCH_2CHC\underline{H_2}$), 1.94-1.81 (m, 2H, $NCH_2C\underline{H_2}$), 1.44 (s, 9H, NBoc).

Synthesis of (R)—N-(7-(4-amino-1-(piperidin-3)-1H-pyrazolo[3,4-d]pyrimidin-3-)benzo[d][1,3]dioxo heterocyclopenten-4)-4-methoxybenzenesulfonamide (VI-25)

Using compound V-25 (500 mg, 0.80 mmol) as the raw material, the operation process was the same as that of compound VI-1 to obtain 741 mg of a light-yellow solid, which was directly used in the next step without further purification.

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-4-methoxybenzenesulfonamide (I-25)

Using compound VI-25 (500 mg, 0.96 mmol) and acrylic acid (91 mg, 1.00 mmol) as raw materials, the procedure was the same as that of compound I-4 to obtain 287 mg of a white solid with a yield of 52.0%, m.p. at 157.5-159.0° C. $^1H$-NMR (300 MHz, $CDCl_3$) δ (ppm): 8.32 (s, 1H, ArH), 7.80 (d, J=8.52 Hz, 2H, ArH), 7.18 (d, J=8.88 Hz, 1H, ArH), 7.02 (d, J=8.61 Hz, 1H, ArH), 6.94 (d, J=8.67 Hz, 2H, ArH), 6.68-6.49 (m, 1H, $CH{=}CH_2$), 6.34-6.21 (m, 1H, $\underline{CH}{=}\underline{CH_2}$), 5.95 (s, 2H, $OCH_2O$), 5.86 (s, 1H, $NH_2$), 5.75-5.60 (m, 1H, $CH{=}CH_2$), 4.96-4.77 (m, 1.5H, $NC\underline{H_2}C\underline{H}$), 4.66-4.53 (m, 0.5H, $NCH_2C\underline{H}$), 4.23-4.12 (m, 0.5H, $N\underline{CH_2}CH$), 4.08-3.97 (m, 0.5H, $N\underline{CH_2}C\underline{H}$), 3.86 (s, 3H, $OCH_3$), 3.53-3.43 (m, 0.5H, $NC\underline{H_2}CH_2$), 3.39-3.27 (m, 0.5H, $NC\underline{H_2}CH_2$), 3.24-3.10 (m, 0.5H, $NC\underline{H_2}CH_2$), 2.97-2.78 (m, 0.5H, $NC\underline{H_2}CH_2$), 2.46-2.19 (m, 2H, $NCH_2CHC\underline{H_2}$, $NH_2$), 2.11-1.91 (m, 2H, $NCH_2CHC\underline{H_2}C\underline{H_2}$), 1.81-1.64 (m, 1H, $NCH_2CHCH_2C\underline{H_2}$); HRMS (ESI): m/z $[M+H]^+$. Calcd for $C_{27}H_{28}N_7O_6S$: 578.1822; found: 578.1819.

Example 26

Synthesis of (R)—N-(7-(1-(1-acryloylpiperidin-3)-4-amino-H-pyrazolo[3,4-d]pyrimidin-3-)benzo[d][1,3]dioxo heterocyclopenten-4)-2-naphthalenesulfonamide (I-26)

Synthesis of N-(7-(4,4,5,5-tetramethyl-1,3,2-dioxaborolan-2-yl)benzo[d][1,3]dioxo heterocyclopenten-4)naphthalene-2-sulfonamide (IV-26)

Using compound XI (1.00 g, 3.80 mmol) and 2-naphthalenesulfonyl chloride (1.29 g, 5.70 mmol) as raw materials, the operation process was the same as that of compound IV-25 to obtain 1.02 g of a white solid with a yield of 59.2%, m.p. at 180-182° C. $^1H$-NMR (300 MHz, $CDCl_3$) ((ppm): 8.41 (s, 1H, ArH), 7.94-7.84 (m, 3H, ArH), 7.81 (d, J=8.76 Hz, 1H, ArH), 7.66-7.54 (m, 2H, ArH), 7.16-7.07 (m, 2H, ArH), 6.76 (s, 1H, NHCO), 5.80 (s, 2H, $OCH_2O$), 1.30 (s, 12H, $4CH_3$).

Synthesis of (R)-3-(4-amino-3-(7-(2-naphthalenesulfonamido)benzo[d][1,3]dioxo heterocyclopenten-4)-1H-tert-butyl-pyrazolo[3,4-d]pyrimidin-1-)piperidine-1-tert-butyl formate (V-26)

Using compounds III-1 (0.80 g, 1.80 mmol) and IV-26 (0.98 g, 2.16 mmol) as raw materials, the operation process was the same as that of compound V-1 to obtain 718 mg of a light-yellow solid with a yield of 61.9%, m.p. at 172-174° C. $^1H$-NMR (300 MHz, $CDCl_3$) δ (ppm): 8.44 (s, 1H, ArH), 8.32 (s, 1H, ArH), 7.99-7.80 (m, 4H, ArH), 7.70-7.57 (m, 2H, ArH), 7.50 (s, 1H, NH), 7.30-7.23 (m, 1H, ArH), 7.03 (d, J=8.46 Hz, 1H, ArH), 5.85 (s, 2H, $OCH_2O$), 5.66 (s, 2H, $NH_2$), 4.88-4.73 (m, 1H, $CHC\underline{H_2}NBoc$), 4.36-4.19 (m, 1H, $\underline{CH}CH_2NBoc$), 4.17-4.03 (m, 1H, $CHC\underline{H_2}NBoc$), 3.43-3.28 (m, 1H, $NC\underline{H_2}CH_2$), 2.88-2.73 (m, 1H, $NC\underline{H_2}CH_2$), 2.25-2.08 (m, 2H, $NCH_2CHC\underline{H_2}$), 1.91-1.79 (m, 1H, $NCH_2C\underline{H_2}$), 1.73-1.60 (m, 1H, $NCH_2C\underline{H_2}$), 1.42 (s, 9H, NBoc).

Synthesis of (R)—N-(7-(4-amino-1-(piperidin-3)-1H-pyrazolo[3,4-d]pyrimidin-3)benzo[d][1,3]dioxo heterocyclopenten-4)-2-naphthalenesulfonamide (VI-26)

Using compound V-26 (907 mg, 1.41 mmol) as the raw material, the operation process was the same as that of compound VI-1 to obtain 588 mg of a light-yellow solid with a yield of 76.7%, which was directly used in the next step without further purification.

Synthesis of (R)—N-(7-(1-(1-acryloylpiperidin-3)-4-amino-1H-pyrazolo[3,4-d]pyrimidin-3-)benzo[d][1,3]dioxo heterocyclopenten-4)-2-naphthalenesulfonamide (I-26)

Using compound VI-26 (500 mg, 0.92 mmol) and acryloyl chloride (87 mg, 0.80 mmol) as raw materials, the procedure was the same as that of target compound I-1 to obtain 134 mg of a white solid with a yield of 24.3%, m.p. at 166.5-167° C. $^1H$-NMR (300 MHz, $CDCl_3$) δ (ppm): 8.44 (s, 1H, ArH), 8.30 (d, J=8.85 Hz, 1H, ArH), 8.02-7.80 (m, 4H, ArH), 7.71-7.54 (m, 2H, ArH), 7.21 (d, J=8.13 Hz, 1H, ArH), 7.00 (d, J=7.95 Hz, 1H, ArH), 6.70-6.46 (m, 1H, $CH{=}CH_2$), 6.38-6.19 (m, 1H, $CH{=}CH_2$), 6.03-5.77 (m, 3H, $NH_2$, $OCH_2O$), 5.75-5.59 (m, 1H, $CH{=}CH_2$), 4.92-4.74 (m, 1.5H, $NC\underline{H_2}C\underline{H}$), 4.67-4.52 (m, 0.5H, $NCH_2C\underline{H}$), 4.23-4.09 (m, 0.5H, $N\underline{CH_2}CH$), 4.08-3.95 (m, 0.5H, $NC\underline{H_2}CH$), 3.78-3.63 (m, 0.5H, $NC\underline{H_2}CH_2$), 3.38-3.23 (m, 0.5H, $NC\underline{H_2}CH_2$), 3.21-3.09 (m, 0.5H, $NC\underline{H_2}CH_2$), 2.91-2.76 (m, 0.5H, $NC\underline{H_2}CH_2$), 2.45-2.08 (m, 3H, $NCH_2CHC\underline{H_2}$, $NH_2$), 2.03-1.88 (m, 1H, $NCH_2C\underline{H_2}$), 1.78-1.52 (m, 1H, $NCH_2C\underline{H_2}$); HRMS (ESI): m/z $[M+H]^+$. Calcd for $C_{30}H_{28}N_7O_5S$: 598.1873; found: 598.1873.

Example 27

Synthesis of (R)—N-(7-(4-amino-1-(1-(2-cyano-3-cyclopropylacryloyl)piperidin-3-)-1H-pyrazolo[3,4-d]pyrimidin-3-)benzo[d][1,3]dioxo heterocyclopenten-4-)benzamide (I-27)

Synthesis of (R)—N-(7-(4-amino-1-(1-(2-cyanoacetyl)piperidin-3)-1H-pyrazolo[3,4-d]pyrimidine-3-)benzo[d][1,3]dioxo heterocyclopenten-4-)benzamide (XII-27)

Dissolved compound VI-1 (300 mg, 0.66 mmol), cyanoacetic acid (67 mg, 0.79 mmol), HOBt (133 mg, 0.98 mmol), EDCI (189 mg, 0.98 mmol) and TEA (133 mg, 1.31 mmol) in 6 mL DMF, stirred at room temperature for 12 hours. The post-processing method was the same as that of compound I-4 to obtain 210 mg of a white solid with a yield of 61.1%, m.p. at 167.5-169.5° C. $^1H$-NMR (300 MHz, DMSO-$d_6$) δ (ppm): 10.25 (s, 1H, NH), 8.24 (d, J=6.09 Hz, 1H, ArH), 7.99 (d, J=7.95 Hz, 2H, ArH), 7.68-7.49 (m, 3H, ArH), 7.20 (d, J=7.95 Hz, 1H, ArH), 7.10-6.99 (m, 1H, ArH), 6.15 (s, 2H, $OCH_2O$), 4.92-4.80 (m, 0.5H, $NCH_2CH$), 4.77-4.64 (m, 0.5H, $NCH_2CH$), 4.48-4.38 (m, 0.5H, $NCH_2CH$), 4.16-4.06 (m, 2H, $CNCH_2CO$), 4.05-3.99 (m, 0.5H, $NCH_2CH$), 3.97-3.85 (m, 0.5H, $NCH_2CH$), 3.80-3.64 (m, 1H, $NCH_2CH$, $NCH_2CH_2$), 3.27-3.13 (m, 1H, $NCH_2CH_2$), 3.06-2.95 (m, 0.5H, $NCH_2CH_2$), 2.25-2.03 (m, 2H, $NCH_2CHCH_2$), 1.94-1.54 (m, 2H, $NCH_2CH_2$).

Synthesis of (R)—N-(7-(4-amino-1-(1-(2-cyano-3-cyclopropylacryloyl)piperidin-3-)-1H-pyrazolo[3,4-d]pyrimidin-3-)benzo[d][1,3]dioxo heterocyclopenten-4-)benzamide (I-27)

Mix XII-27 (100 mg, 0.19 mmol), methanol (3 mL), piperidine (24 mg, 0.29 mmol) and cyclopropanaldehyde (20 mg, 0.29 mmol) and react at room temperature for 2 hours. Concentrate under reduced pressure, dissolve in ethyl acetate, wash with water (10 mL×3) and saturated sodium chloride (10 mL×3) successively, and concentrate under reduced pressure to obtain a crude product, which was subjected to column chromatography (eluent: dichloromethane:methanol=100-60:1) to obtain 68 mg of a white solid with a yield of 61.8%, m.p. at 155.5-157° C. $^1$H-NMR (300 MHz, $CDCl_3$) δ (ppm): 8.37 (s, 1H, ArH), 8.07 (s, 1H, NH), 8.03-7.92 (m, 3H, ArH), 7.67-7.50 (m, 3H, ArH), 7.16 (d, J=8.61 Hz, 1H, ArH), 6.70-6.49 (m, 1H, $CH{=}CH_2$), 6.15 (s, 2H, $OCH_2O$), 5.97 (s, 2H, $NH_2$), 5.04-4.89 (m, 1H, $NCH_2CH$), 4.69-4.47 (m, 0.5H, $NCH_2CH$), 4.37-4.18 (m, 1H, $NCH_2CH$), 3.74-3.48 (m, 0.5H, $NCH_2CH$), 3.41-3.06 (m, 1H, $NCH_2CH_2$), 2.52-2.38 (m, 1H, $NCH_2CH_2$), 2.35-2.24 (m, 1H, $CHCH_2CH_2$), 2.23-2.12 (m, 2H, $CHCH_2CH_2$), 2.11-1.99 (m, 2H, $CHCH_2CH_2$, $C{=}CCH$), 1.93-1.74 (m, 1H, $C{=}CCHCH_2CH_2$), 1.39-1.13 (m, 3H, $C{=}CCHCH_2CH_2$); HRMS (ESI): m/z $[M+H]^+$. Calcd for $C_{31}H_{29}N_8O_4$: 577.2312; found: 577.2318.

Example 28

Synthesis of (S)—N-(7-(1-(1-acryloylpiperidin-3)-4-amino-1H-pyrazolo[3,4-d]pyrimidin-3-)benzo[d][1,3]dioxo heterocyclopenten-4)-4-(dimethylamino)benzamide (I-28)

Replace compound VIII-1 with (R)-1-tert-butoxycarbonyl-3-hydroxypiperidine (VIII-3), and the experimental operation refers to the preparations of compound I-1 or 1-13 to obtain a white solid 1-28, m.p. at 160-162° C. $^1$H-NMR (300 MHz, $CDCl_3$) δ (ppm): 8.32 (s, 1H, ArH), 8.00 (d, J=8.88 Hz, 1H, ArH), 7.86 (s, 1H, NH), 7.81 (d, J=8.04 Hz, 2H, ArH), 7.10 (d, J=8.73 Hz, 1H, ArH), 6.71 (d, J=8.49 Hz, 2H, ArH), 6.66-6.52 (m, 1H, $CH{=}CH_2$), 6.35-6.22 (m, 2H, $CH{=}CH_2$, $NH_2$), 6.11 (s, 2H, $OCH_2O$), 5.75-5.61 (m, 1H, $CH{=}CH_2$), 4.97-4.80 (m, 1.5H, $NCH_2CH$), 4.70-4.54 (m, 0.5H, $NCH_2CH$), 4.30-4.14 (m, 0.5H, $NCH_2CH$), 4.09-3.95 (m, 0.5H, $NCH_2CH$), 3.86-3.69 (m, 0.5H, $NCH_2CH_2$), 3.46-3.31 (m, 0.5H, $NCH_2CH_2$), 3.25-3.13 (m, 0.5H, $NCH_2CH_2$), 3.06 (s, 6H, $N(CH_3)_2$), 2.92-2.79 (m, 1.5H, $NCH_2CH_2$, $NH_2$), 2.47-2.35 (m, 1H, $NCH_2CHCH_2$), 2.30-2.17 (m, 1H, $NCH_2CHCH_2$), 2.08-1.91 (m, 1H, $NCH_2CH_2$), 1.82-1.64 (m, 1H, $NCH_2CH_2$); HRMS (ESI): m/z $[M+H]^+$. Calcd for $C_{29}H_{31}N_8O_4$: 555.2468; found: 555.2471.

Example 29

Synthesis of (S)—N-(7-(1-((1-acryloylpyrrolidin-2-yl)methyl)-4-amino-1H-pyrazolo[3,4-d]pyrimidin-3-yl)Benzo[d][1,3]dioxol-4-yl)-4-dimethylaminobenzamide (I-29)

Synthesis of (S)-2-((4-amino-3-iodo-1H-pyrazolo[3,4-d]pyrimidin-1-yl)methyl)pyrrolidine-1-carboxylic acid tert-butyl ester (III-5)

Compound VII-1 (1.50 g, 5.75 mmol), Boc-L-prolinol (VIII-4) (2.31 g, 11.49 mmol), $PPh_3$ (3.01 g, 11.49 mmol) and anhydrous THF (100 mL) were mixed under nitrogen protection, stirred for 30 minutes under an ice bath, added DIAD (2.32 g, 11.49 mmol), after the addition was completed, reacted at room temperature for 18 hours. The post-processing method was the same as that of compound 111-1 to obtain 1.48 g of a light-yellow solid with a yield of 58.0%, m.p. at 176-178° C. $^1$H-NMR (300 MHz, $CDCl_3$) δ (ppm): 8.36 (s, 1H, ArH), 6.24 (s, 2H, $NH_2$), 4.65-4.27 (m, 3H, $NCH_2CHNBoc$), 3.51-3.26 (m, 2H, $CH_2CH_2CH_2NBoc$), 2.00-1.77 (m, 4H, $CH_2CH_2CH_2NBoc$), 1.48 (s, 9H, $3CH_3$).

Synthesis of (S)-2-((4-amino-3-(7-(4-(dimethylamino)benzamido)benzo[d][1,3]dioxole-4-Base)-1H-pyrazolo[3,4-d]pyrimidin-1-yl)methyl)pyrrolidine-1-carboxylic acid tert-butyl ester (V-29)

Using compounds III-5 (0.80 g, 1.80 mmol) and IV-13 (0.89 g, 2.16 mmol) as raw materials, the operation process was the same as that of compound V-1 to obtain 820 mg of a light-yellow solid with a yield of 75.8%, m.p. at 138-140° C. $^1$H-NMR (300 MHz, $CDCl_3$) δ (ppm): 8.38 (s, 1H, ArH), 8.06 (d, J=8.64 Hz, 1H, ArH), 7.91-7.82 (m, 3H, ArH, NHCO), 7.17 (d, J=8.73 Hz, 1H, ArH), 6.76 (d, J=8.70 Hz, 2H, ArH), 6.15 (s, 2H, $OCH_2O$), 5.95 (br, 2H, $NH_2$), 4.72-4.59 (m, 1H, $NCH_2CHNBoc$), 4.46-4.35 (m, 1H, $NCH_2CHNBoc$), 3.50-3.38 (m, 1H, $NCH_2CHNBoc$), 3.35-3.24 (m, 1H, $CH_2CH_2CH_2NBoc$), 3.11 (s, 6H, $N(CH_3)_2$), 3.07-3.03 (m, 1H, $CH_2CH_2CH_2NBoc$), 2.01-1.78 (m, 4H, $CH_2CH_2CH_2NBoc$), 1.48 (s, 9H, $3CH_3$).

Synthesis of (S)—N-(7-(4-amino-1-(pyrrolidin-2-ylmethyl)-1H-pyrazolo[3,4-d]pyrimidin-3-yl)benzo[d][1,3]dioxol-4-yl)-4-dimethylaminobenzamide (VI-29)

Using compound V-29 (650 mg, 1.08 mmol) as the raw material, the operation process was the same as that of compound VI-1 to obtain 443 mg of a light-yellow solid with a yield of 81.8%, which was directly used in the next step without further purification.

Synthesis of (S)—N-(7-(1-((1-acryloylpyrrolidin-2-yl)methyl)-4-amino-1H-pyrazolo[3,4-d]pyrimidin-3-yl)Benzo[d][1,3]dioxol-4-yl)-4-dimethylaminobenzamide (I-29)

Using compound VI-29 (360 mg, 0.72 mmol) and acryloyl chloride (68 mg, 0.76 mmol) as raw materials, the procedure was the same as that of compound I-1 to obtain 168 mg of a white solid with a yield of 42.1%, m.p. at 98-100° C. $^1$H-NMR (300 MHz, $CDCl_3+D_2O$) δ (ppm): 8.28 (d, J=8.19 Hz, 1H, ArH), 7.89-7.72 (m, 3H, ArH), 7.01 (d, J=8.52 Hz, 1H, ArH), 6.64 (d, J=8.52 Hz, 2H, ArH), 6.42-6.31 (m, 1H, CH═$CH_2$), 6.28-6.16 (m, 1H, CH═$CH_2$), 6.09-5.97 (m, 2H, $OCH_2O$), 5.71-5.45 (m, 1H, CH═$CH_2$), 4.85-4.26 (m, 5H, $NCH_2CHN$, $NH_2$), 3.70-3.52 (m, 1H, $NCH_2CH_2$), 3.48-3.37 (m, 1H, $NCH_2CH_2$), 3.00 (s, 6H, $2CH_3$), 2.11-1.53 (m, 4H, $NCH_2CH_2CH_2$); HRMS (ESI): m/z $[M+H]^+$. Calcd for $C_{29}H_{31}N_8O_4$: 555.2468; found: 555.2471.

Example 30

Synthesis of (R)—N-(7-(1-((1-acryloylpyrrolidin-2-yl)methyl)-4-amino-1H-pyrazolo[3,4-d]pyrimidin-3-yl)Benzo[d][1,3]dioxol-4-yl)-4-dimethylaminobenzamide (I-30)

Replace compound VIII-4 with Boc-D-prolinol (VIII-5), and the experimental operation refers to the preparations of compound I-29 to obtain 157 mg of a white solid with a yield of 30.7%, m.p. at 98-100° C. $^1H$-NMR (300 MHz, $CDCl_3$) δ (ppm): 8.37 (d, J=7.65 Hz, 1H, ArH), 8.05-7.94 (m, 2H, ArH, NHCO), 7.85 (d, J=8.70 Hz, 2H, ArH), 7.11 (d, J=8.61 Hz, 1H, ArH), 6.74 (d, J=8.79 Hz, 2H, ArH), 6.48-6.41 (m, 1H, CH═$CH_2$), 6.38-6.27 (m, 1H, CH═$CH_2$), 6.18-6.10 (m, 3H, $NH_2$, $OCH_2O$), 5.76-5.58 (m, 1H, CH═$CH_2$), 4.81-4.36 (m, 3H, $NCH_2CHN$), 3.82-3.61 (m, 1H, $NCH_2CH_2$), 3.56-3.45 (m, 1H, $NCH_2CH_2$), 3.09 (s, 6H, $2CH_3$), 2.73 (s, 1H, $NH_2$), 2.19-1.79 (m, 4H, $NCH_2CH_2CH_2$); HRMS (ESI): m/z $[M+H]^+$. Calcd for $C_{29}H_{31}N_8O_4$: 555.2468; found: 555.2470.

Example 31

Synthesis of (R)—N-(7-(1-(1-acryloylpiperidin-3)-4-amino-1H-pyrazolo[3,4-d]pyrimidin-3-yl)benzo[d][1,3]dioxo heterocyclopenten-4-)-5-fluorobenzofuran-2-carboxamide (I-31)

Synthesis of 4-methoxy-N-(7-(4,4,5,5-tetramethyl-1,3,2-dioxaborolan-2-)benzo[d][1,3]dioxo heterocyclopenten-4-)5-fluorobenzo[b]furan-2-carboxamide (IV-31)

Using XI (321 mg, 0.12 mmol), 5-Fluorobenzo[b]furan-2-carboxylic acid as the starting material, the operation process was the same as that of compound IV-2 to obtain 407 mg of a yellow solid with a yield of 87.01%, m.p. at 92.0-94.0° C. $^1H$-NMR (300 MHz, $CDCl_3$) δ (ppm): 8.39 (s, 1H, NHCO), 7.94 (d, J=8.49 Hz, 1H, ArH), 7.62 (s, 1H, ArH), 7.56 (dd, J=9.06 Hz, 1H, ArH), 7.41 (dd, J=8.16 Hz, 1H, ArH), 7.34 (d, J=8.49 Hz, 1H, ArH), 7.24 (td, J=9.00 Hz, 1H, ArH), 6.18 (s, 2H, $OCH_2O$), 1.42 (s, 12H, $4CH_3$).

Synthesis of (R)-3-(4-amino-3-(7-(5-fluorobenzo[b]furan-2-carboxamido)benzo[d][1,3]dioxo heterocyclopenten-4)-1H-pyrazolo[3,4-d]pyrimidin-1-)piperidine-1-tert-butyl formate (V-31)

Using compounds III-1 (345 mg, 1.78 mmol) and IV-31 (300 mg, 0.7 mmol) as raw materials, the operation process was the same as that of compound V-1 to obtain 314 mg of a light-yellow solid with a yield of 72.86%, m.p. at 204-206° C. $^1H$-NMR (300 MHz, $CDCl_3$) δ (ppm): 8.40 (s, 1H, NHCO), 8.39 (s, 1H, ArH), 8.05 (d, J=8.7 Hz, 1H, ArH), 7.63 (s, 1H, ArH), 7.56 (dd, J=9.56 Hz, 1H, ArH), 7.40 (dd, J=8.13 Hz, 1H, ArH), 7.23 (td, J=9.00 Hz, 1H, ArH), 7.17 (d, J=8.73 Hz, 1H, ArH), 6.20 (s, 2H, $OCH_2O$), 5.76 (s, 2H, $NH_2$), 4.98-4.80 (m, 1H, $CHCH_2NBoc$), 4.50-4.25 (m, 1H, $CHCH_2NBoc$), 4.25-4.10 (m, 1H, $CHCH_2NBoc$), 3.50-3.32 (m, 1H, $NCH_2CH_2$), 2.95-2.80 (m, 1H, $NCH_2CH_2$), 2.38-2.26 (m, 1H, $NCH_2CHCH_2$), 2.25-2.17 (m, 1.0H, $NCH_2CHCH_2$, $NCH_2CH_2$), 1.81-1.72 (m, 1.0H, $NCH_2CH_2$), 1.47 (s, 9H, NBoc).

Synthesis of (R)—N-(7-(4-amino-1-(piperidin-3)-1H-pyrazolo[3,4-d]pyrimidin-3-)benzo[d][1,3]dioxo heterocyclopenten-4-)-5-fluorobenzo[b]furan-2-carboxamide (VI-31)

Using compound V-31 (300 mg, 0.49 mmol) as the raw material, the operation process was the same as that of compound VI-1 to obtain 206 mg of a light-yellow solid, which was directly used in the next step without further purification.

Synthesis of (R)—N-(7-(1-(1-acryloylpiperidin-3)-4-amino-1H-pyrazolo[3,4-d]pyrimidin-3-yl)benzo[d][1,3]dioxo heterocyclopenten-4)-5-fluorobenzo[b]furan-2-carboxamide (I-31)

Using compound VI-31 (200 mg, 0.39 mmol) and acryloyl chloride (37 mg, 0.4 mmol) as raw materials, the procedure was the same as that of compound I-1 to obtain 72 mg of a white solid with a yield of 32.3%, m.p. at 184.0-186.0° C. $^1H$-NMR (300 MHz, $CDCl_3$) δ (ppm): 10.55 (s, 1H, NHCO), 8.26 (s, 1H, ArH), 7.84 (s, 1H, ArH), 7.80 (q, J=9.27 Hz, 1H, ArH), 7.69 (q, J=8.64 Hz, 1H, ArH), 7.40 (td, J=9.21 Hz, 1H, ArH), 7.25 (d, J=8.64 Hz, 1H, ArH), 7.08 (d, J=8.49 Hz, 1H, ArH), 6.95-6.70 (m, 1H, CH═$CH_2$), 6.20 (s, 2H, $OCH_2O$), 6.15-6.04 (m, 1H, CH═$CH_2$), 5.86 (s, 2H, $NH_2$), 5.78-5.60 (m, 1H, CH═$CH_2$), 4.79-4.65 (m, 1H, $CHCH_2NBoc$), 4.63-4.51 (m, 0.5H, $CHCH_2NBoc$), 4.35-4.20 (m, 1H, $CHCH_2NBoc$), 4.18-4.04 (m, 1H, $NCH_2CH$), 3.81-3.65 (m, 0.5H, $CHCH_2NBoc$), 3.29-3.22 (m, 1H, $NCH_2CH_2$), 2.37-2.23 (m, 1H, $NCH_2CHCH_2$), 2.20-2.10 (m, 1H, $NCH_2CHCH_2$), 2.00-1.90 (m, 1H, $NCH_2CH_2$), 1.72-1.53 (m, 1H, $NCH_2CH_2$).

Example 32

Synthesis of (R)—N-(7-(1-(1-acryloylpiperidin-3)-4-amino-1H-pyrazolo[3,4-d]pyrimidin-3-yl)benzo[d][1,3]dioxo heterocyclopenten-4-)-benzo[b]thiophene-2-carboxamide (I-32)

Synthesis of 4-methoxy-N-(7-(4,4,5,5-tetramethyl-1,3,2-dioxaborolane-2)benzo[d][1,3]dioxo heterocyclopenten-4-)-benzo[b]thiophene-2-carboxamide (IV-32)

Using XI (2.28 g, 0.018 mol) and benzo[b]thiophene-2-formic acid (1.63 g, 0.0091 mol) as raw materials, the operation process was the same as that of compound IV-2 to obtain 2.78 g of a yellow solid with a yield of 72.09%, m.p. at 124-125° C. 1H-NMR (300 MHz, CDCl3): δ (ppm): 10.56 (s, 1H, NHCO), 8.39 (s, 1H, ArH), 8.08 (d, J=7.08 Hz, 1H, ArH), 8.03 (d, 1H, J=6.66 Hz), 7.58-7.46 (m, 2H, ArH), 7.09 (m, 2H, ArH), 6.12 (s, 2H, $OCH_2O$), 1.32 (s, 12H, $CH_3$).

Synthesis of (R)-3-(4-amino-3-(7-benzo[b]thiophene-2-carboxamide)benzo[d][1,3]dioxo heterocyclopenten-4)-1H-tert-butyl-pyrazolo[3,4-d]pyrimidin-1-)piperidine-1-tert-butyl formate (V-32)

Using compounds III-1 (1.4 g, 3.1 mmol) and IV-32 (1.2 g, 2.8 mmol) as raw materials, the operation process was the same as that of compound V-1 to obtain 834 mg of a light-yellow solid with a yield of 48.53%, m.p. at 126.0-128.0° C. $^{1}$H-NMR (300 MHz, $CDCl_3$), δ (ppm): 8.42 (s, 1H, NHCO), 8.03 (d, 1H, J=8.82 Hz, ArH), 8.00 (s, 1H, ArH), 7.99-7.92 (m, 3H, ArH), 7.58-7.44 (m, 2H, ArH), 7.20 (d, 1H, J=8.70 Hz, ArH), 6.20 (s, 2H, $OCH_2O$), 5.80 (s, 2H, $NH_2$), 4.90 (m, 1H, $CHC\underline{H}_2NBoc$), 4.52-4.28 (m, 1H, $C\underline{H}CH_2NBoc$), 4.27-4.13 (m, 1H, $CHC\underline{H}_2NBoc$), 3.62-3.33 (m, 1H, $NC\underline{H}_2CH_2$), 2.88 (m, 1H, $NC\underline{H}_2CH_2$), 2.40-2.28 (m, 1H, $NCH_2CHC\underline{H}_2$), 2.28-2.22 (m, 1H, $NCH_2CHC\underline{H}_2$), 1.83-1.74 (m, 1H, $NCH_2C\underline{H}_2$), 1.74-1.65 (1H, $NCH_2C\underline{H}_2$), 1.51 (s, 9H, $CH_3$).

Synthesis of (R)—N-(7-(4-amino-1-(piperidin-3)-1H-pyrazolo[3,4-d]pyrimidin-3)benzo[d][1,3]dioxo heterocyclopenten-4)-benzo[b]thiophene-2-carboxamide (VI-32)

Using compound V-32 (0.8 mg, 1.3 mmol) as the raw material, the operation process was the same as that of compound VI-1 to obtain 301 mg of a light-yellow solid, which was directly used in the next step without further purification.

Synthesis of (R)—N-(7-(1-(1-acryloylpiperidin-3)-4-amino-1H-pyrazolo[3,4-d]pyrimidin-3-yl)benzo[d][1,3]dioxo heterocyclopenten-4)-benzo[b]thiophene-2-carboxamide (I-32)

Using compound VI-32 (300 mg, 0.58 mmol) and acryloyl chloride (63 mg, 0.696 mmol) as raw materials, the procedure was the same as that of compound I-4 to obtain 79 mg of a white solid with a yield of 24.01%, m.p. at 162.0-164.0° C. $^{1}$H-NMR (300 MHz, $CDCl_3$): δ (ppm): $^{1}$H-NMR (300 MHz, $CDCl_3$), δ (ppm): 8.42 (s, 1H, NHCO), 8.03 (d, 1H, J=8.91 Hz, ArH), 8.01 (s, 1H, ArH), 7.98 (d, 2H, J=3.57 Hz, ArH), 7.95 (s, 1H, ArH), 7.52 (m, 2H, ArH), 7.19 (d, J=8.64 Hz, 1H, ArH), 6.75-6.60 (m, 1H, $C\underline{H}{=}CH_2$), 6.42-6.30 (m, 1H, $CH{=}C\underline{H}_2$), 6.21 (s, 2H, $OCH_2O$), 5.85-5.7 (m, 3H, $CH{=}C\underline{H}_2$, $NH_2$), 5.01-4.87 (m, 1.5H, $CHC\underline{H}_2NBoc$, $C\underline{H}CH_2NBoc$), 4.76-4.63 (m, 0.5H, $C\underline{H}CH_2NBoc$), 4.32-4.22 (m, 0.5H, $CHC\underline{H}_2NBoc$), 4.15-4.04 (m, 0.5H, $CHC\underline{H}_2NBoc$), 3.89-3.77 (m, 0.5H, $NC\underline{H}_2CH_2$), 3.75-3.52 (m, 0.5H, $NC\underline{H}_2CH_2$), 3.49-3.37 (m, 0.5H, $NC\underline{H}_2CH_2$), 3.32-3.18 (m, 0.5H, $NC\underline{H}_2CH_2$), 2.99-2.83 (m, 1H, $NCH_2CHC\underline{H}_2$), 2.51-2.38 (m, 1H, $NCH_2CHC\underline{H}_2$), 2.37-2.21 (m, 1H, $NCH_2C\underline{H}_2$), 2.11-1.99 (m, 1H, $NCH_2C\underline{H}_2$).

Example 33

Synthesis of (R)—N-(7-(1-(1-acryloylpiperidin-3-yl)-4-amino-1H-pyrazolo[3,4-d]pyrimidin-3-)benzo[d][1,3]dioxo heterocyclopenten-4)-3-(4-methylpiperazin-1-yl)benzamide (I-33)

Synthesis of 3-(4-methylpiperazin-1-yl)-N-(7-(4,4,5,5-tetramethyl-1,3,2-dioxaborolan-2-yl)Benzo[d][1,3]dioxol-4-yl)-benzamide (IV-33)

Using XI (1.43 g, 0.0055 mol) and 3-(4-methylpiperazin-1-)benzoic acid (1.00 g, 0.0045 mol) as raw materials, the operation process was the same as compound IV-2 to obtain 1.80 g of a white solid with a yield of 85.98%, m.p. at 142.0-144.0° C. $^{1}$H-NMR (300 MHz, DMSO): δ (ppm): 10.20 (s, 1H, NHCO), 8.41 (s, 1H, ArH), 7.67 (d, J=7.95 Hz, 1H, ArH), 7.52 (d, J=8.46 Hz, 1H, ArH), 7.36-7.30 (m, 1H, ArH), 7.24 (s, 1H, ArH), 7.12 (t, J=7.34 Hz, 1H, ArH), 6.12 (s, 2H, $OCH_2O$), 3.99 (s, 3H, $NCH_3$), 1.32 (s, 12H, $CH_3$).

Synthesis of (R)-3-(4-amino-3-(7-(3-(4-methylpiperazin-1-yl)benzamido)benzo[d][1,3]dioxo heterocyclopenten-4)-1H-pyrazolo[3,4-d]pyrimidin-1-)piperidine-1-tert-butyl formate (V-33)

Using compounds III-1 (0.178 mg, 4 mmol) and IV-33 (0.17 mg, 37 mmol) as raw materials, the operation process was the same as that of compound V-1 to obtain 98 mg of a light-yellow solid with a yield of 40.42%, m.p. at 182-184° C. $^{1}$H-NMR (300 MHz, DMSO), δ (ppm): 9.56 (s, 1H, NHCO), 8.41 (s, 1H, ArH), 8.02 (d, J=8.7 Hz, 1H, ArH), 7.93 (s, 1H, ArH), 7.52-7.47 (m, 1H, ArH), 7.35 (s, 1H, ArH), 7.18 (d, J=8.64, 1H, ArH), 7.13-7.17 (m, 1H, ArH), 6.16 (s, 2H, $OCH_2O$), 5.78 (s, 2H, $NH_2$), 4.96-4.83 (m, 1H, $C\underline{H}_2CHNBoc$), 4.47-4.27 (m, 1H, $CH_2C\underline{H}NBoc$), 4.26-4.17 (m, 1H, $C\underline{H}_2CHNBoc$), 3.41-3.35 (m, 4H, $CH_2NCH_2$), 3.25-3.19 (m, 4H, $C\underline{H}_2N(CH_3)C\underline{H}_2$), 2.95-2.81 (m, 1H, $NC\underline{H}_2CH_2$), 2.49 (s, 3H, $NC\underline{H}_3$), 2.40-2.29 (m, 1H, $NC\underline{H}_2CH_2$), 2.28-2.19 (m, 1.5H, $NCH_2CHC\underline{H}_2$, $NC\underline{H}_2C\underline{H}_2$), 1.79-1.69 (m, 1.5H, $NCH_2C\underline{H}_2$), 1.49 (s, 9H, Boc).

Synthesis of (R)—N-(7-(4-amino-1-(piperidin-3)-1H-pyrazolo[3,4-d]pyrimidin-3-)benzo[d][1,3]dioxo heterocyclopenten-4-)-3-(4-methylpiperazin-1-yl)benzamide (VI-33)

Using compound V-33 (98 mg, 17 mmol) as the raw material, the operation process was the same as that of compound VI-1 to obtain 80 mg of a light-yellow solid, which was directly used in the next step without further purification.

Synthesis of (R)—N-(7-(1-(1-acryloylpiperidin-3-yl)-4-amino-1H-pyrazolo[3,4-d]pyrimidin-3-)benzo[d][1,3]dioxo heterocyclopenten-4)-3-(4-methylpiperazin-1-yl)benzamide (I-33)

Using compound VI-33 (80 mg, 0.14 mmol) and acryloyl chloride (15 mg, 0.16 mmol) as raw materials, the procedure was the same as that of compound I-4 to obtain 49 mg of a white solid with a yield of 55.85%, m.p. at 152.0-154.0° C. $^{1}$H-NMR (300 MHz, DMSO), δ (ppm): 10.23 (s, 1H, NHCO), 8.41 (s, 1H, ArH), 8.04 (d, J=8.7 Hz, 1H, ArH), 7.52-7.47 (m, 1H, ArH), 7.33 (d, J=7.08 Hz, 1H, ArH), 7.18 (d, 1H, J=8.7 Hz, ArH), 7.16 (s, 1H, ArH), 7.12-7.07 (m, 1H, ArH), 6.71-6.58 (m, 1H, $C\underline{H}{=}CH_2$), 6.39-6.29 (m, 1H, $CH{=}C\underline{H}_2$), 6.16 (s, 2H, $OCH_2O$), 5.80-5.66 (m, 3H, $NH_2$, $CH{=}C\underline{H}_2$), 4.99-4.85 (m, 1.5H, $C\underline{H}_2CHNBoc$, $CH_2C\underline{H}NBoc$), 4.72-4.62 (m, 0.5H, $CH_2C\underline{H}NBoc$), 4.30-4.20 (m, 0.5H, $C\underline{H}_2CHNBoc$), 4.15-4.02 (m, 0.5H, $C\underline{H}_2CHNBoc$), 3.86-3.73 (m, 0.5H, $NC\underline{H}_2CH_2$), 3.41-3.36 (m, 4H, $CH_2NCH_2$), 3.25-3.19 (m, 4H, $CH_2N(CH_3)CH_2$), 2.97-2.84 (m, 0.5H, $NC\underline{H}_2CH_2$), 2.49 (s, 3H, $CH_3$), 2.45-2.36 (m, 1H, $NC\underline{H}_2CH_2$), 2.35-2.26 (m, 1H, $C\underline{H}_2CHNBoc$), 2.08-1.99 (m, 1H, $NC\underline{H}_2CHCH_2$), 1.79-1.70 (m, 2H, $NC\underline{H}_2CHCH_2$).

Example 34

Synthesis of (R)—N-(7-(1-(1-acryloylpiperidin-3-yl)-4-amino-1H-pyrazolo[3,4-d]pyrimidin-3-)benzo[d][1,3]dioxo heterocyclopenten-4-)-3-(morpholinomethyl)benzamide (I-34)

Synthesis of 3-(morpholinomethyl)-N-(7-(4,4,5,5-tetramethyl-1,3,2-dioxaborolan-2-yl)benzo[d][1,3]dioxo heterocyclopenten-4-)benzamide (IV-34)

Using compound XI (0.65 g, 0.0025 mol), 3-(morpholinomethyl)benzoic acid (0.5 g, 0.0023 mol) as raw materials, the operation process was the same as that of compound IV-2 to obtain 732 mg of a white solid with a yield of 73.32%, m.p. at 192-194° C. $^1$H-NMR (300 MHz, DMSO): δ (ppm): 10.21 (s, 1H, NHCO), 7.92 (s, 1H, ArH), 7.89 (d, J=8.31 Hz, 1H, ArH), 7.56 (d, J=6.69 Hz, 1H, ArH), 7.50 (t, J=7.77 Hz, 1H, ArH), 7.09 (d, J=7.86 Hz, 1H, ArH), 7.04 (d, J=8.31 Hz, 1H, ArH), 6.09 (s, 2H, $OCH_2O$), 5.73 (s, 2H, $NH_2$), 3.66-3.60 (m, 4H, $C\underline{H}_2NC\underline{H}_2$), 3.56 (s, 2H, $CH_2$), 2.46-2.36 (m, 4H, $C\underline{H}_2OC\underline{H}_2$), 1.32 (s, 12H, $4CH_3$).

Synthesis of (R)-3-(4-amino-3-(7-(3-(morpholinomethyl)benzamido) benzo[d][1,3]dioxo heterocyclopenten-4)-1H-pyrazolo[3,4-d]pyrimidin-1-)piperidine-1-tert-butyl carboxylate (V-34)

Using compounds III-1 (0.77 mg, 0.0017 mol) and IV-34 (0.7 mg, 0.0016 mol) as raw materials, the operation process was the same as that of compound V-1 to obtain 546 mg of a light-yellow solid with a yield of 51.99%, m.p. at 182-184° C. $^1$H-NMR (300 MHz, DMSO), δ (ppm): 10.28 (s, 1H, NHCO), 8.27 (s, 1H, ArH), 8.03-7.86 (m, 2H, ArH), 7.69-7.46 (m, 2H, ArH), 7.22 (d, J=7.95 Hz, 1H, ArH), 7.07 (d, J=7.62 Hz, 1H, ArH), 6.98-6.73 (m, 1H, $CH{=}C\underline{H}_2$), 6.28-6.02 (m, 3H, $OCH_2O$, $CH{=}C\underline{H}_2$), 5.75 (s, 2H, $N\underline{H}_2$) 5.85-5.58 (m, 1H, $CH{=}C\underline{H}_2$), 4.83-4.66 (m, 1H, $C\underline{H}_2CHNBoc$), 4.54-4.65 (m, 0.5H, $CH_2C\underline{H}NBoc$), 4.38-4.20 (m, 1H, $C\underline{H}_2CHNBoc$), 4.20-4.02 (m, 0.5H, $CH_2C\underline{H}NBoc$), 3.82-3.70 (m, 0.5H, $NC\underline{H}_2CH_2$), 3.71-3.53 (m, 4H, $CH_2NCH_2$), 3.59 (s, 2H, $CH_2$), 3.31-3.16 (m, 1H, $NC\underline{H}_2CH_2$), 3.09-2.92 (m, 0.5H, $NC\underline{H}_2CH_2$) 2.50-2.42 (m, 4H, $CH_2OCH_2$), 2.35-2.23 (m, 1H, $NCH_2CHC\underline{H}_2$) 2.22-2.19 (m, 1H, $NCH_2CHC\underline{H}_2$), 2.06-1.90 (m, 1H, $NCH_2C\underline{H}_2$), 1.75-1.54 (m, 1H, $NCH_2C\underline{H}_2$), 1.42 (s, 9H, Boc).

Synthesis of (R)—N-(7-(4-amino-1-(piperidin-3-yl)-1H-pyrazol[3,4-d]pyrimidin-3-yl)benzo[d][1,3]Dioxol-4-yl)-3-(morpholinemethyl)benzamide (VI-34)

Using compound V-34 (0.54 mg, 082 mmol) as the raw material, the operation process was the same as that of compound VI-1 to obtain 472 mg of a light-yellow solid, which was directly used in the next step without further purification.

Synthesis of (R)—N-(7-(1-(1-acryloylpiperidin-3-yl)-4-amino-1H-pyrazolo[3,4-d]pyrimidin-3-)benzo[d][1,3]dioxo heterocyclopenten-4-)-3-(morpholinomethyl)benzamide (I-34)

Using compound VI-34 (400 mg, 0.72 mmol) and acryloyl chloride (72 mg, 0.79 mmol) as raw materials, the procedure was the same as that of compound I-4 to obtain 225 mg of a white solid with a yield of 46.67%, m.p. at 148.0-150.0° C. $^1$H-NMR (300 MHz, DMSO), δ (ppm): 10.25 (s, 1H, NHCO), 8.24 (s, 1H, ArH), 7.93 (s, 1H, ArH), 7.92-7.87 (m, 1H, ArH) 7.57-7.53 (m, 1H, ArH), 7.50 (t, J=7.44 Hz, 1H, ArH), 7.18 (d, J=8.58 Hz, 1H, ArH), 7.05 (d, J=8.55 Hz, 1H, ArH), 6.93-6.71 (m, 1H, $C\underline{H}{=}CH_2$), 6.14 (s, 2H, $OCH_2O$), 6.13-6.03 (m, 1H, $CH{=}C\underline{H}_2$), 5.78 (s, 2H, $NH_2$), 5.75-5.59 (m, 1H, $CH{=}C\underline{H}_2$), 4.78-4.65 (m, 1H, $C\underline{H}_2CHNBoc$), 4.62-4.53 (m, 0.5H, $CH_2C\underline{H}NBoc$), 4.31-4.18 (m, 1H, $C\underline{H}_2CHNBoc$), 4.15-4.08 (m, 0.5H, $CH_2C\underline{H}NBoc$), 3.74-3.64 (m, 1H, $NC\underline{H}_2CH_2$), 3.63-3.58 (m, 4H, $C\underline{H}_2NC\underline{H}_2$), 3.57-3.54 (s, 2H, $C\underline{H}_2$), 3.27-3.20 (m, 1H, $NC\underline{H}_2CH_2$), 2.45-2.35 (m, 4H, $C\underline{H}_2OC\underline{H}_2$), 2.31-2.21 (m, 1H, $NCH_2CHC\underline{H}_2$), 2.17-2.08 (m, 1H, $NCH_2CHC\underline{H}_2$), 1.98-1.88 (m, 1H, $NCH_2C\underline{H}_2$), 1.69-1.52 (m, 1H, $NC\underline{H}_2C\underline{H}_2$)

Example 35

The pharmacological trials and results of the compounds as prepared as above-mentioned are as follows:

1. BTK, JAK3 Kinase Inhibitory Activity Experiment

Experimental method: The 384-well plate was divided into compound wells (starting at 10 μM, diluted three times to produce 10 concentrations), positive control wells and negative control wells; kinase solution was added to compound wells and positive control wells, and 1×kinase buffer was added to negative control wells; the solution is next centrifuged for 30 seconds and incubated at room temperature for 10 minutes. Add 15 μL of the mixed solution of ATP and substrate, shake and mix well after centrifugation and incubate at room temperature (30 minutes for JAK3, 20 minutes for BTK). Add stop detection solution to stop the reaction, and read the conversion rate with Caliper EZ reader, Data analysis: The formula is as follows:

$$\%\ \text{Inhibition} = \frac{\text{Conversion }\%\_\text{max} - \text{Conversion }\%\_\text{sample}}{\text{Conversion }\%\_\text{max} - \text{Conversion }\%\_\text{min}} \times 100$$

where Conversion %_sample is the conversion rate reading of the sample; Conversion %_min is the average value of the negative control wells representing the conversion rate reading of the wells without enzyme addition; and Conversion %_max is the average value of the positive control wells representing the conversion rate reading of the wells without adding the compound.

Fit the dose-response curve: Taking the log value of the concentration as the X-axis, and the percentage inhibition rate as the Y-axis, the dose-response curve was fitted using the log (inhibitor) vs. response-Variable slope of the software GraphPad Prism 5, so as to obtain the $IC_{50}$ value of each compound on the enzyme activity.

Experimental results: Some compounds of the invention were screened for in vitro BTK and JAK3 kinase inhibitory activity; the results are shown in Table 1.

Note: A: $IC_{50}$:0.001-0.05 μM; B: $IC_{50}$:0.05-0.5 μM; C: $IC_{50}$: >0.5 μM.

TABLE 1

Inhibitory activity of some compounds on BTK and JAK3 kinases

| Serial number | BTK ($IC_{50}$:nM) | JAK3 ($IC_{50}$:nM) |
|---|---|---|
| I-1 | A | B |
| I-2 | A | B |

TABLE 1-continued

| Inhibitory activity of some compounds on BTK and JAK3 kinases | | |
|---|---|---|
| Serial number | BTK ($IC_{50}$:nM) | JAK3 ($IC_{50}$:nM) |
| I-3 | A | B |
| I-4 | A | B |
| I-5 | A | B |
| I-6 | A | A |
| I-7 | A | A |
| I-8 | A | B |
| I-9 | A | B |
| I-10 | A | A |
| I-11 | A | A |
| I-12 | A | B |
| I-13 | A | A |
| I-14 | A | A |
| I-15 | A | A |
| I-16 | A | A |
| I-17 | A | A |
| I-18 | A | A |
| I-19 | A | A |
| I-20 | A | A |
| I-21 | A | A |
| I-22 | A | A |
| I-23 | A | B |
| I-24 | A | B |
| I-25 | A | B |
| I-26 | A | B |
| I-28 | A | B |
| I-31 | A | B |
| I-32 | A | A |
| I-33 | A | C |
| I-34 | A | C |
| Ibrutinib | A | B |

The results in Table 1 showed that the compounds of the invention have good inhibitory activity to BTK and JAK3 kinases, wherein compounds I-6, I-7, I-10, I-11, I-13-I-22 and I-32 showed excellent inhibitory activity on BTK and JAK3.

2. Proliferation Inhibitory Effect of Compounds on BaF3-TEL-JAK3 and Daudi Cells Experimental procedure: A certain number of cells in the logarithmic growth phase were inoculated in a 96-well plate and cultured at 37° C. before adding drugs. After 72 hours of drug action, after the 96-well cell plate was equilibrated to room temperature, 40 μL of Cell Titer-Glo® reagent was added to each well; each plate was then shaken for 2 minutes and allowed to stand for 10 minutes; the chemiluminescent signal was detected with an MD SpectraMax Paradigm microplate reader.

Data analysis: The formula is as follows:

$$\%\ \text{Inhibition} = \frac{(\text{Max signal} - \text{Compound signal})}{(\text{Max signal} - \text{Min signal})} \times 100$$

Max signal: DMSO signal; Min signal: medium signal.

$IC_{50}$ was calculated using GraphPad Prism 5.

Note: A: $IC_{50}$: 0.01-0.5 μM, B: $IC_{50}$: 0.5-1 μM, C: $IC_{50}$: >1 μM.

TABLE 2

| Proliferation inhibitory activity of some compounds on BaF3-JAK3 and Daudi cells | | |
|---|---|---|
| Compound | $IC_{50}$ (nM) | |
| number | BaF3-JAK3 | Daudi |
| I-1 | B | B |
| I-2 | B | B |
| I-3 | B | B |
| I-4 | B | B |
| I-6 | B | B |
| I-7 | B | B |
| I-11 | A | A |
| I-13 | A | B |
| I-15 | A | B |
| I-16 | A | A |
| I-17 | B | B |
| I-18 | B | B |
| I-20 | B | B |
| I-21 | B | B |
| I-24 | A | A |
| Ibrutinib | C | B |

The experimental results showed that the tested compounds had significantly better inhibitory activity on BaF3-JAK3 cell proliferation than ibrutinib; the test compounds showed better proliferation inhibitory ability to Daudi cells with high expression of BTK, and some test compounds had better proliferation inhibitory effect on Daudi cells than ibrutinib.

The invention claimed is:

1. A compound of formula (I):

(I)

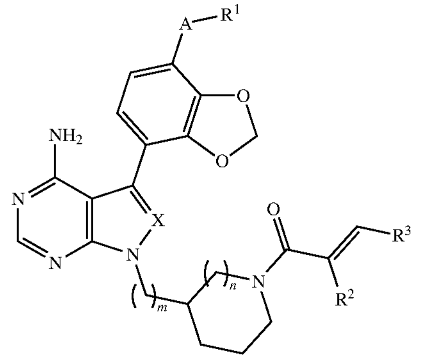

or a pharmaceutically acceptable salt or stereoisomer thereof, wherein:

A represents —NHC(O)—, —$NHC(O)CH_2$—, —$NHS(O)_2$—, —O—, or —S—;

$R^1$ represents:

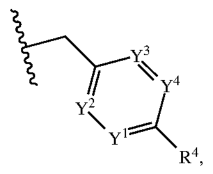

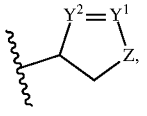

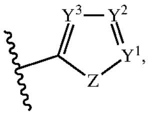

-continued

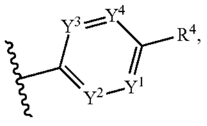

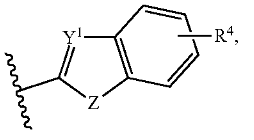

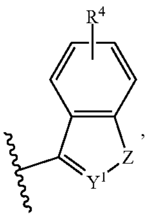

,

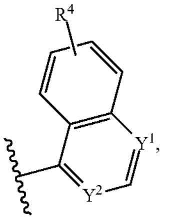

or

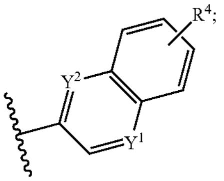

$Y^1$ represents $CR^5$ or N;
$Y^2$ represents $CR^5$ or N;
$Y^3$ represents $CR^5$ or N;
$Y^4$ represents $CR^5$ or N;
each $R^5$ independently represents H, F, Cl, Br, I, CN, $CH_3$, $CF_3$, OH, $OCH_3$, or $OCF_3$;
Z represents —$NR^6$—, —O—, or —S—;
$R^6$ represents H, $CH_3$, $CH_2CH_3$, or cyclopropyl;
each $R^4$ independently represents H, F, Cl, Br, I, CN, $NO_2$, $C_1$-$C_6$ alkyl, $CF_3$, $C(O)NH_2$, $C(O)NHCH_3$, $C(O)NHCH_2CF_3$, $NH_2$, $NHC_1$-$C_6$ alkyl, $NHC(O)CH_3$, $N(CH_3)_2$, $N(CH_2CH_3)_2$, OH, $OC_1$-$C_6$ alkyl, $OCF_3$, $OCH_2CH_2OCH_3$, pyrrolidin-1-yl, piperazin-1-yl, 4-methylpiperazin-1-yl, morpholin-4-yl, or phenyl;
X represents CH or N;
m represents 0 or 1;
n represents 0 or 1;
$R^2$ represents H, Cl, Br, or CN; and
$R^3$ represents H, $C_1$-$C_6$ alkyl, or $C_2$-$C_6$ heterocycloalkyl;
wherein the $C_2$-$C_6$ heterocycloalkyl is a saturated 4-, 5-, or 6-membered ring containing one, two, or three heteroatoms or heteroatomic groups independently selected from the group consisting of N, NH, O, and S; and
wherein the $C_1$-$C_6$ alkyl or $C_2$-$C_6$ heterocycloalkyl is substituted with one or more substituents independently selected from the group consisting of $NH_2$, $NHCH_3$, $NHC(O)CH_3$, OH, and $OCH_3$.

2. The compound according to claim 1, or a pharmaceutically acceptable salt or stereoisomer thereof, wherein the pharmaceutically acceptable salt is an acid addition salt selected from the group consisting of an acetic acid addition salt, a benzenesulfonic acid addition salt, a carbonic acid addition salt, a citric acid addition salt, a ferulic acid addition salt, a hydrobromic acid addition salt, a hydrochloric acid addition salt, a lactic acid addition salt, a maleic acid addition salt, a methanesulfonic acid addition salt, an oxalic acid addition salt, a phosphoric acid addition salt, a pyruvic acid addition salt, a succinic acid addition salt, a sulfuric acid addition salt, a tartaric acid addition salt, and a p-toluenesulfonic acid addition salt.

3. The compound according to claim 1, or a pharmaceutically acceptable salt or stereoisomer thereof, wherein:
A represents —NHC(O)—, or —$NHS(O)_2$—;
m represents 0;
n represents 1;
$R^2$ represents H; and
$R^3$ represents H.

4. The compound according to claim 1, or a pharmaceutically acceptable salt or stereoisomer thereof, wherein:
A represents —NHC(O)—, or —$NHS(O)_2$—;
m represents 1;
n represents 0;
$R^2$ represents H; and
$R^3$ represents H.

5. The compound according to claim 1, or a stereoisomer thereof, wherein the stereoisomer of the compound is of formula (II):

(II)

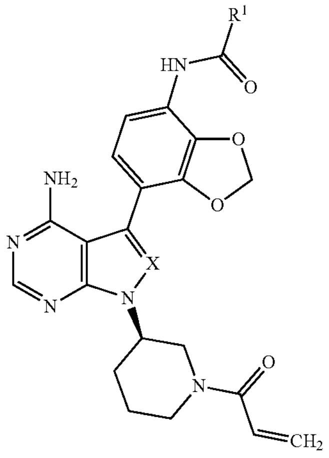

or a pharmaceutically acceptable salt thereof.

6. The compound according to claim 5, or a pharmaceutically acceptable salt thereof, wherein:
$R^1$ represents:

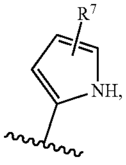

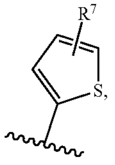

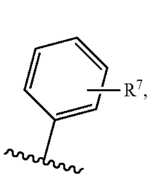

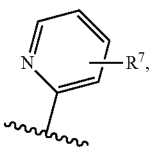

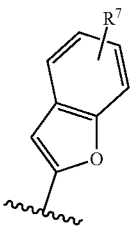

,

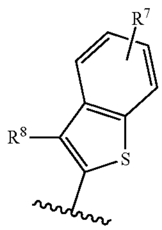

,

-continued

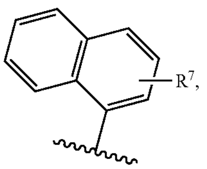

or

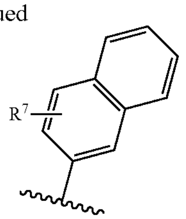

;

$R^8$ represents H, Cl, or $CH_3$; and each $R^7$ independently represents H, F, Cl, Br, CN, $CH_3$, $C(CH_3)_3$, $CF_3$, $C(O)NH_2$, $C(O)NHCH_3$, $C(O)NHCH_2CF_3$, $NH_2$, $NHC(O)CH_3$, $N(CH_3)_2$, $N(CH_2CH_3)_2$, OH, $OCH_3$, $OCF_3$, pyrrolidin-1-yl, 4-methylpiperazin-1-yl, morpholin-4-yl, or phenyl.

7. The compound according to claim 6, or a pharmaceutically acceptable salt thereof, wherein:

$R^8$ represents Cl; and each $R^7$ independently represents H, Cl, $CH_3$, $C(CH_3)_3$, $CF_3$, $C(O)NHCH_2CF_3$, $N(CH_3)_2$, $N(CH_2CH_3)_2$, or $OCH_3$.

8. A pharmaceutical composition comprising a pharmaceutically acceptable carrier and the compound according to claim 1, or a pharmaceutically acceptable salt or stereoisomer thereof.

9. A method for inhibiting Bruton's tyrosine kinase (BTK) activity in a subject, wherein the method comprises administering to the subject in need thereof a therapeutically effective amount of the compound according to claim 1, or a pharmaceutically acceptable salt or stereoisomer thereof.

10. A method for inhibiting Janus kinase 3 (JAK3) activity in a subject, wherein the method comprises administering to the subject in need thereof a therapeutically effective amount of the compound according to claim 1, or a pharmaceutically acceptable salt or stereoisomer thereof.

11. A method for inhibiting Bruton's tyrosine kinase (BTK) and Janus kinase 3 (JAK3) activity in a subject, wherein the method comprises administering to the subject in need thereof a therapeutically effective amount of the compound according to claim 1, or a pharmaceutically acceptable salt or stereoisomer thereof.

12. A method for inhibiting the activity of a Bruton's tyrosine kinase (BTK) and Janus kinase 3 (JAK3) dual-target in a subject, wherein the method comprises administering to the subject in need thereof a therapeutically effective amount of the compound according to claim 1, or a pharmaceutically acceptable salt or stereoisomer thereof.

13. A method for treating B-cell lymphoma in a subject, wherein the method comprises administering to the subject in need thereof a therapeutically effective amount of the compound according to claim 1, or a pharmaceutically acceptable salt or stereoisomer thereof.

14. A method for treating rheumatoid arthritis in a subject, wherein the method comprises administering to the subject in need thereof a therapeutically effective amount of the compound according to claim 1, or a pharmaceutically acceptable salt or stereoisomer thereof.

15. A compound selected from the group consisting of:

I-1

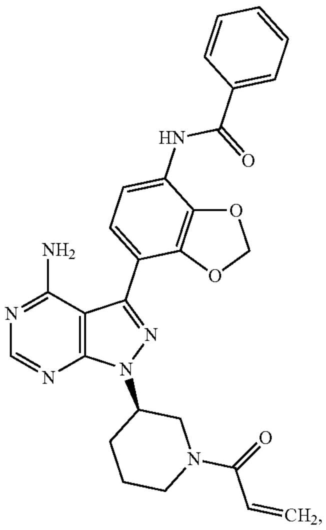

I-2

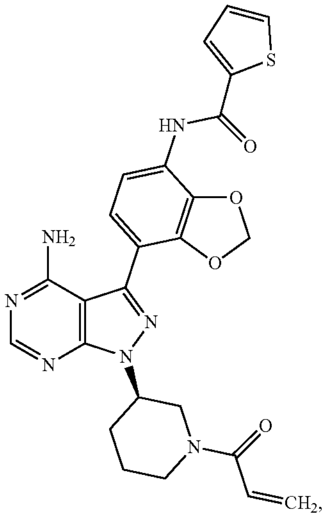

I-3

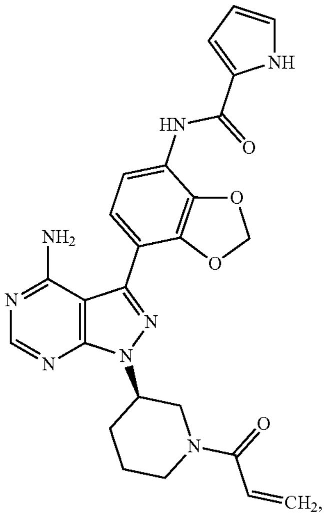

-continued
I-4
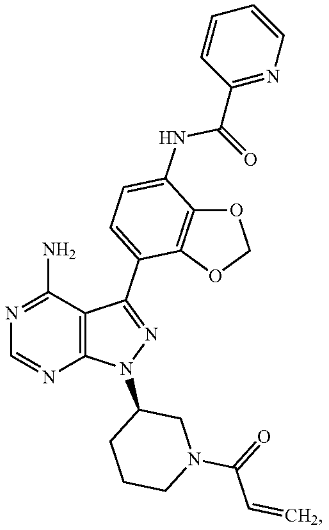
I-5
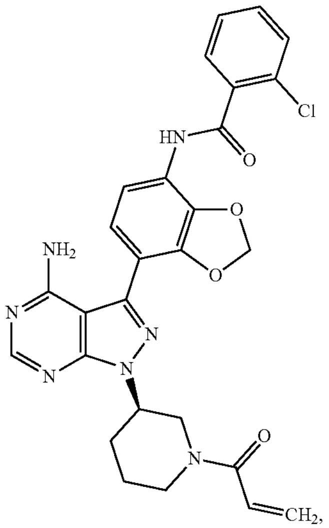
I-6
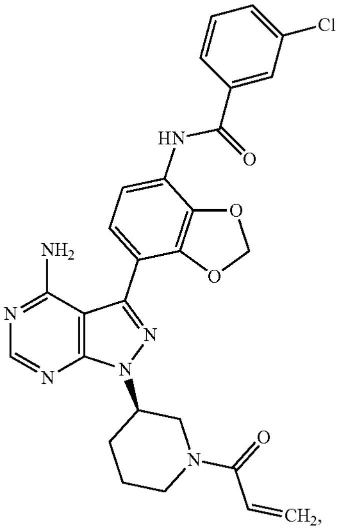
-continued
I-7
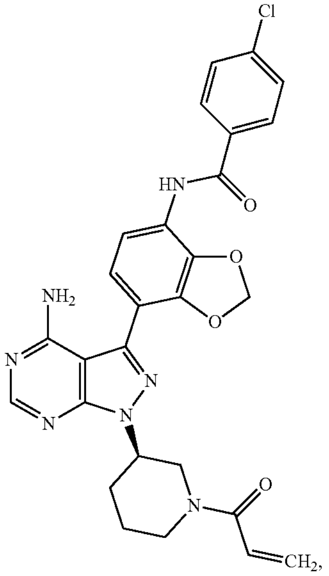
I-8
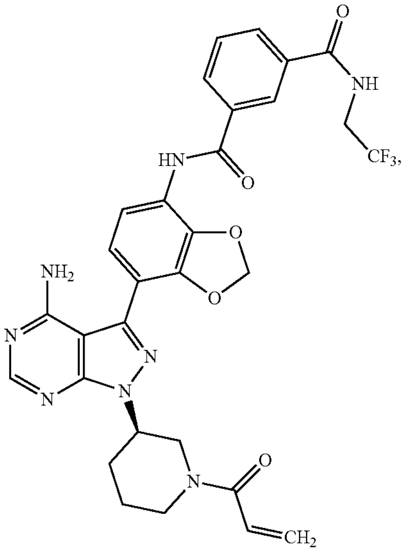

-continued
I-9
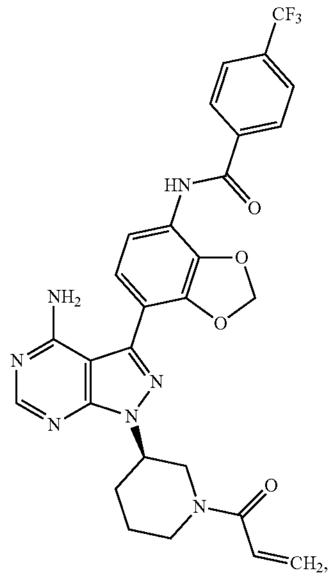
I-10
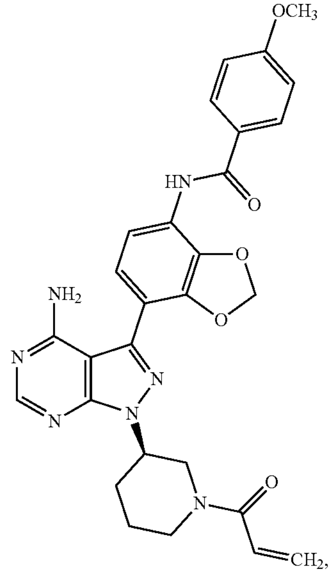
-continued
I-11
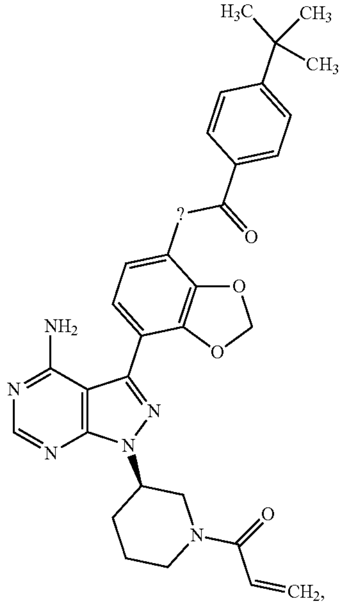
I-12
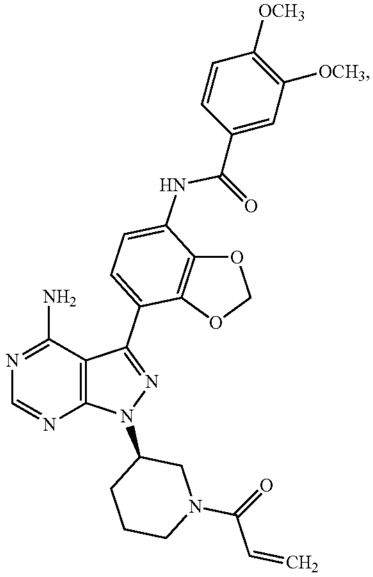

-continued
I-13
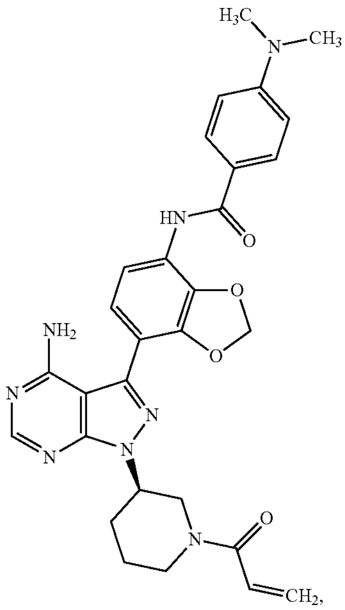
-continued
I-15
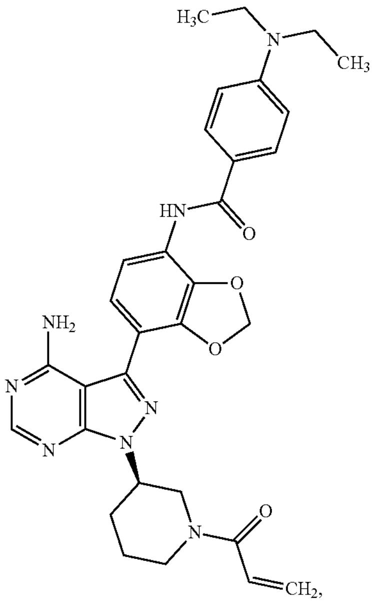
I-14
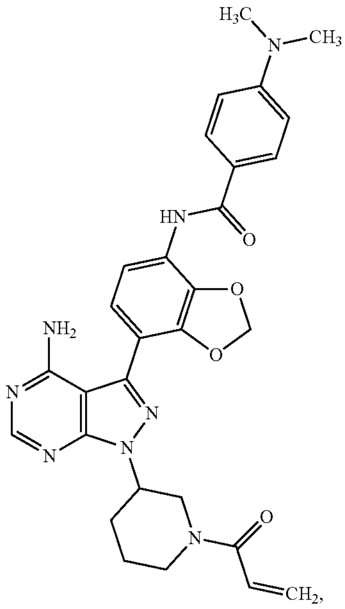
I-16
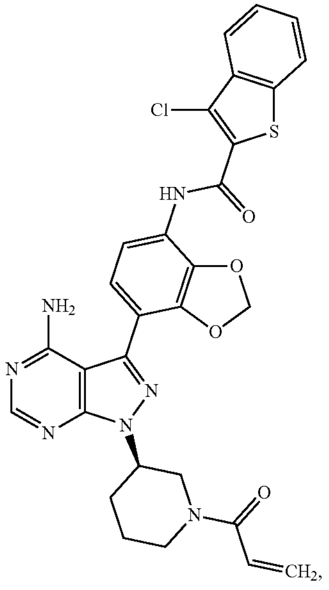

-continued
I-17
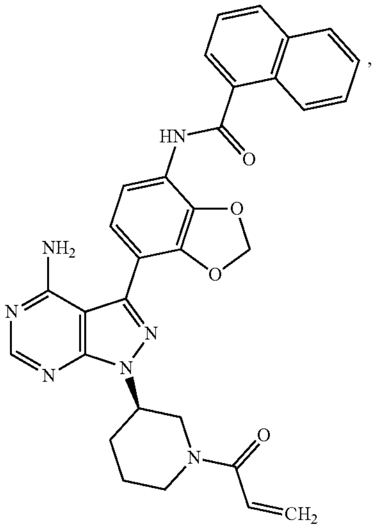
I-18
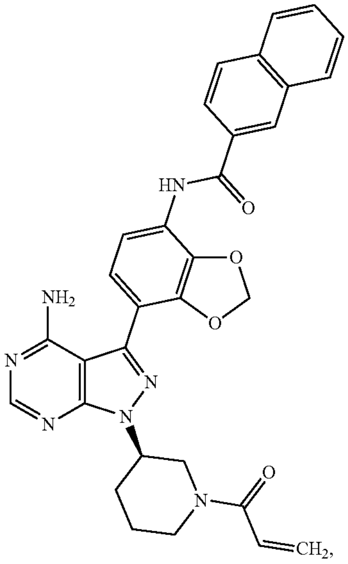
-continued
I-19
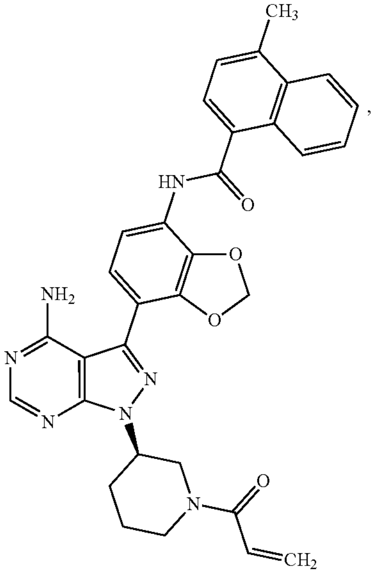
I-20
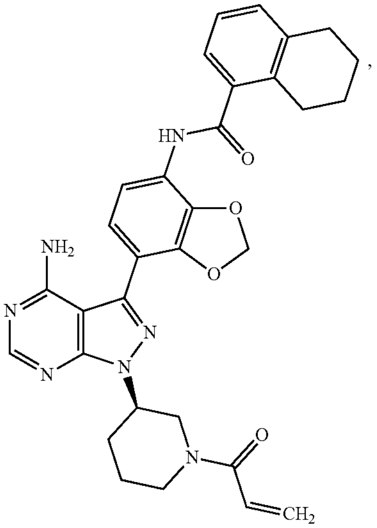
I-21
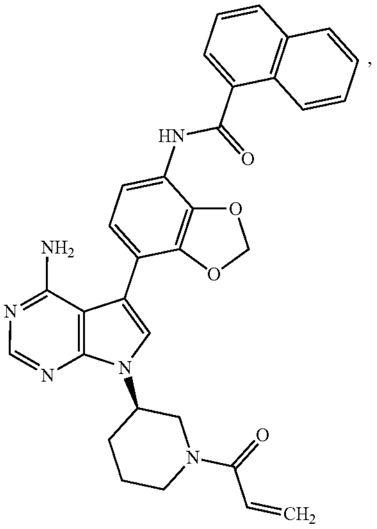

-continued
I-22
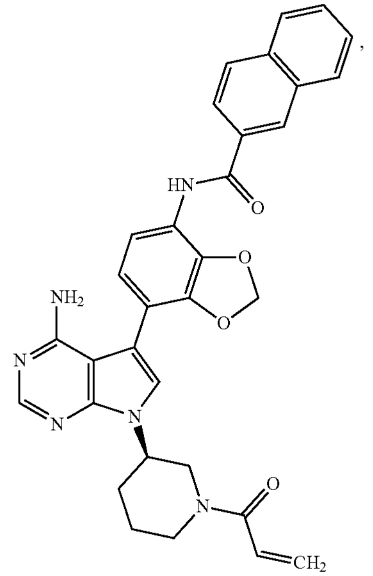
I-23
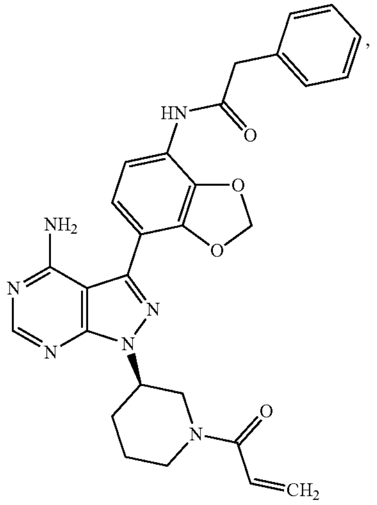
-continued
I-24
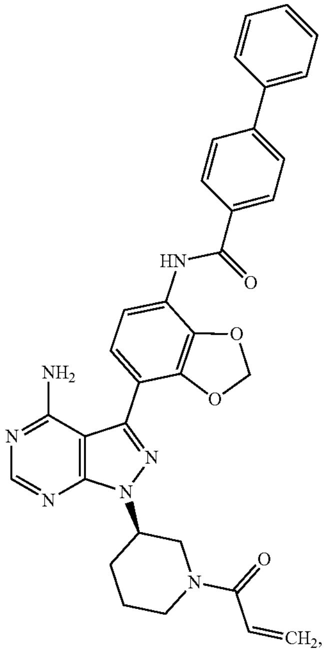
I-25
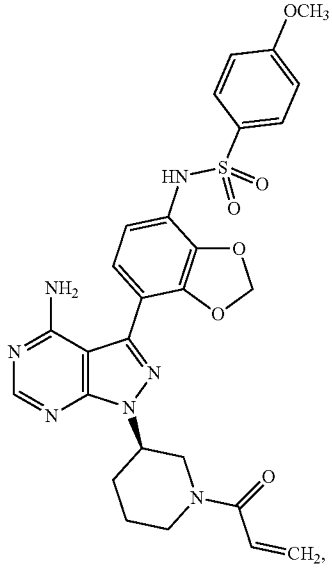

-continued
I-26
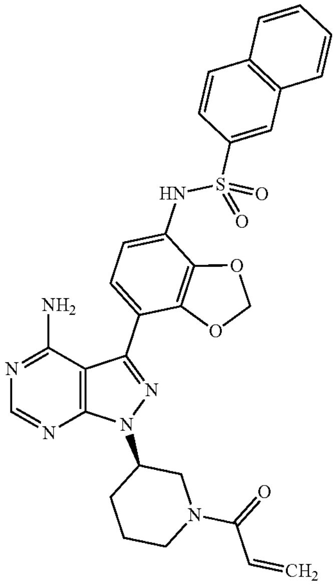
,
I-27
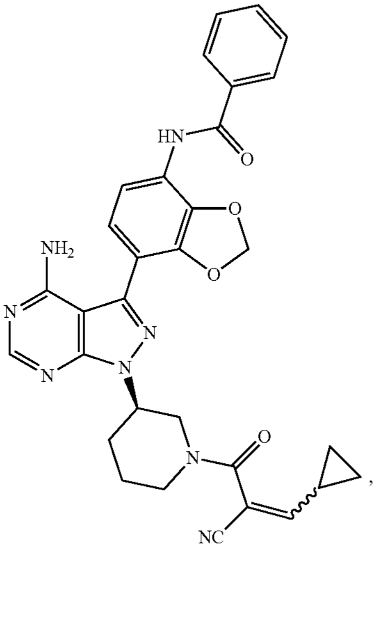
,
-continued
I-28
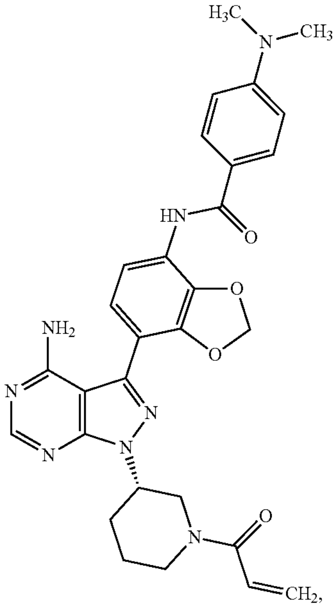
,
I-29
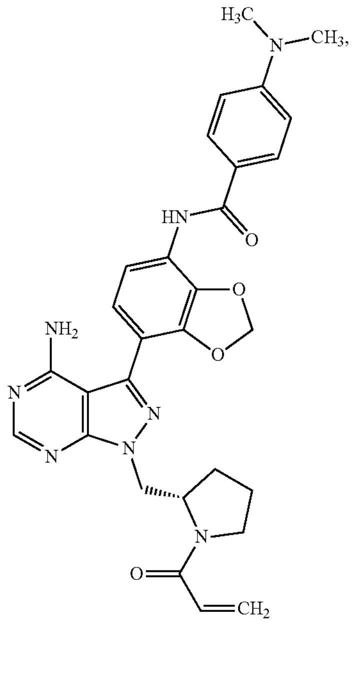

-continued
I-30
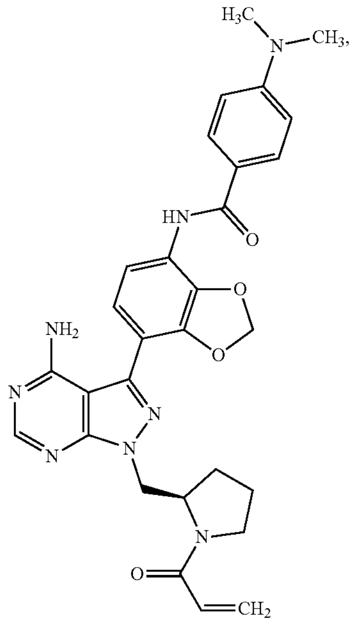
I-31
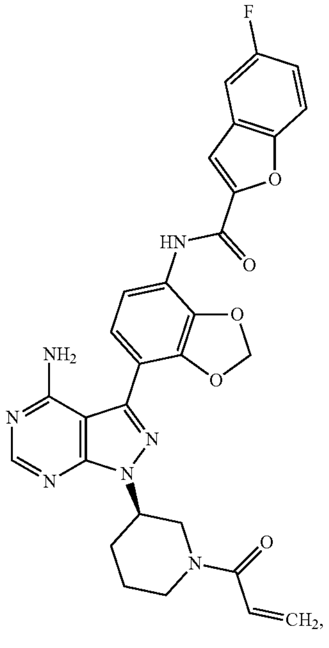
-continued
I-32
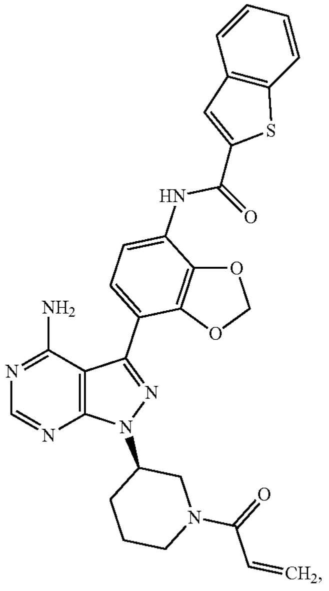
I-33
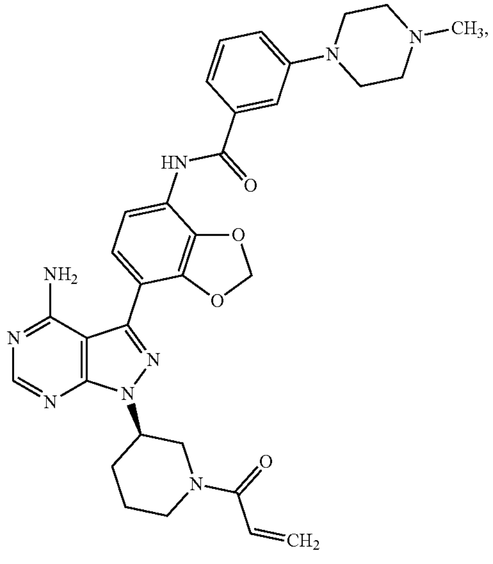
and -continued
I-34
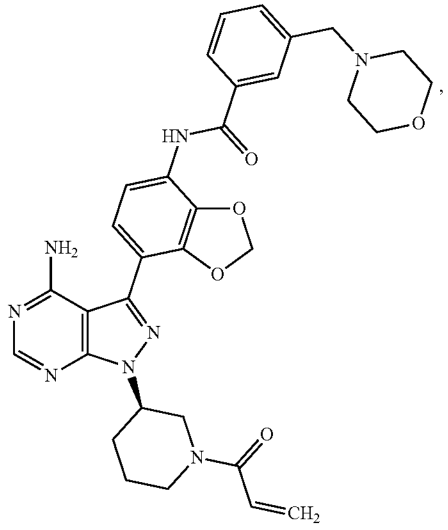
or a planimetrically acceptable salt thereof.
* * * * *